US006114114A

United States Patent [19]
Seilhamer et al.

[11] Patent Number: 6,114,114
[45] Date of Patent: *Sep. 5, 2000

[54] COMPARATIVE GENE TRANSCRIPT ANALYSIS

[75] Inventors: Jeffrey J. Seilhamer, Los Altos Hills; Randal W. Scott, Mountain View, both of Calif.

[73] Assignee: Incyte Pharmaceuticals, Inc., Palo Alto, Calif.

[*] Notice: This patent is subject to a terminal disclaimer.

[21] Appl. No.: 08/282,955

[22] Filed: Jul. 29, 1994

Related U.S. Application Data

[63] Continuation-in-part of application No. 08/187,530, Jan. 27, 1994, Pat. No. 5,840,484, which is a continuation-in-part of application No. 08/179,873, Jan. 11, 1994, abandoned, application No. 08/137,951, Oct. 14, 1993, abandoned, and application No. 08/100,523, Aug. 3, 1993, abandoned, which is a continuation-in-part of application No. 07/977,780, Nov. 19, 1992, abandoned, which is a continuation-in-part of application No. 07/916,491, Jul. 17, 1992, abandoned.

[51] Int. Cl.$^7$ ..................................................... C12Q 1/68
[52] U.S. Cl. ............................................ 435/6; 364/413.02
[58] Field of Search .............................. 435/6; 364/413.02

[56] References Cited

U.S. PATENT DOCUMENTS

| | | | |
|---|---|---|---|
| 5,270,170 | 12/1993 | Schutz et al. | 435/7.37 |
| 5,364,759 | 11/1994 | Caskey et al. | 435/6 |
| 5,371,671 | 12/1994 | Anderson et al. | 364/413.01 |

FOREIGN PATENT DOCUMENTS

| | | |
|---|---|---|
| 91/19818 | 12/1991 | WIPO. |
| 93/06121 | 4/1993 | WIPO. |
| 93/22684 | 11/1993 | WIPO. |

OTHER PUBLICATIONS

IntelliGenetics Suite, Release 5.4, Advanced Training Manual, issued Jan. 1993 by IntelliGenetics, Inc. 700 East El Camino Real, Mountain View, California 94040, U.S.A. pp. (1–6)–(1–19) and (2–9)–(2–14).

Science, vol. 252, issued Jun. 21, 1991, M.D. Adams et al., "Complementary DNA sequencing: Expressed sequence tags and human genome project", pp. 1651–1656, see entire document.

Nature Genetics, vol. 2, No. 3, issued Nov. 1992, K. Okubo et al. "Large scale cDNA sequencing for analysis of quantitative and qualitative aspects of gene expression", pp. 173–179, see narrative text portion of entire document.

Hara, Eiji et al. "Subtractive cDNA cloning using oligo(dT)$_{30}$–latex and PCR: isolation of cDNA clones specific to undifferentiated human embryonal carcinoma cells". *Nucleic Acids Research,* vol. 19, No. 25.: 7097–7104 (1991).

Rubenstein, John L.R. et al. "Substractive hybridization system using single–stranded phagemids with directional inserts". *Nucleic Acids Research,* vol. 18, No. 16.: 4833–4842 (1990).

Rhyner, Thomas A. et al. "Molecular Cloning of Forebrain mRNAs which are Modulated by Sleep Deprivation". *European Journal of Neuroscience.* vol. 2: 1063–1073 (1990).

Fargnoli, Joseph et al. "Low–Ratio Hybridization Subtraction". *Analytical Biochemistry* 187: 364–372 (1990).

Schweinfest, Clfford W. et al. "Subtraction Hybridization cDNA Libraries From Colon Carcinoma and Hepatic Cancer". *Genet Annal Techn Appl* 7: 64–70 (1990).

Travis, Gabriel H. et al. "Pheno emulsion–enhanced DNA–driven subtractive cDNA cloning: Isolation of low–abundance monkey cortex–specific mRNAs". *Proceedings of the National Academy of Sciences, USA.* vol. 85: 1696–1700 (1988).

Batra, Surinder K. et al. "A Simple, Effective method for the Construction of Subtracted cDNA Libraries". *GATA* 8(4):129–133 (1991).

Swaroop, Anand et al. "A simple and efficient cDNA library subtraction procedure: isolation of human retina–specific cDNA clones". *Nucleic Acids Research* vol. 19, No. 8: 1954 (1991).

Patanjali, Sankhavaram R. "Construction of a uniform–abundance (normalized) cDNA library". *Proceedings National Academy Sciences, USA,* vol. 88: 1943–1947 (1991).

Hoog, Christer. "Isolation of a large number of novel mammalian genes by a differential cDNA library screening strategy". *Nucleic Acids Research,* vol. 19, No. 22: 6123–6127 (1991).

Duguid, John R. "Isolation of cDNAs of scrapie–modulated RNAs by subtractive hybridization of a cDNA library". *Proceedings of the National Academy of Sciences, USA,* vol. 85: 5738–2742. (1988).

Duguid, John R. et al. "Library subtraction of in vitro cDNA libraries to identify differentially expressed genes in scrapie infection". *Nucleic Acids Research,* vol. 18, No. 9: 2789–2792 (1989).

(List continued on next page.)

*Primary Examiner*—James Martinell
*Attorney, Agent, or Firm*—Carol L. Francis; Bozicevic, Field & Francis LLP

[57] ABSTRACT

A method and system for quantifying the relative abundance of gene transcripts in a biological sample. One embodiment of the method generates high-throughput sequence-specific analysis of multiple RNAs or their corresponding cDNAs (gene transcript imaging analysis). Another embodiment of the method produces a gene transcript imaging analysis by the use of high-throughput CDNA sequence analysis. In addition, the gene transcript imaging can be used to detect or diagnose a particular biological state, disease, or condition which is correlated to the relative abundance of gene transcripts in a given cell or population of cells. The invention provides a method for comparing the gene transcript image analysis from two or more different biological samples in order to distinguish between the two samples and identify one or more genes which are differentially expressed between the two samples.

17 Claims, 3 Drawing Sheets

OTHER PUBLICATIONS

Sive, Hazel L. et al. "A simple subtractive hybridization technique employing photoactivatable biotin and phenol extraction". *Nucleic Acids Research,* vol. 16 No. 22: 10937 (1988).

Date, C.J., 1990, "Introduction to Database Systems," Fifth Edition, Addison–Wesley Publishing Company, Reading, MA, pp. 22–25, 42–45, and 111–117.

Davison, D., (ed.), "Introduction to Molecular Biology Information Servers," *SIGBIO Newsletter,* May 1991, vol. 11, No. 1 and 2, pp. 1–6.

Frenkel, K.A., Nov. 1991, "The Human Genome Project and Informatics: A Monumental Scientific Adventure," *Communications of the ACM,* 34(11) pp. 40–52.

Frickett, J.W., et al., "Development of a Database for Nucleotide Sequences," in: *Mathematical Methods for DNA Sequences,* M.S. Waterman (ed.), CRC Press, Florida, 1989, pp. 1–34.

Khan, A.S., et al., 1992, "Single Pass Sequencing and Physical and Genetic Mapping of Human Brain cDNAs," *Nature Genetics* 2:180–5.

Matsubara, K., et al., 1993, "Identification of New Genes by Systemic Analysis of cDNAs and Database Construction," *Current Biology Ltd.,* 4 pp. 672–677.

Chenchik, et al, "Application of poly(A)+RNA Patterns Method Searching of Differentially Expressed Genes," *Febs. Letters,* 324(2):136–139 (Jun. 1993).

Hara, et al., "DNA–DNA Subtractive CDNA Cloning Using Oligo (DT) 30–Latex and PCR: Identification of Cellular Genes which are Overexpressed in Senescent Human Diploid Fibroblasts," *Analytical Biochemistry,* 214(1):58–64 (Oct. 1, 1993).

Ritter, et al., "Prototype Implementation of the Integrated Genomic Database," *Computers and Biomedical Research,* 27:97–115 (Apr. 1994).

COMPARATIVE GENE TRANSCRIPT ANALYSIS

CROSS-REFERENCE TO RELATED APPLICATIONS

This is a continuation-in-part of U.S. patent application Ser. No. 08/187,530, filed Jan. 27, 1994, now U.S. Pat. No. 5,840,484 which is a continuation-in-part application of U.S. patent applications Ser. Nos. 08/179,873 filed Jan. 11, 1994, now abandoned 08/137,951 filed Oct. 14, 1993, now abandoned and 08/100,523 filed Aug. 3, 1993, now abandoned which is a continuation-in-part application of U.S. patent application Ser. No. 07/977,780 filed Nov. 19, 1992, now abandoned which is a continuation-in-part application of U.S. patent application Ser. No. 07/916,491 filed Jul. 17, 1992, now abandoned.

1. FIELD OF INVENTION

The present invention is in the field of molecular biology and computer science; more particularly, the present invention describes methods of analyzing gene transcripts and diagnosing the genetic expression of cells and tissue.

2. BACKGROUND OF THE INVENTION

Nucleic acids (DNA and RNA) carry within their sequence the hereditary information and are therefore the prime molecules of life. Nucleic acids are found in all living organisms including bacteria, fungi, viruses, plants and animals. It is of interest to determine the relative abundance of nucleic acids in different cells, tissues and organisms over time under various conditions, treatments and regimes.

All dividing cells in the human body contain the same set of 23 pairs of chromosomes. It is estimated that the 22 autosomal and the sex chromosomes encode approximately 100,000 genes. The differences among different types of cells are believed to reflect the differential expression of the 100,000 or so genes. Fundamental questions of biology could be answered by understanding which genes are transcribed and what the relative abundance of transcripts in different cells.

Previously, the art has only provided for the analysis of a few known genes at a time by standard molecular biology techniques such as PCR, northern blot analysis, or other types of DNA probe analysis such as in situ hybridization. Each of these methods allows one to analyze the transcription of only known genes and/or small numbers of genes at a time. Nucl. Acids Res. 19, 7097–7104 (1991); Nucl. Acids Res. 18, 4833–4842 (1990); Nucl. Acids Res. 18, 2789–2792 (1989); European J. Neuroscience 2, 1063–1073 (1990); Analytical Biochem. 187, 364–373 (1990); Genet. Annal Techn. Appl. 7, 64–70 (1990); GATA 8(4), 129–133 (1991); Proc. Natl. Acad. Sci. USA 85, 1696–1700 (1988); Nucl. Acids Res. 19, 1954 (1991); Proc. Natl. Acad. Sci. USA 88, 1943–1947 (1991); Nucl. Acids Res. 19, 6123–6127 (1991); Proc. Natl. Acad. Sci. USA 85, 5738–5742 (1988); Nucl. Acids Res. 16, 10937 (1988).

Studies of the number and types of genes whose transcription is induced or otherwise regulated during cell processes such as activation, differentiation, aging, viral transformation, morphogenesis, and mitosis have been pursued for many years, using a variety of methodologies. One of the earliest methods was to isolate and analyze levels of the proteins in a cell, tissue, organ system, or even organism both before and after to the process of interest. One method of analyzing multiple proteins in a sample is using 2-dimensional gel electrophoresis, wherein proteins can be, in principle, identified and quantified as individual bands, and ultimately reduced to a discrete signal. In order to positively analyze each band, each band must be excised from the membrane and subjected to protein sequence analysis using Edman degradation. Unfortunately, most of the bands were present in quantities too small to obtain a reliable sequence, and many of those bands contained more than one discrete protein. An additional difficulty is that many of the proteins were blocked at the amino-terminus, further complicating the sequencing process.

Analyzing differentiation at the gene transcription level has overcome many of these disadvantages and drawbacks, since the power of recombinant DNA technology allows amplification of signals containing very small amounts of material. The most common method, called "hybridization subtraction", involves isolation of mRNA from the biological sample before (B) and after (A) the developmental process of interest, transcribing one set of mRNA into cDNA, subtracting sample B from sample A (mRNA from cDNA) by hybridization, and constructing a cDNA library from the non-hybridizing mRNA fraction. Many different groups have used this strategy successfully, and a variety of procedures have been published and improved upon using this same basic scheme (Nucl. Acids Res. 19, 7097–7104 (1991); Nucl. Acids Res. 18, 4833–4842 (1990); Nucl. Acids Res. 18, 2789–2792 (1989); European J. Neuroscience 2, 1063–1073 (1990); Analytical Biochem. 187, 364–373 (1990); Genet. Annal Techn. Appl. 7, 64–70 (1990); GATA 8(4), 129–133 (1991); Proc. Natl. Acad. Sci. USA 85, 1696–1700 (1988); Nucl. Acids Res. 19, 1954 (1991); Proc. Natl. Acad. Sci. USA 88, 1943–1947 (1991); Nucl. Acids Res. 19, 6123–6127 (1991); Proc. Natl. Acad. Sci. USA 85, 5738–5742 (1988); Nucl. Acids Res. 16, 10937 (1988).

All of these techniques have particular strengths and weaknesses; however, there are still some limitations and undesirable aspects of these methods: First, the time and effort required to construct such libraries is quite large. Typically, a trained molecular biologist might expect construction and characterization of such a library to require 3 to 6 months, depending on the level of skill, experience, and luck. Second, the resulting subtraction libraries are typically inferior to the libraries constructed by standard methodology. A typical conventional cDNA library should have a clone complexity of at least $10^6$ clones, and an average insert size of 1–3 kB. In contrast, subtracted libraries can have complexities of $10^2$ or $10^3$ and average insert sizes of 0.2 kBp. Therefore, there can be a significant loss of clone and sequence information associated with such libraries. Third, this approach allows the researcher to capture only the genes induced in sample A relative to sample B; not vice-versa, nor does it easily allow comparison to a third sample of interest (C). Fourth, this approach requires very large amounts (hundreds of micrograms) of "driver" mRNA (sample A), which significantly limits the number and type of subtractions that are possible since many tissues and cells are very difficult to obtain in large quantities.

Fifth, the resolution of the subtraction is dependent upon the physical properties of DNA:DNA or RNA:DNA hybridization. The ability of a given sequence to find a hybridization match is dependent on its unique CoT value. The CoT value is a function of the number of copies (concentration) of the particular sequence, multiplied by the time of hybridization. It follows that for sequences which are abundant, hybridization events will occur very rapidly (low CoT value), while rare sequences will form duplexes at very high CoT values. Unfortunately, the rare genes, or those present at abundances of $10^{-4}$–$10^{-7}$ and those in which an investigator would likely be most interested, are lost. CoT values which allow such rare sequences to form duplexes are difficult to achieve in a convenient time frame. Therefore, hybridization subtraction is simply not a useful technique with which to study relative levels of rare mRNA species. Sixth, this problem is further complicated by the fact that duplex formation is also dependent on the nucleotide base composition for a given sequence. Those sequences rich in G+C form stronger duplexes than those with high contents of A+T. Therefore, the former sequences will tend to be removed selectively by hybridization subtraction. Seventh, it is possible that hybridization between nonexact matches can occur. When this happens, the expression of a homologous gene may "mask" expression of a gene of interest, artificially skewing the results for that particular gene.

Matsubara and Okubo proposed using partial cDNA sequences to establish expression profiles of genes which could be used in functional analyses of the human genome. Matsubara and Okubo warned against using random priming, as it creates multiple unique DNA fragments from individual mRNAs and may thus skew the analysis of the number of particular mRNAs per library. They sequenced randomly selected members from a 3'-directed cDNA library and established the frequency of appearance of the various ESTs. They proposed comparing lists of ESTs from various cell types to classify genes. Genes expressed in many different cell types were labeled housekeepers and those selectively expressed in certain cells were labeled cell-specific genes, even in the absence of the full sequence of the gene or the biological activity of the gene product.

The present invention avoids the drawbacks of the prior art by providing a method to quantify the relative abundance of multiple gene transcripts in a given biological sample by the use of high-throughput sequence-specific analysis of individual RNAs and/or their corresponding cDNAs.

The present invention offers several advantages over current protein discovery methods which attempt to isolate individual proteins based upon biological effects. The method of the instant invention provides for detailed diagnostic comparisons of cell profiles revealing numerous changes in the expression of individual transcripts.

The instant invention provides several advantages over previous subtraction methods including a more complex library analysis ($10^6$ to $10^7$ clones as compared to $10^3$ clones) which allows identification of low abundance messages as well as enabling the identification of messages which either increase or decrease in abundance. These large libraries are very routine to make in contrast to the libraries of previous methods. In addition, homologues can easily be distinguished with the method of the instant invention.

This method is very convenient because it organizes a large quantity of data into a comprehensible, digestable format. The most significant differences are highlighted by electronic subtraction. In depth analyses are made more convenient.

The present invention provides several advantages over previous methods of electronic analysis of cDNA. The method is particularly powerful when more than 100 and preferably more than 1,000 gene transcripts are analyzed. In such a case, new low-frequency transcripts are discovered and tissue tipped.

High resolution analysis of gene expression can be used directly as a diagnostic profile or to identify disease-specific genes for the development of more classic diagnostic approaches.

This process is defined as gene transcript frequency analysis. The resulting quantitative analysis of the gene transcripts is defined as comparative gene transcript analysis.

3. SUMMARY OF THE INVENTION

The invention is a method of analyzing a library of polynucleotide sequences comprising the steps of (a) producing a library of gene transcripts; (b) generating a set of transcript sequences, where each of the transcript sequence in said set is indicative of a different one of the biological sequences of the library; (c) processing the transcript sequence in a programmed computer in which a database of reference transcript sequence indicative of reference sequences is stored, to generate an identified sequence value for each of the transcript sequences, where each said identified sequence value is indicative of a degree of match between a different one of the biological sequences of the library and at least one of the reference sequences; and (d) processing each said identified sequence value to generate final data values indicative of the number of matches between the biological sequences of the library and ones of the reference sequences.

In a further embodiment, the method includes producing a gene transcript image analysis, by (a) isolating an mRNA population from a biological sample; (b) identifying genes from which the mRNA was transcribed by a sequence-specific method; (c) determining the numbers of mRNA transcripts corresponding to each of the genes; and (d) using the mRNA transcript numbers to determine the relative abundance of mRNA transcripts within the population of mRNA transcripts, where data determining the relative abundance values of mRNA transcripts is the gene transcript image analysis.

In a further embodiment, the relative abundance of the gene transcripts in one cell type or tissue is compared with the relative abundance of gene transcript numbers in a second cell type or tissue in order to identify the differences and similarities.

In a further embodiment, the method includes a system for analyzing a library of biological sequences including a means for receiving a set of transcript sequences, where each of the transcript sequence is indicative of a different one of the biological sequences of the library; and a means for processing the transcript sequence in a computer system in which a database of reference transcript sequence indicative of reference sequences is stored, wherein the computer is programmed with software for generating an identified sequence value for each of the transcript sequences, where each said identified sequence value is indicative of a degree of match between a different one of the biological sequences of the library and at least one of the reference sequences, and for processing each said identified sequence value to generate final data value indicative of number of matches between the biological sequences of the library and ones of the reference sequences.

In a further embodiment, a first value of the degree of match is indicative of an "exact" match, and a second value of said degree of match is indicative of a lesser degree of match.

In essence, the invention is a method and system for quantifying the relative abundance of gene transcripts in a biological sample. The invention provides a method for comparing the gene transcript image from two or more different biological samples in order to distinguish between the two samples and identify one or more genes which are differentially expressed between the two samples. Thus, this gene transcript image and its comparison can be used as a diagnostic. One embodiment of the method generates high-throughput sequence-specific analysis of multiple RNAs or their corresponding cDNAs: a gene transcript image. Another embodiment of the method produces the gene transcript imaging analysis by the use of high-throughput cDNA sequence analysis. In addition, two or more gene transcript images can be compared and used to detect or diagnose a particular biological state, disease, or condition which is correlated to the relative abundance of gene transcripts in a given cell or population of cells.

In a class of embodiments, the invention incorporates a method for producing a set ("library") of oligo or polynucleotide sequences. Polynucleotide sequences herein defined include DNA and RNA. The method includes generating a set of transcript sequence, each of the transcript sequence indicative of a different one of the polynucleotide sequences of the library; processing the transcript sequence in a programmed computer, in which a database of reference transcript sequence (indicative of reference sequences) is stored, to identify each sequence (i.e., generate an identified sequence value for each of the transcript sequences, where each identified sequence value is indicative of a degree of match between a different one of the polynucleotide sequences of the library and at least one of the reference sequences); and processing the identified sequence values to generate final data value (typically, a sorted list of identified sequences and corresponding abundance values) indicative of the number of matches between the sequences of the library and ones of the reference sequences.

4. DESCRIPTION OF THE TABLES AND DRAWINGS

4.1. TABLES

Table 1 presents a detailed explanation of the letter codes utilized in Tables 2–5.

Table 2 is a list of isolates from the HUVEC cDNA library arranged according to abundance from U.S. patent application Ser. No. 08/137,951 filed Oct. 14, 1993 which is hereby incorporated by reference. The left-hand column labeled "number" refers to the sequences order of abundance in this table. The next column is the clone number of the first HUVEC sequence identification reference matching the sequence in the "entry" column number. Isolates that have not been sequenced are not present in the Sequence Listing or Table 2. The next column, labeled "N", indicates the total number of cDNA's which have the same degree of match with the sequence of the reference transcript in the "entry column".

The column labeled "l" refers to the library from which the cDNA clone was isolated: "H" for HUVEC cells. The column labeled "d" (an abbreviation for designation) contains a letter code indicating the degree of type of homology of the sequence. The letter code, as presented in Table 1, is as follows: N— no homology to previously identified nucleotide sequences in reference databases or Incyte's database, E— "exact" match to a previously identified nucleotide sequence which reflects at least 90% agreement of called bases for most of the Sequence length, U— the sequence of the isolate has not been determined, (ordinarily not included in this table), M— mitochondrial DNA sequence, O— homologous to a non-human sequence but less homologous than "E", H-homologous to a human sequence but less homologous than an E sequence; R— Repetitive DNA sequence, V— vector sequence only; S— sequence not yet determined; I— matches an Incyte clone (part of an assemblage); X— matches an EST; and A— a poly A sequence. The column labeled "f" refers to the distribution of the gene product encoded by the cDNA. The letter code as presented in Table 1 is as follows: C-non-specific, P-cell/tissue specific and U-unknown.

The column labeled "z" refers to the cellular localization of the gene product encoded by the cDNA. The letter code is given in Table 1.

The column labeled "r" refers to function of the gene product encoded by the cDNA. The letter code for the "r" column is presented in Table 1.

The column labeled "c" refers to the certainty of the identification of the clone. There is an entry in the "c" column only if there is some uncertainty about the relationship of the sequence with the reference sequence.

The column labeled "entry" gives the NIH GENBANK locus name, identifying sequence is a nucleotide sequence corresponding to the library sequence numbers. The "s" column indicates in a few cases the species of the reference sequence. The code for column "s" is given in Table 1. The column labeled "descriptor" provides a plain English explanation of the identity of the sequence corresponding to the NIH GENBANK locus name in the "entry" column. The "descriptor" column also indicates when unreadable sequence was present or when templates were skipped.

The "init" column indicates the position in the reference sequence where the first library sequence started. In this column, "0" corresponds to the beginning of the coding region of the mature protein. Negative numbers indicate that the library sequence began in the signal sequence of the reference protein. Positive numbers indicate that the library sequence began in the coding region or in the 5" end.

The column "i" is a working column used to indicate whether more work has been done or is planned for particular sequences. The "i" code is given in Table 1.

Table 3 is a comparison of the top 15 most abundant gene transcripts in normal monocytes and activated macrophage cells.

Table 4 is a detailed library subtraction analysis summary comparing all of the THP-1 and human macrophage cDNA sequences. In Table 4, most of the same code as Table 2 is used. Additional columns are for "bgfreq" (abundance number in the subtractant library), "rfend" (abundance number in the target library) and "ratio" (dividend of the target abundance number divided by the subtractant abundance number). As is clear from perusal of the table, when the abundance number in the subtractant library is "0", the target abundance number is divided by 0.5. This is a way of obtaining a result (not possible dividing by 0) and distinguishing the result from ratios of subtractant numbers of 1.

Table 5 is the computer program, writtenin source code, for generating gene transcript subtraction profiles.

4.2. BRIEF DESCRIPTION OF THE DRAWINGS

5. DETAILED DESCRIPTION OF THE INVENTION

Figure 1:
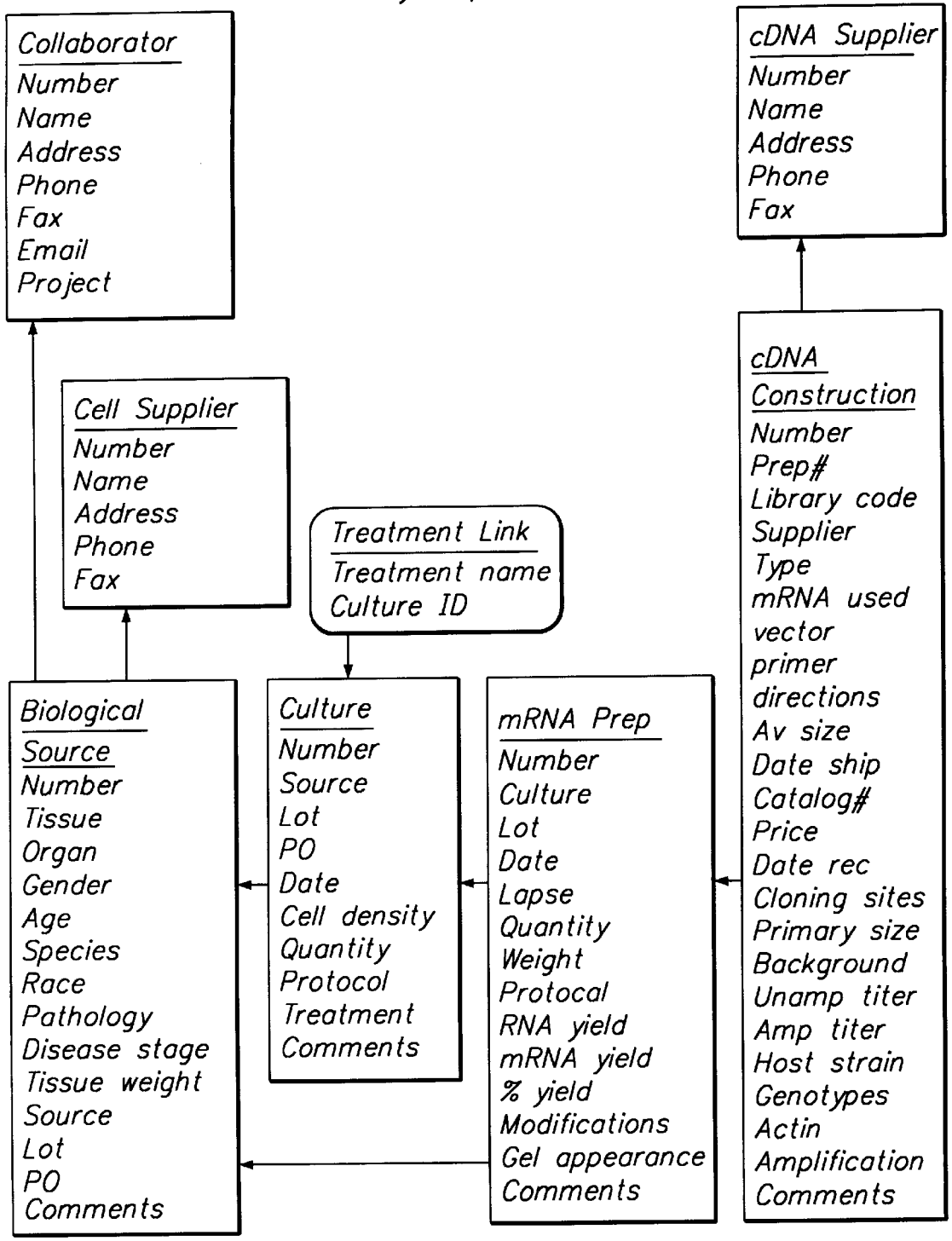
FIG. 1 is a chart summarizing data collected and stored regarding the library construction portion of sequence preparation and analysis.

The present invention provides a method to compare the relative abundance of gene transcripts in different biological samples by the use of high-throughput sequence-specific analysis of individual RNAs or their corresponding cDNAs (or alternatively, of data representing other biological sequences). This process is denoted herein as gene transcript imaging. The quantitative analysis of the relative abundance for a set of gene transcripts is denoted herein as "gene transcript image analysis" or "gene transcript frequency analysis". The present invention allows one to obtain a profile for gene transcription in any given population of cells or tissue from any type of organism. The invention can be applied to obtain a profile of a sample consisting of a single cell (or clones of a single cell), or of many cells, or of tissue more complex than a single cell and containing multiple cell types, such as liver.

The invention has significant advantages in the fields of diagnostics, toxicology and pharmacology, to name a few. A highly sophisticated diagnostic test can be performed on the ill patient in whom a diagnosis has not been made. The patient's sample is obtained, the gene transcripts are isolated and expanded to the extent necessary to determine their identity. Optionally, the gene transcripts can be converted to cDNA. A sample of the gene transcripts are subjected to sequence-specific analysis and quantified. These gene transcript sequences are compared against a reference database sequences including normal data for diseased and healthy patients. The patient has the disease(s) with which the patient's data set most closely correlates.

For example, gene transcript frequency analysis can be used to differentiate normal cells or tissue from diseased cells or tissues or activated macrophages from non-activated macrophages.

In toxicology, a major question is which tests are most effective in predicting or reporting a toxic effect. Gene transcript imaging provides highly detailed information on cell and tissue environment, some of which may not be obvious in normal, less detailed screening methods. The gene transcript image is a more powerful method to predict drug toxicity and efficacy. Similar benefits accrue in the use of this tool in pharmacology.

In an alternative embodiment, comparative gene transcript frequency analysis is used to differentiate between cancer cells which respond to anti-cancer agents and those which do not respond. Potential anti-cancer agents include tamoxifen, vincristine, vinblastine, podophyllotoxins, etoposide, tenisposide, cisplatin, biologic response modifiers such as interferon, Il-2, GM-CSF, enzymes, hormones and the like.

In yet another embodiment, comparative gene transcript frequency analysis is used to differentiate between liver cells isolated from patients treated and untreated with FIAU to distinguish between pathology caused by the underlying disease and that caused by the drug.

In yet another embodiment, comparative gene transcript frequency analysis is used to differentiate between brain tissue from patients treated and untreated with lithium.

In a further embodiment, comparative gene transcript frequency analysis is used to differentiate between cyclosporin and FK506-treated cells and normal cells.

In a further embodiment, comparative gene transcript frequency analysis is used to differentiate between viral infected, including HIV, human cells and uninfected human cells. Gene transcript frequency analysis is also used to compare HIV-resistant cells to HIV-infected or HIV-sensitive cells.

In a further embodiment, comparative gene transcript frequency analysis is used to differentiate between bronchial lavage fluids from healthy and unhealthy patients with a variety of ailments.

In a further embodiment, comparative gene transcript frequency analysis is used to differentiate between cell, plant, microbial and animal mutants and wild-type species. Such mutants could be deletion mutants which do not produce a gene product and/or point mutants which produce a less abundant or otherwise slightly different message. Such mutations can affect mineral nutrition, metabolism, biochemical and pharmacological processes and can be isolated by means known to those skilled in the art.

In a further embodiment, comparative gene transcript frequency analysis is used for an interspecies comparative analysis which would allow for the selection of better animal models. In this embodiment, human and animal (such as a mouse) cells are treated with a specific test agent. The relative sequence abundance of each cDNA population is determined. If the animal test system is a good model, homologous genes in the animal cDNA population should change expression similarly to those in human cells. If side effects are detected with the drug, a detailed transcript abundance analysis will be performed. Models will then be selected by these basic physiological changes.

In a further embodiment, comparative gene transcript frequency analysis is used in a clinical setting to give a highly detailed gene transcript profile of a patient's cells or tissue (for example, a blood sample). In particular, gene transcript frequency analysis is used to give a high resolution gene expression profile of a diseased state or condition.

In the preferred embodiment, the method utilizes high-throughput cDNA sequencing to identify specific transcripts of interest. The generated cDNA and deduced amino acid sequences are then extensively compared with GENBANK and other sequence data banks as described below. The method offers several advantages over current protein discovery by two-dimensional gel methods which try to identify individual proteins involved in a particular biological effect. Here, detailed comparisons of profiles of activated and inactive cells reveal numerous changes in the expression of individual transcripts. After it is determined if the sequence is an exact match, similar or entirely dissimilar, the sequence is entered into a database. Next, the numbers of copies of cDNA corresponding to particular genes are tabulated. Although this can be done slowly and arduously, if at all by human hand from a printout of all entries, a computer program is a useful way to tabulate this information. The numbers of copies (optionally divided by the total number of sequences in the data set) provides a picture of the relative abundance of transcripts for each corresponding gene. The list of represented genes can then be sorted by abundance in the cDNA population. A multitude of additional types of comparisons or dimensions are possible and described below in detail.

An alternate method of producing a gene transcript image includes the steps of obtaining a mixture of test mRNA and providing a representative array of unique probes whose sequences are complementary to at least some of the test mRNAs. Next, a fixed amount of the test mRNA is added to the arrayed probes. The test mRNA is incubated with the probes for a sufficient time to allow hybrids of the test mRNA and probes to form. The mRNA-probe hybrids are detected and the quantity determined. The hybrids are identified by their location in the probe array. The quantity of each hybrid is summed to give a population number. Each hybrid quantity is divided by the population number to provide a set of relative abundance data termed a gene transcript image analysis.

The method also provides for the use of a set of partial or complete sequences as probes to identify and quantify gene transcripts. The larger variety of the probes, the more complete and detailed gene transcript image.

6. EXAMPLES

The examples below are provided to illustrate the subject invention. These examples are provided by way of illustration and are not included for the purpose of limiting the invention.

6.1. CONSTRUCTION OF cDNA LIBRARIES

For inter-library comparisons, the libraries must be prepared in similar manners. Certain parameters appear to be particularly important to control. One such parameter is the method of isolating mRNA. It is important to use the same conditions to remove DNA and heterogeneous nuclear RNA from comparison libraries. Size fractionation of cDNA must be carefully controlled. The same vector preferably should be used for preparing libraries to be compared. At the very least, the same type of vector (e.g., unidirectional vector) should be used to assure a valid comparison. A unidirectional vector may be preferred because it is easier to analyze the output. However, with a unidirectional vector, there is dropout from the wrong-direction ligations.

It is preferred to prime only with oligo dT unidirectional primer in order to obtain one only clone per mRNA transcript when obtaining cDNAs. However, it is recognized that employing a mixture of dT and random primers can also be advantageous because such a mixture affords more freedom when gene discovery also is a goal. Similar effects can be obtained with DR2 (Clontech) and HXLOX (US Biochemical) and also vectors from Invitrogen and Novagen. These vectors have two requirements. First, there must be primer sites for commercially available primers such as T3 or M13 reverse primers. Second, the vector must accept inserts up to 10 kb.

It also is important that the clones be randomly sampled, and that a significant population of clones is used. Data has been generated with 5,000 clones; however, if very rare genes are to be obtained and/or their relative abundance determined, as many as 100,000 clones may need to be sampled. Size fractionation of cDNA must be carefully controlled.

Besides the Uni-ZAP TM vector system by Stratagene disclosed in the examples, it is now believed that other similarly unidirectional vectors also can be used. For example, it is believed that such vectors include but are not limited to DR2 (Clontech), and HXLOX (U.S. Biochemical).

Preferably, the details of library construction (as shown in FIG. 1) are collected and stored in a database for later retrieval against the sequences being compared. FIG. 1 shows important information regarding the library collaborator or cell or cDNA supplier, pretreatment, biological source, culture, mRNA preparation and cDNA construction. Similarly detailed information about the other steps is beneficial in analyzing sequences and libraries in depth.

6.2. ISOLATION OF CDNA CLONES

The phagemid forms of individual cDNA clones were obtained by the in vivo excision process, in which the host bacterial strain was coinfected with both the lambda library phage and an f1 helper phage. Proteins derived from both the library-containing phage and the helper phage nicked the lambda DNA, initiated new DNA synthesis from defined sequences on the lambda target DNA and created a smaller, single stranded circular phagemid DNA molecule that included all DNA sequences of the pBluescript® plasmid and the cDNA insert. The phagemid DNA was secreted from the cells and purified, then used to re-infect fresh host cells, where the double stranded phagemid DNA was produced. Because the phagemid carries the gene for B-lactamase, the newly-transformed bacteria are selected on medium containing ampicillin.

Phagemid DNA was purified using the Magic Minipreps' DNA Purification System (Promega catalogue #A7100. Promega Corp., 2800 Woods Hollow Rd., Madison, Wis. 53711). This small-scale process provides a simple and reliable method for lysing the bacterial cells and rapidly isolating purified phagemid DNA using a proprietary DNA-binding resin. The DNA was eluted from the purification resin already prepared for DNA sequencing and other analytical manipulations.

Phagemid DNA was also purified using the QIAwell-8 Plasmid Purification System from QIAGEN® DNA Purification System (QIAGEN Inc., 9259 Eton Ave., Chattsworth, Calif. 91311). This product line provides a convenient, rapid and reliable high-throughput method for lysing the bacterial cells and isolating highly purified phagemid DNA using QIAGEN anion-exchange resin particles with EMPORE™ membrane technology from 3M in a multiwell format. The DNA was eluted from the purification resin already prepared for DNA sequencing and other analytical manipulations.

6.3. SEQUENCING OF cDNA CLONES

The cDNA inserts from random isolates of the U-937 and THP-1 libraries were sequenced in part. Methods for DNA sequencing are well known in the art. Conventional enzymatic methods employ DNA polymerase Klenow fragment, Sequenase™ or Taq polymerase to extend DNA chains from an oligonucleotide primer annealed to the DNA template of interest. Methods have been developed for the use of both single- and double stranded templates. The chain termination reaction products are usually electrophoresed on urea-acrylamide gels and are detected either by autoradiography (for radionuclide-labeled precursors) or by fluorescence (for fluorescent-labeled precursors). Recent improvements in mechanized reaction preparation, sequencing and analysis using the fluorescent detection method have permitted expansion in the number of sequences that can be determined per day (such as the Applied Biosystems 373 DNA sequencer and Catalyst 800). Currently with the system as described, read lengths range from 250 to 400 bases and are clone dependent. Read length also varies with the length of time the gel is run. The shorter runs tend to truncate the sequence. Gene transcript imaging can be used with any sequence-specific method, including, but not limited to hybridization, mass spectroscopy, capillary electrophoresis and 505 gel electrophoresis.

6.4. HOMOLOGY SEARCHING OF CDNA CLONE AND DEDUCED PROTEIN (and Subsequent Steps)

Using the nucleotide sequences derived from the cDNA clones as query sequences (sequences of a Sequence Listing), databases containing previously identified sequences are searched for areas of homology (similarity). Examples of such databases include Genbank and EMBL. We next describe examples of two homology search algorithms that can be used, and then describe the subsequent computer-implemented steps to be performed in accordance with preferred embodiments of the invention.

In the following description of the computer-implemented steps of the invention, the word "library" denotes a set (or population) of biological sample nucleic acid sequences. A "library" can consist of cDNA sequences, RNA sequences, or the like, which characterize a biological sample. The biological sample can consist of cells of a single human cell type (or can be any of the other above-mentioned types of samples). We contemplate that the sequences in a library have been determined so as to accurately represent or characterize a biological sample (for example, they can consist of representative cDNA sequences from clones of a single human cell).

In the following description of the computer-implemented steps of the invention, the expression "database", denotes a set of stored data which represent a collection of sequences, which in turn represent a collection of biological reference materials. For example, a database can consist of data representing many stored cDNA sequences which are in turn representative of human cells infected with various viruses, human cells of various ages, cells from various species of mammals, and so on.

In preferred embodiments, the invention employs a computer programmed with software (to be described) for performing the following steps:

(a) processing data indicative of a library of cDNA sequences (generated as a result of high-throughput cDNA sequencing or other method) to determine whether each sequence in the library matches a cDNA sequence of a reference database of cDNA sequences (and if so, identifying the reference database entry which matches the sequence and indicating the degree of match between the reference sequence and the library sequence) and assigning an identified sequence value to each of the sequences in the library;

(b) for some or all entries of the database, tabulating the number of matching identified sequence values in the library (Although this can be done by human hand from a printout of all entries, we prefer to perform this step using computer software to be described below.), thereby generating a set of "abundance numbers"; and (c) if the libraries are different sizes, dividing each abundance number by the total number of sequences in the library, to obtain a relative abundance number for each identified sequence value (i.e., a relative abundance of each gene transcript).

The list of identified sequence values (or genes corresponding thereto) can then be sorted by abundance in the cDNA population. A multitude of additional types of comparisons or dimensions are possible.

For example (to be described below in greater detail), steps (a) and (b) can be repeated for two different libraries (sometimes referred to as a "target" library and a "subtractant" library). Then, for each identified sequence value (or gene transcript), a "ratio" value is obtained by dividing the abundance number (for that identified sequence value) for the target library, by the abundance number (for that identified sequence value) for the subtractant library.

Unlike standard hybridization technology which permits a single subtraction of two libraries, once one has processed a set or library transcript sequences and stored them in the computer, any number of subtractions can be performed on the library. For example, by this method, ratio values can be obtained by dividing relative abundance values in a first library by corresponding values in a second library and vice versa.

In variations on step (a), the library consists of nucleotide sequences derived from cDNA clones. Examples of databases which can be searched for areas of homology (similarity) in step (a) include the commercially available databases known as Genbank (NIH) EMBL (European Molecular Biology Labs, Germany), and GENESEQ (Intelligenetics, Mountain View, Calif.).

One homology search algorithm which can be used to implement step (a) is the algorithm described in the paper by D. J. Lipman and W. R. Pearson, entitled "Rapid and Sensitive Protein Similarity Searches", *Science,* 227, 1435 (1985). In this algorithm, the homologous regions are searched in a two-step manner. In the first step, the highest homologous regions are determined by calculating a matching score using a homology score table. The parameter "Ktup" is used in this step to establish the minimum window size to be shifted for comparing two sequences. Ktup also sets the number of bases that must match to extract the highest homologous region among the sequences. In this step, no insertions or deletions are applied and the homology is displayed as an initial (INIT) value.

In the second step, the homologous regions are aligned to obtain the highest matching score by inserting a gap in order to add a probable deleted portion. The matching score obtained in the first step is recalculated using the homology score Table and the insertion score Table to an optimized (OPT) value in the final output.

DNA homologies between two sequences can be examined graphically using the Harr method of constructing dot matrix homology plots (Needleman, S. B. and Wunsch, C. O., *J. Mol. Biol* 48:443 (1970)). This method produces a two-dimensional plot which can be useful in determining regions of homology versus regions of repetition.

However, in a class of preferred embodiments, step (a) is implemented by processing the library data in the commercially available computer program known as the INHERIT 670 Sequence Analysis System, available from Applied Biosystems Inc. (of Foster City, Calif.), including the software known as the Factura software (also available from Applied Biosystems Inc.). The Factura program preprocesses each library sequence to "edit out" portions thereof which are not likely to be of interest, such as the vector used to prepare the library. Additional sequences which can be edited out or masked (ignored by the search tools) include but are not limited to the polyA tail and repetitive GAG and CCC sequences. A low-end search program can be written to mask out such "low-information" sequences, or programs such as BLAST can ignore the low-information sequences.

In the algorithm implemented by the INHERIT 670 Sequence Analysis System, the Pattern Specification Language (developed by TRW Inc.) is used to determine regions of homology. "There are three parameters that determine how INHERIT analysis runs sequence comparisons: window size, window offset and error tolerance. Window size specifies the length of the segments into which the query sequence is subdivided. Window offset specifies where to start the next segment [to be compared], counting from the beginning of the previous segment. Error tolerance specifies the total number of insertions, deletions and/or substitutions that are tolerated over the specified word length. Error tolerance may be set to any integer between 0 and 6. The default settings are window tolerance=20, window offset=10 and error tolerance=3." *INHERIT Analysis Users Manual.* pp. 2–15. Version 1.0. Applied Biosystems, Inc. October, 1991. Using a combination of these three parameters, a database (such as a DNA database) can be searched for sequences containing regions of homology and the appropriate sequences are scored with an initial value. Subsequently, these homologous regions are examined using dot matrix homology plots to determine regions of homology versus regions of repetition. Smith-Waterman alignments can be used to display the results of the homology search. The INHERIT software can be executed by a Sun computer system programmed with the UNIX operating system.

Search alternatives to INHERIT include the BLAST program, GCG (available from the Genetics Computer Group, Wis.) and the Dasher program (Temple Smith, Boston University, Boston, Mass.). Nucleotide sequences can be searched against Genbank, EMBL or custom databases such as GENESEQ (available from Intelligenetics, Mountain View, Calif.) or other databases for genes. In addition, we have searched some sequences against our own inhouse database.

In preferred embodiments, the transcript sequences are analyzed by the INHERIT software for best conformance with a reference gene transcript to assign a sequence identifier and assigned the degree of homology, which together are the identified sequence value and are input into, and further processed by, a Macintosh personal computer (available from Apple) programmed with an "abundance sort and subtraction analysis" computer program (to be described below).

Prior to the abundance sort and subtraction analysis program (also denoted as the "abundance sort" program), identified sequences from the CDNA clones are assigned value (according to the parameters given above) by degree of match according to the following categories: "exact" matches (regions with a high degree of identity), homologous human matches (regions of high similarity, but not "exact" matches), homologous non-human matches (regions of high similarity present in species other than human), or non matches (no significant regions of homology to previously identified nucleotide sequences stored in the form of the database).

With reference again to the step of identifying matches between reference sequences and database entries, protein and peptide sequences can be deduced from the nucleic acid sequences. Using the deduced polypeptide sequence, the match identification can be performed in a manner analogous to that done with cDNA sequences. A protein sequence is used as a query sequence and compared to the previously identified sequences contained in a database such as the Swiss/Prot, PIR and the NBRF Protein database to find homologous proteins. These proteins are initially scored for homology using a homology score Table (Orcutt, B. C. and Dayoff, M. O. Scoring Matrices, PIR Report MAT—0285 (February 1985)) resulting in an INIT score. The homologous regions are aligned to obtain the highest matching scores by inserting a gap which adds a probable deleted portion. The matching score is recalculated using the homology score Table and the insertion score Table resulting in an optimized (OPT) score. Even in the absence of knowledge of the proper reading frame of an isolated sequence, the above-described protein homology search may be performed by searching all 3 reading frames.

Peptide and protein sequence homologies can also be ascertained using the INHERIT 670 Sequence Analysis System in an analogous way to that used in DNA sequence homologies. Pattern Specification Language and parameter windows are used to search protein databases for sequences containing regions of homology which are scored with an initial value. Subsequent display in a dot-matrix homology plot shows regions of homology versus regions of repetition. Additional search tools that are available to use on pattern search databases include PLsearch Blocks (available from Henifoff & Henikoff, University of Washington, Seattle), Dasher and GCG. Pattern search databases include, but are not limited to, Protein Blocks (available from Henifoff & Henikoff, University of Washington, Seattle), Brookhaven Protein (available from the Brookhaven National Laboratory, Brookhaven, Mass.), PROSITE (available from Amos Bairoch, University of Genera, Switzerland), ProDom (available from Temple Smith, Boston University), and PROTEIN MOTIF FINGERPRINT (available from University of Leeds, United Kingdom).

The ABI Assembler application software, part of the INHERIT DNA analysis system (available from Applied Biosystems, Inc., Foster City, Calif.), can be employed to create and manage sequence assembly projects by assembling data from selected sequence fragments into a larger sequence. The Assembler software combines two advanced computer technologies which maximize the ability to assemble sequenced DNA fragments into Assemblages, a special grouping of data where the relationships between sequences are shown by graphic overlap, alignment and statistical views. The process is based on the Meyers-Kececioglu model of fragment assembly (INHERIT™ Assembler User's Manual, Applied Biosystems, Inc., Foster City, Calif.), and uses graph theory as the foundation of a very rigorous multiple sequence alignment engine for assembling DNA sequence fragments. Other assembly programs that can be used include MEGALIGN (available from DNASTAR Inc., Madison, Wis.), Dasher and STADEN (available from Roger Staden, Cambridge, England).

Figure 2:
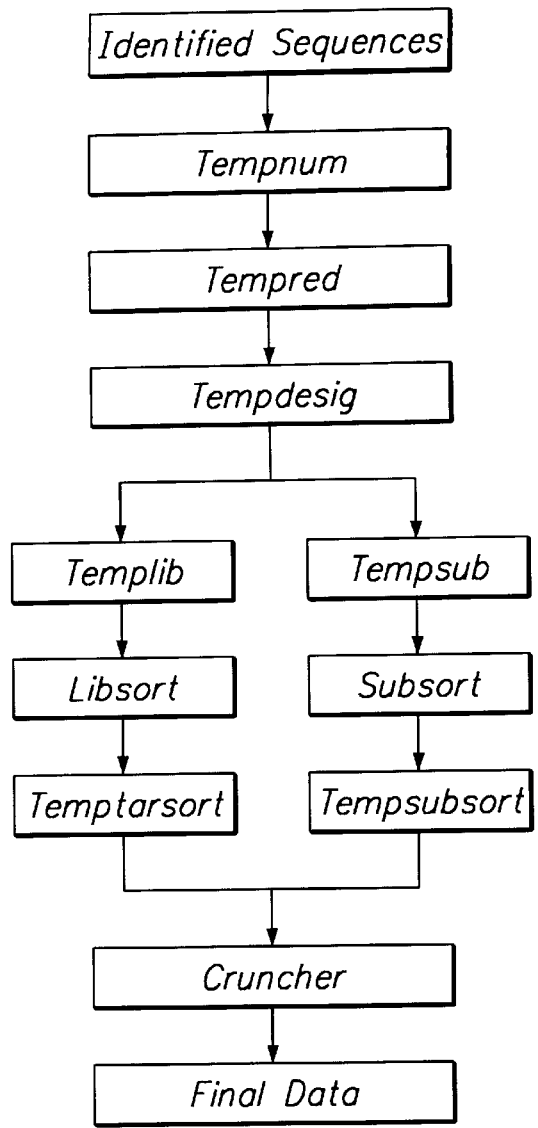
FIG. 2 is a diagram representing the sequence of operations performed by "abundance sort" software in a class of preferred embodiments of the inventive method.

Next, with reference to FIG. 2, we describe in more detail the "abundance sort" program which implements above-mentioned "step (b)" to tabulate the number of sequences of the library which match each database entry (the "abundance number" for each database entry).

FIG. 2 is a flow chart of a preferred embodiment of the abundance sort program. A source code listing of this embodiment of the abundance sort program is set forth below as Table 5. In Table 5 implementation, the abundance sort program is written using the FoxBASE programming language commercially available from Microsoft Corporation. The subroutine names specified in FIG. 2 correspond to subroutines listed in Table 5.

With reference again to FIG. 2, the "Identified Sequences" are transcript sequences representing each sequence of the library and a corresponding identification of the database entry (if any) which it matches. In other words, the "Identified Sequences" are transcript sequences representing the output of above-discussed "step (a)."

Figure 3:
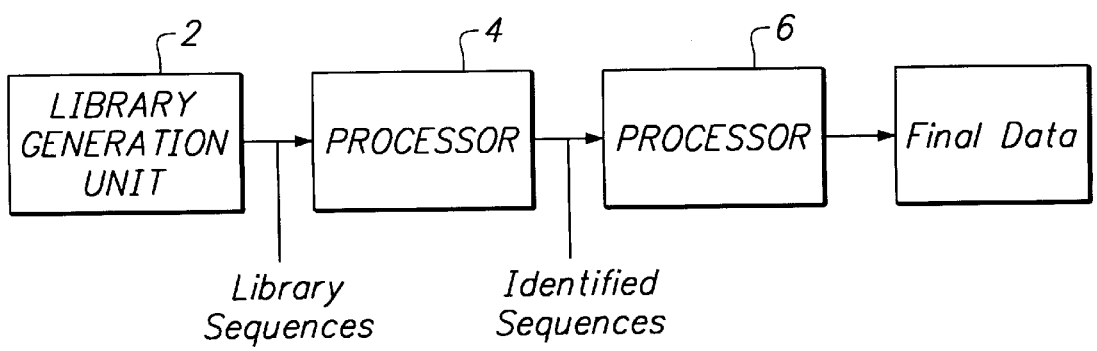
FIG. 3 is a block diagram of a preferred embodiment of the system of the invention.

FIG. 3 is a block diagram of a system for implementing the invention. The FIG. 3 system includes library generation unit 2 which generates a library and asserts an output stream of transcript sequences indicative of the sequences comprising the library. Programmed processor 4 receives the data stream output from unit 2 and processes this data in accordance with above-discussed "step (a)" to generate the Identified Sequences. Processor 4 can be a processor programmed with the commercially available computer program known as the INHERIT 670 Sequence Analysis System and the commercially available computer program known as the Factura program (both available from Applied Biosystems Inc.) and with the UNIX operating system.

Figure 4:
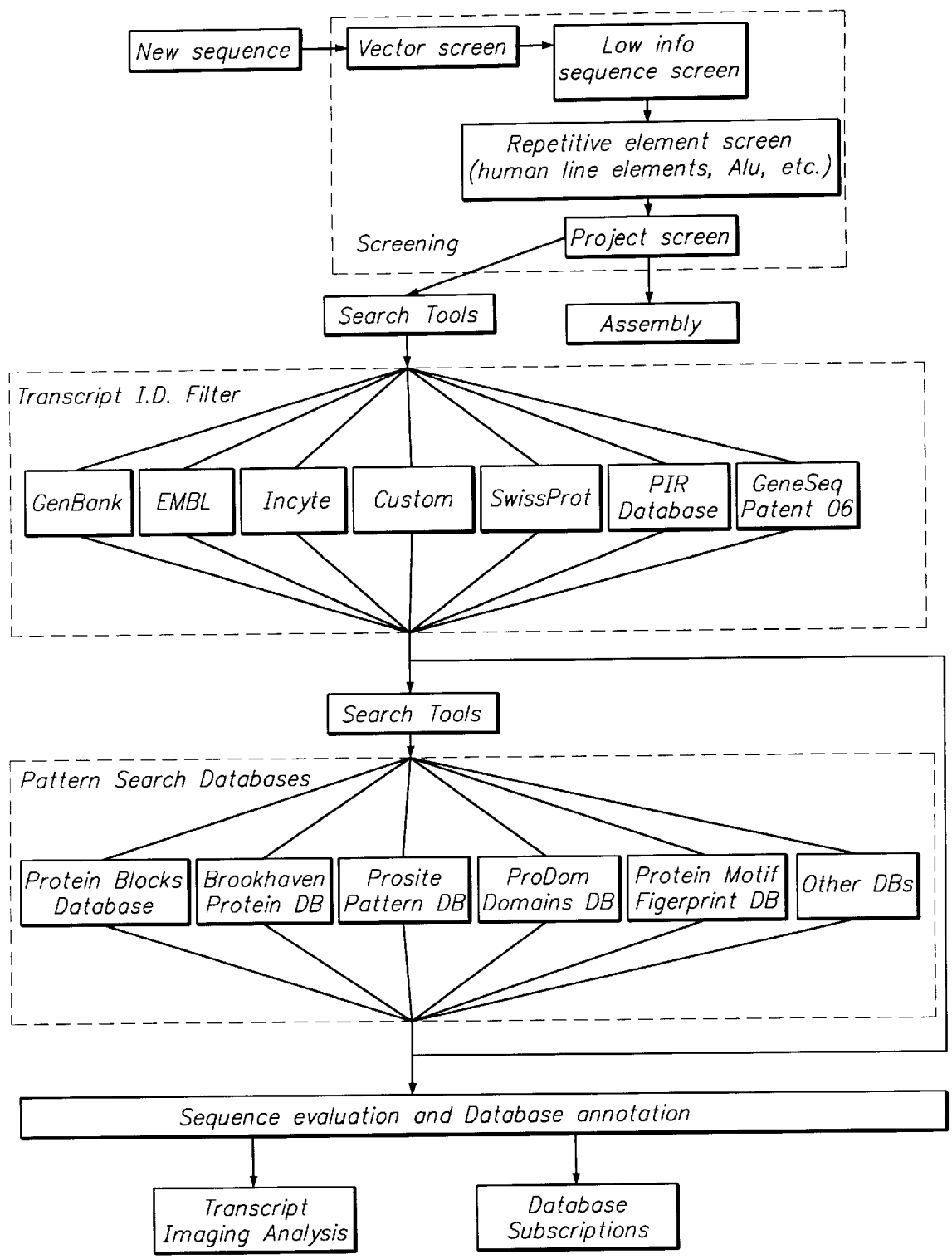
FIG. 4 is a more detailed block diagram of the bioinformatics process from new sequence (that has already been sequenced but not identified) to printout of the transcript imaging analysis and the provision of database subscriptions.

Still with reference to FIG. 3, the Identified Sequences are loaded into processor 6 which is programmed with the abundance sort program. Processor 6 generates the Final Transcript sequences indicated in both FIGS. 2 and 3. FIG. 4 shows a more detailed block diagram of a planned relational computer system, including various searching techniques which can be implemented, along with an assortment of databases to query against.

With reference to FIG. 2, the abundance sort program first performs an operation known as "Tempnum" on the Identified Sequences, to discard all of the Identified Sequences except those which match database entries of selected types. For example, the Tempnum process can select Identified Sequences which represent matches of the following types with database entries (see above for definition): "exact" matches, human "homologous" matches, "other species" matches representing genes present in species other than human), "no" matches (no significant regions of homology with database entries representing previously identified nucleotide sequences), "I" matches (Incyte for not previously known DNA sequences), or "X" matches (matches ESTs in reference database). This eliminates the U, S, M, V, A, R and D sequence (see Table 1 for definitions).

The identified sequence values selected during the "Tempnum" process then undergo a further selection (weeding out) operation known as "Tempred." This operation can, for example, discard all identified sequence values representing matches with selected database entries.

The identified sequence values selected during the "Tempred" process are then classified according to library, during the "Tempdesig" operation. It is contemplated that the "Identified Sequences" can represent sequences from a single library, or from two or more libraries.

Consider first the case that the identified sequence values represent sequences from a single library. In this case, all the identified sequence values determined during "Tempred" undergo sorting in the "Templib" operation, further sorting in the "Libsort" operation, and finally additional sorting in the "Temptarsort" operation. For example, these three sorting operations can sort the identified sequences in order of decreasing "abundance number" (to generate a list of decreasing abundance numbers, each abundance number corresponding to a unique identified sequence entry, or several lists of decreasing abundance numbers, with the abundance numbers in each list corresponding to database entries of a selected type) with redundancies eliminated from each sorted list. In this case, the operation identified as "Cruncher" can be bypassed, so that the "Final Data" values are the organized transcript sequences produced during the "Temptarsort" operation.

We next consider the case that the transcript sequences produced during the "Tempred" operation represent sequences from two libraries (which we will denote the "target" library and the "subtractant" library). For example, the target library may consist of cDNA sequences from clones of a diseased cell, while the subtractant library may consist of cDNA sequences from clones of the diseased cell after treatment by exposure to a drug. For another example, the target library may consist of cDNA sequences from clones of a cell type from a young human, while the subtractant library may consist of cDNA sequences from clones of the same cell type from the same human (at different ages).

In this case, the "Tempdesig" operation routes all transcript sequences representing the target library for processing in accordance with "Templib" (and then "Libsort" and "Temptarsort"), and routes all transcript sequences representing the subtractant library for processing in accordance with "Tempsub" (and then "Subsort" and "Tempsubsort"). For example, the consecutive "Templib," "Libsort," and "Temptarsort" sorting operations sort identified sequences from the target library in order of decreasing abundance number (to generate a list of decreasing abundance numbers, each abundance number corresponding to a database entry, or several lists of decreasing abundance numbers, with the abundance numbers in each list corresponding to database entries of a selected type) with redundancies eliminated from each sorted list. The consecutive "Tempsub," "Subsort," and "Tempsubsort" sorting operations sort identified sequences from the subtractant library in order of decreasing abundance number (to generate a list of decreasing abundance numbers, each abundance number corresponding to a database entry, or several lists of decreasing abundance numbers, with the abundance numbers in each list corresponding to database entries of a selected type) with redundancies eliminated from each sorted list.

The transcript sequences output from the "Temptarsort" operation typically represent sorted lists from which a histogram could be generated in which position along one (e.g., horizontal) axis indicates abundance number (of target library sequences), and position along another (e.g., vertical) axis indicates identified sequence value (e.g., human or non-human gene type). Similarly, the transcript sequences output from the "Tempsubsort" operation typically represent sorted lists from which a histogram could be generated in which position along one (e.g., horizontal) axis indicates abundance number (of subtractant library sequences), and position along another (e.g., vertical) axis indicates identified sequence value (e.g., human or non-human gene type).

The transcript sequences (sorted lists) output from the Tempsubsort and Temptarsort sorting operations are combined during the operation identified as "Cruncher." The "Cruncher" process identifies pairs of corresponding target and subtractant abundance numbers (both representing the same identified sequence value), and divides one by the other to generate a "ratio" value for each pair of corresponding abundance numbers, and then sorts the ratio values in order of decreasing ratio value. The data output from the "Cruncher" operation (the Final Transcript sequence in FIG. 2) is typically a sorted list from which a histogram could be generated in which position along one axis indicates the size of a ratio of abundance numbers (for corresponding identified sequence values from target and subtractant libraries) and position along another axis indicates identified sequence value (e.g., gene type).

Preferably, prior to obtaining a ratio between the two library abundance values, the Cruncher operation also divides each ratio value by the total number of sequences in one or both of the target and subtractant libraries. The resulting lists of "relative" ratio values generated by the Cruncher operation are useful for many medical, scientific, and industrial applications. Also preferably, the output of the Cruncher operation is a set of lists, each list representing a sequence of decreasing ratio values for a different selected subset (e.g. protein family) of database entries.

In one example, the abundance sort program of the invention tabulates for a library the numbers of MRNA transcripts corresponding to each gene identified in a database. These numbers are divided by the total number of clones sampled. The results of the division reflect the relative abundance of the mRNA transcripts in the cell type or tissue from which they were obtained. Obtaining this final data set is referred to herein as "gene transcript image analysis." The resulting subtracted data show exactly what proteins and genes are upregulated and downregulated in highly detailed complexity.

6.5. HUVEC cDNA LIBRARY

In this example, one group of human umbilical vein endothelial cells (HUVEC) were treated with interleukin-1 beta and LPS, and a second group of HUVEC were treated with TNF and interferon gamma. These two groups were combined. The HUVEC cDNA library was custom constructed by Stratagene. Poly(A+)RNA (mRNA) was purified separately from the two batches of induced HUVEC cells. CDNA synthesis was also separated into the two batches, primed separately with both oligo dT and random hexamers. Synthetic adaptor oligonucleotides were ligated onto cDNA ends enabling its insertion into Uni-ZAP™ vector system (Stratagene), allowing high efficiency unidirectional (sense orientation) lambda library construction and the convenience of a plasmid system with blue/white color selection to detect clones with cDNA insertions.

The HUVEC and other libraries discussed in the following examples can be screened with either DNA probes or antibody probes and the pBluescript® phagemid (Stratagene) can be rapidly excised in vivo. The phagemid allows the use of a plasmid system for: easy insert characterization, sequencing, site-directed mutagenesis, the creation of unidirectional deletions and expression of fusion proteins. The custom-constructed library phage particles were infected into *E. coli* host strain XL1-Blue® (Stratagene), which has a high transformation efficiency, increasing the probability of obtaining rare, underrepresented clones in the CDNA library. Subsequently, the CDNA are excised and sequenced on an ABI Sequencer.

Table 2 is an abundance table listing the various gene transcripts in order of decreasing abundance. This computerized sorting simplifies analysis of the tissue and speeds identification of significant new proteins which are specific to this cell type. Endothelial cells line the cardiovascular system, and the more that is known about their composition, particularly in response to activation, the more choices of protein targets to affect in treating disorders of this tissue, such as the highly prevalent atherosclerosis.

6.6. MONOCYTE-CELL cDNA LIBRARY

The human monocyte THP-1 cells were cultured 48 hr with 100 nm TPA and 4, hr with 1 µg/ml LPS, to simulate activated macrophages exposed to endotoxin. Poly(A+) RNA (mRNA) was purified from the activated THP-1 cells. The cDNA library was custom constructed by Stratagene. cDNA synthesis was primed separately with both oligo dT and random hexamers, and the two sets of cDNA copies were treated separately. Synthetic adapter oligonucleotides were ligated onto cDNA ends enabling its insertion into Uni-ZAP™ vector system (Stratagene), allowing high efficiency unidirectional (sense orientation) lambda library construction and the convenience of a plasmid system with blue/white color selection to detect clones with cDNA insertions. Finally, the two libraries were prepared by oligo dT priming and by random hexamer priming, respectively, and were combined into a single library by mixing equal numbers of bacteriophage.

The human mast cell HMC-1 cDNA library was custom constructed by Stratagene, using mRNA purified from cultured HMC-1 cells. The library was prepared by Stratagene essentially as described. The human mast cell (HMC-1) cDNA library was prepared by purifying poly(A+)RNA (mRNA) from human mast cells and then enzymaticly synthesizing double stranded complementary DNA (cDNA) copies of the mRNA. Synthetic adaptor oligonucleotides were ligated onto the ends of the cDNA enabling its insertion into the lambda vector. The HMC-1 library was constructed using the Uni-ZAP™ vector system (Stratagene), allowing high efficiency unidirectional (sense orientation) lambda library construction and the convenience of a plasmid system with blue/white color selection to detect clones with cDNA insertions. For both the THP-1 and HMC-1 libraries, the cDNA were excised as described above and sequenced on an ABI sequencer.

Tables 3 and 4 show comparisons of these two libraries. In Tables 3 and 4 the "normal monocytes" are the HMC-1 cells, and the "activated macrophages" are the THP-1 cells pretreated with PMA and activated with LPS. Table 3 lists in descending order of abundance the most abundant gene transcripts for both cell types. With only 15 gene transcripts from each cell type, this table permits quick, qualitative comparison of the most common transcripts. This abundance sort, with its convenient side-by-side display, provides an immediately useful research tool. In this example, this research tool discloses that 1) only one of the top 15 activated macrophage transcripts is found in the top 15 normal monocyte gene transcripts (poly A binding protein) and 2) a new gene transcript (previously unreported in other databases) is relatively highly represented in activated macrophages but is not similarly prominent in normal macrophages. Such a research tool provides a short-cut to new proteins, such as receptors, cell-surface and intracellular signalling molecules, which can serve as drug targets in commercial drug screening programs. Such a tool could save considerable time over that consumed by a hit and miss discovery program of identifying important proteins in and around cells, not going into the cell to evaluate steady state mRNA.

This illustrates how the gene transcript profiles change with altered cellular function. Those skilled in the art know that the biochemical composition of cells also changes with other functional changes such as cancer, including cancer's various stages, and exposure to toxicity. A gene transcript subtraction profile such as in Table 3 is useful as a first screening tool for gene expression and protein studies.

6.7. SUBTRACTION ANALYSIS OF NORMAL MONOCYTE-CELL AND ACTIVATED MONOCYTE CELL cDNA LIBRARIES

Once the cDNA data are in the computer, the computer program as disclosed in Appendix A was used to obtain ratios of all the gene transcripts in the two libraries discussed in Example 2, and the gene transcripts were sorted by the descending values of their ratios. If a gene transcript is not represented in one library, that gene transcript's abundance is unknown but appears to be less than 1. As an approximation—and to obtain a ratio, which would not be possible if the unrepresented gene were given an abundance of zero—genes which are represented in only one of the two libraries are assigned an abundance of ½. Using ½ for unrepresented clones increases the relative importance of "turned-on" and "turned-off" genes, whose products would be drug candidates. The resulting print-out is called a subtraction table and is an extremely valuable screening method, as is shown by the following data.

Table 4 is a subtraction table, in which the normal monocyte library was electronically "subtracted" from the activated macrophage library. This table highlights most effectively the changes in abundance of the gene transcripts by activation of macrophages. Even among the first 20 gene transcripts listed, there are several unknown gene transcripts. Thus, electronic subtraction is a useful tool with which to assist researchers in identifying much more quickly the basic biochemical changes between two cell types. Such a tool can save universities and pharmaceutical companies which spend billions of dollars on research valuable time and laboratory resources at the early discovery stage and can speed up the drug development cycle, which in turn permits researchers to set up drug screening programs much earlier. Thus, this research tool provides a way to get new drugs to the public faster and more economically.

Also, such a subtraction table can be obtained on an individual patient sample (such as monocytes obtained from a biopsy or blood sample) and can be compared with data provided herein to diagnose conditions associated with macrophage activation.

Table 4 uncovered many new gene transcripts (labeled Incyte clones). Note that many genes are turned on in the activated macrophage (i.e., in the monocyte had a 0 in the bgfreq column). This screening method is superior to other screening techniques, such as the western blot, which are incapable of uncovering such a multitude of discrete new gene transcripts.

The subtraction-screening technique has also uncovered surprising, unexpected gene transcripts in the activated macrophage. For example, many cancer-related gene transcripts (Oncogenes rho, ETS2, rab-2 ras, YPT1-related, and acute myeloid leukemia mRNA) are seen. This screening technique offers a detailed picture of upregulated transcripts, which helps explain why anti-cancer drugs interfere with the patient's immunity mediated by activated macrophages. Armed with knowledge gained from this screening method, those skilled in the art can set up more targeted, more effective drug screening programs to identify drugs which are effective against 1) both relevant cancers and activated macrophage conditions with the same gene transcript profile, 2) cancer alone and 3) activated macrophage conditions.

Smooth muscle senescent protein (22 kd) was turned on in the activated macrophage, which indicates that it is a product to block in inflammation.

6.8. SUBTRACTION ANALYSIS OF NORMAL LIVER CELLS AND HEPATITUS INFECTED LIVER CELL CDNA LIBRARIES

In this example, rats are exposed to hepatitis virus and maintained in the colony until they show definite signs of hepatitis. Of the rats diagnosed with hepatitis, one half of the rats are treated with a new anti-hepatitis agent (ARA). Liver samples are obtained from all rats before exposure to the hepatitis virus and at the end of AHA treatment or no treatment. In addition, liver samples can be obtained from rats with hepatitis just prior to AHA treatment.

The liver samples are treated as described in Examples 1 and 2 to obtain mRNA and subsequently to sequence cDNA. The CDNA from each sample are process and analyzed for abundance according to the computer program in Appendix A. The resulting gene transcript images of the cDNA provide detailed pictures of the baseline (control) for each animal and of the infected and/or treated state of the animals. cDNA data for a group of samples can be combined into a group summary gene transcript profile for all control samples, all samples from infected rats and all samples from AHA-treated rats.

Subtractions are performed between appropriate individual libraries and the grouped libraries. For individual animals, control and post-study samples can be subtracted. Also, if samples are obtained before and after AHA treatment, that data from individual animals and treatment groups can be subtracted. In addition, the data for all control samples can be pooled and averaged. The control average can be subtracted from averages of both post-study AHA and post-study non-AHA cDNA samples. If pre- and post-treatment samples are available, pre- and post-treatment samples can be compared individually (or electronically averaged) and subtracted.

These subtraction tables are used in two general ways. First, the differences are analyzed for gene transcripts which are associated with continuing hepatic deterioration or healing. The subtraction tables are tools to isolate the effects of the drug treatment from the underlying basic pathology of hepatitis. Because hepatitis affects many parameters, additional liver toxicity has been difficult to detect with only blood tests for the usual enzymes. The gene transcript profile and subtraction provides a much more complex biochemical picture which researchers have needed to analyze such complex problems.

Second, the subtraction tables provide a tool for identifying clinical markers, individual proteins or other biochemical determinants which are used to predict and/or evaluate a clinical endpoint, such as disease, improvement due to the drug, and even additional pathology due to the drug. The subtraction tables specifically highlight genes which are turned on or off. Thus, the subtraction tables provide a first screen for a set of gene transcript candidates for use as clinical markers. Subsequently, electronic subtractions of additional cell and tissue libraries reveal which of the potential markers are in fact found in different cell and tissue libraries. Candidate gene transcripts found in additional libraries are removed from the set of potential clinical markers. Then, tests of blood or other relevant samples which are known to lack and have the relevant condition are compared to validate the selection of the clinical marker. In this method, the particular physiologic function of the protein transcript need not be determined to qualify the gene transcript as a clinical marker.

6.9. PHASE I CLINICAL TRIALS

Based on the establishment of safety and effectiveness in the above animal tests, Phase I clinical tests are undertaken. Normal patients are subjected to the usual preliminary clinical laboratory tests. In addition, appropriate samples are taken and subjected to gene transcript analysis. Additional patient samples are taken at predetermined intervals during the test. The samples are subjected to gene transcript analysis as described above. In addition, the biochemical changes noted in the rats are carefully evaluated as clinical markers in the followed patients. Changes in the gene transcript analyses are evaluated as indicators of toxicity by correlation with clinical signs and symptoms and other laboratory results. In addition, subtraction is performed on individual patient samples and on averaged patient samples. The subtraction analysis highlights any toxicological changes in the treated patients. This is a highly refined determinant of toxicity. The subtraction method also annotates clinical markers. Further subgroups can be analyzed by subtraction analysis, including, for example, 1) segregation by occurrence and type of adverse effect, 2) segregation by dosage.

6.10. GENE TRANSCRIPT IMAGING ANALYSIS IN CLINICAL STUDIES

A gene transcript imaging analysis (or multiple gene transcript imaging analyses) is a useful tool in other clinical studies. For example, the differences in gene transcript imaging analyses before and after treatment can be assessed for patients on placebo and drug treatment. This method also effectively screen for clinical markers to follow in clinical use of the drug.

6.11. COMPARATIVE GENE TRANSCRIPT ANALYSIS BETWEEN SPECIES

The subtraction method can be used to screen cDNA libraries from diverse sources. For example, the same cell types from different species can be compared by comparative gene transcript analysis to screen for specific differences, such as in detoxification enzyme systems. Such testing aids in the selection and validation of an animal model for the commercial purpose of drug screening or toxicological testing of drugs intended for human or animal use. When the comparison between animals of different species is shown in columns for each species, we refer to this as an interspecies comparison, or zoo blot.

This invention employs databases of co-pending U.S. patent applications Ser. Nos. 08/179,873 filed Jan. 11, 1994; 08/137,951 filed Oct. 14, 1993; and 08/100,523 filed Aug. 3, 1993, which is a continuation-in-part application of co-pending U.S. patent application Ser. No. 07/977,780 filed Nov. 19, 1992, which is a continuation-in-part application of co-pending U.S. patent application Ser. No. 07/916,491 filed Jul. 17, 1992. These five patent applications (whose text is incorporated herein by reference) include teaching which may be applied in implementing such other embodiments of the present invention.

Other embodiments of the invention employ other databases, such as a random peptide database, a polymer database, a synthetic oligomer database, or a oligonucleotide database of the type described in U.S. Pat. No. 5,270,170, issued Dec. 14, 1993 to Cull, et al., PCT International Application Publication No. WO 9322684, published Nov. 11, 1993, PCT International Application Publication No. WO 9306121, published Apr. 1, 1993, or PCT International Application Publication No. WO 9119818, published Dec. 26, 1991. These four references (whose text is incorporated herein by reference) include teaching which may be applied in implementing such other embodiments of the present invention.

All references referred to in the preceding text are hereby expressly incorporated by reference herein.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments.

TABLE 1

| Designations (D) | Distribution (F) |
|---|---|
| E = Exact | C = Non-specific |
| H = Homologous | P = Cell/tissue specific |

TABLE 1-continued

| | |
|---|---|
| O = Other species | U = Unknown |
| N = No match | Species (S) |
| | |
| D = Noncoding gene | H = Human |
| U = Nonreadable | A = Ape |
| R = Repetitive DNA | P = Pig |
| A = Poly-A only | D = Dog |
| V = Vector only | V = Bovine |
| M = Mitochondrial DNA | B = Rabbit |
| S = Skip | R = Rat |
| I = Match Incyte clone | M = Mouse |
| X = EST match | S = Hamster |
| Library (L) | C = Chicken |
| | |
| U = U937 | F = Amphibian |
| M = HMC | I = Invertebrate |
| T = THP-1 | Z = Protozoan |
| H = HUVEC | G = Fungi |
| S = Spleen | Function (R) |
| | |
| L = Lung | T = Translation |
| Y = T & B cell | L = Protein processing |
| A = Adenoid | R = Ribosomal protein |
| Localization (Z) | O = Oncogene |
| | |
| N = Nuclear | G = GTP binding ptn |
| C = Cytoplasmic | V = Viral element |
| K = Cytoskeleton | Y = Kinase/phosphatase |
| E = Cell surface | A = Tumor antigen related |
| Z = Intracellular memb | I = Binding proteins |
| M = Mitochondrial | D = NA-binding/transcription |
| S = Secreted | B = Surface molecule/receptor |
| U = Unknown | C = $Ca^{++}$ binding protein |
| X = Other | S = Ligands/effectors |
| Status (I) | H = Stress response protein |
| | |
| 0 = No current interest | E = Enzyme |
| 1 = Do primary analysis | F = Ferroprotein |
| 2 = Primary analysis done | P = Protease/inhibitor |
| 3 = Full length sequence | Z = Oxidative phosphorylation |
| 4 = Secondary analysis | Q = Sugar metabolism |
| 5 = Tissue northern | M = Amino acid metabolism |
| 6 = Obtain full length | N = Nucleic acid metabolism |
| | W = Lipid metabolism |
| | K = Structural |
| | X = Other |
| | U = unknown |

TABLE 2

Clone numbers 15000 through 20000
Libraries: HUVEC
Designations: All
Condensed format analysis
Arranged by ABUNDANCE
Total clones represented: 5000
Total clones analyzed: 5000 l = library   d = designation   f = distribution   z = location   r = function   c = certain?   s = species 319 genes, for a total of 1713 clones

| Coincidence number | V N | V Clones/10000 % | l | d | f | z | r | c | entry | s | descriptor | length | init | i |
|---|---|---|---|---|---|---|---|---|---|---|---|---|---|---|
| 1 | 15365 | 67 | 867 | H | E | C | C | R | HSRPL41 | | Ribosomal protein L41 | 91 | 0 | |
| 2 | 15004 | 65 | 841 | H | I | U | U | U | NCY015004 | | INCYTE clone 015004 | 0 | 2 | |
| 3 | 15638 | 63 | 815 | H | I | U | U | U | NCY015638 | | INCYTE clone 015638 | 0 | 0 | |
| 4 | 15390 | 50 | 647 | H | I | U | U | U | NCY015390 | | INCYTE clone 015390 | 0 | 0 | |
| 5 | 15193 | 47 | 608 | H | E | C | S | I | HSFIB1 | | Fibronectin | 829 | 0 | |
| 6 | 15220 | 47 | 608 | H | O | C | C | R | RRRPL9 | R | Ribosomal protein L9 | 547 | 0 | |
| 7 | 15280 | 47 | 608 | H | I | U | U | U | NCY015280 | | INCYTE clone 015280 | 0 | 0 | |
| 8 | 15583 | 33 | 427 | H | X | U | U | U | M62060 | | EST HHCH09 (IGR) | −60 | 0 | |
| 9 | 15662 | 31 | 401 | H | E | C | K | K | HSACTCGR | | Actin, cytoskeletal gamma | 41 | 0 | |
| 10 | 15026 | 29 | 375 | H | I | U | U | U | NCY015026 | | INCYTE clone 015026 | 0 | 0 | |
| 11 | 15279 | 24 | 310 | H | E | C | C | T | HSEF1AR | | Elongation factor 1-alpha | 871 | 0 | |
| 12 | 15027 | 23 | 298 | H | I | U | U | U | NCY015027 | | INCYTE clone 015027 | 0 | 0 | |
| 13 | 15033 | 20 | 259 | H | I | U | U | U | NCY015033 | | INCYTE clone 015033 | 0 | 0 | |
| 14 | 15198 | 20 | 259 | H | I | U | U | U | NCY015198 | | INCYTE clone 015198 | 0 | 0 | |
| 15 | 15809 | 20 | 259 | H | E | P | S | P | HSCOLL1 | | Collagenase | 1228 | 0 | |
| 16 | 15221 | 19 | 246 | H | I | U | U | U | NCY015221 | | INCYTE clone 015221 | 0 | 0 | |
| 17 | 15263 | 19 | 246 | H | I | U | U | U | NCY015263 | | INCYTE clone 015263 | 0 | 0 | |
| 18 | 15290 | 19 | 246 | H | I | U | U | U | NCY015290 | | INCYTE clone 015290 | 0 | 0 | |
| 19 | 15350 | 18 | 233 | H | I | U | U | U | NCY015350 | | INCYTE clone 015350 | 0 | 0 | |
| 20 | 15030 | 17 | 220 | H | I | U | U | U | NCY015030 | | INCYTE clone 015030 | 0 | 0 | |
| 21 | 15234 | 17 | 220 | H | I | U | U | U | NCY015234 | | INCYTE clone 015234 | 0 | 0 | |
| 22 | 15459 | 16 | 207 | H | I | U | U | U | NCY015459 | | INCYTE clone 015459 | 0 | 0 | |
| 23 | 15353 | 15 | 194 | H | I | U | U | U | NCY015353 | | INCYTE clone 015353 | 0 | 0 | |
| 24 | 15378 | 15 | 194 | H | E | P | C | Y | S76965 | | Protein kinase inhibitor | −571 | 0 | |
| 25 | 15255 | 14 | 181 | H | E | P | U | U | HUMTHYB4 | | Thymosin beta-4 | 168 | 0 | |
| 26 | 15401 | 14 | 181 | H | E | P | Z | C | HSLIPCR | | Lipocortin I | 394 | 0 | |
| 27 | 15425 | 14 | 181 | H | E | C | C | T | HSPOLYAB | | Poly-A binding protein | 1583 | 0 | |
| 28 | 18212 | 14 | 181 | H | E | P | U | U | HUMTHYMA | | Thymosin, alpha | −120 | 0 | |
| 29 | 18216 | 14 | 181 | H | E | P | E | X | HSMRP1 | | Motility related protein; MRP-1; CD-9 | 80 | 0 | |
| 30 | 15189 | 13 | 168 | H | E | P | U | H | HS18D | | Interferon inducible protein 1–8D | 356 | 0 | |
| 31 | 15031 | 12 | 155 | H | E | P | C | I | HUMFKBP | | FK506 binding protein | −65 | 0 | |
| 32 | 15306 | 12 | 155 | H | E | C | N | D | HSH2AZ | | Histone H2A | −32 | 0 | |
| 33 | 15621 | 12 | 155 | H | E | P | E | B | HUMLEC | | Lectin, B-galactosidase binding, 14 kDa | 428 | 0 | |
| 34 | 15789 | 11 | 142 | H | I | U | U | U | NCY015789 | | INCYTE clone 015789 | 0 | 0 | |
| 35 | 16578 | 11 | 142 | H | E | C | C | R | HSRPS11 | | Ribosomal protein S11 | 424 | 0 | |
| 36 | 16632 | 11 | 142 | H | X | U | U | U | M61984 | | EST HHCA13 (IGR) | 0 | 0 | |
| 37 | 18314 | 11 | 142 | H | I | U | U | U | NCY018314 | | INCYTE clone 018314 | 0 | 0 | |
| 38 | 15367 | 10 | 129 | H | I | U | U | U | NCY015367 | | INCYTE clone 015367 | 0 | 0 | |
| 39 | 15415 | 10 | 129 | H | E | U | U | H | HSIFNIN1 | | interferon inducible mRNA 1–18D | 457 | 0 | |
| 40 | 15633 | 10 | 129 | H | E | C | C | Q | HSLDHAR | | Lactate dehydrogenase | 228 | 0 | |
| 41 | 15813 | 10 | 129 | H | O | P | K | K | CHKNMHCB | C | Myosin heavy chain B, nonmuscle | −1017 | 0 | |
| 42 | 18210 | 10 | 129 | H | I | U | U | U | NCY018210 | | INCYTE clone 018210 | 0 | 2 | |
| 43 | 18233 | 10 | 129 | H | E | C | N | D | HSRPII140 | | RNA polymerase II, 140 kDa subunit | 442 | 0 | |
| 44 | 18996 | 10 | 129 | H | I | U | U | U | NCY018996 | | INCYTE clone 018996 | 0 | 0 | |
| 45 | 15088 | 9 | 116 | H | E | C | C | F | HUMFERL | | Ferritin, light chain | −271 | 0 | |
| 46 | 15714 | 9 | 116 | H | I | U | U | U | NCY015714 | | INCYTE clone 015714 | 0 | 0 | |
| 47 | 15720 | 9 | 116 | H | I | U | U | U | NCY015720 | | INCYTE clone 015720 | 0 | 0 | |
| 48 | 15863 | 9 | 116 | H | I | U | U | U | NCY015863 | | INCYTE clone 015863 | 0 | 0 | |
| 49 | 16121 | 9 | 116 | H | E | P | S | S | HSET | | Endothelin; vasoconstrictor peptide | 878 | 0 | |
| 50 | 18252 | 9 | 116 | H | I | U | U | U | NCY018252 | | INCYTE clone 018252 | 0 | 0 | |
| 51 | 15351 | 8 | 103 | H | E | P | C | I | HUMALBP | | Lipid binding protein, adipocyte | 441 | 0 | |
| 52 | 15370 | 8 | 103 | H | I | U | U | U | NCY015370 | | INCYTE clone 015370 | 0 | 0 | |
| 53 | 15670 | 8 | 103 | H | O | C | M | Z | BTCIASHI | V | NADH-ubiquinone oxidoreductase CI-ASHI | 555 | 0 | |
| 54 | 15795 | 8 | 103 | H | I | U | U | U | NCY015795 | | INCYTE clone 015795 | 0 | 0 | |
| 55 | 16245 | 8 | 103 | H | I | U | U | U | NCY016245 | | INCYTE clone 016245 | 0 | 0 | |
| 56 | 18262 | 8 | 103 | H | I | U | U | U | NCY018262 | | INCYTE clone 018262 | 0 | 0 | |
| 57 | 18321 | 8 | 103 | H | E | C | C | R | HSRPL17 | | Ribosomal protein L17 | 425 | 0 | |
| 58 | 15126 | 7 | 91 | H | O | C | C | R | XLRPL1BR | F | Ribosomal protein L1 | −72 | 0 | |
| 59 | 15133 | 7 | 91 | H | E | C | K | K | HSAC07 | | Actin, beta- | 2236 | 0 | |
| 60 | 15245 | 7 | 91 | H | I | U | U | U | NCY015245 | | INCYTE clone 015245 | 0 | 0 | |
| 61 | 15288 | 7 | 91 | H | I | U | U | U | NCY015288 | | INCYTE clone 015288 | 0 | 0 | |
| 62 | 15294 | 7 | 91 | H | E | C | C | Q | HSGAPDR | | Glyceraldehyde 3-PO4 dehydrogenase | 763 | 0 | |
| 63 | 15442 | 7 | 91 | H | E | P | E | B | HUMLAMB | | Laminin receptor, 54 kDa | 902 | 0 | |
| 64 | 15485 | 7 | 91 | H | E | C | C | N | HSNGMRNA | | Uracil DNA glycosylase | 747 | 0 | |
| 65 | 16646 | 7 | 91 | H | I | U | U | U | NCY016646 | | INCYTE clone 016646 | 0 | 0 | |
| 66 | 18003 | 7 | 91 | H | E | P | S | S | HUMPAIA | | Plsmnogen activator gene (5'-upstrm) | −1465 | 0 | |

TABLE 2-continued

Clone numbers 15000 through 20000
Libraries: HUVEC
Designations: All
Condensed format analysis
Arranged by ABUNDANCE
Total clones represented: 5000
Total clones analyzed: 5000
l = library   d = designation   f = distribution   z = location   r = function   c = certain?   s = species
319 genes, for a total of 1713 clones

| Coincidence number | V N | V Clones/10000 % | l | d | f | z | r | c | entry | s | descriptor | length | init i |
|---|---|---|---|---|---|---|---|---|---|---|---|---|---|
| 67 | 15032 | 6 | 78 | H | E | C | C | L | HUMUB | | Ubiquitin | 458 | 0 |
| 68 | 15267 | 6 | 78 | H | E | C | C | R | HSRPS8 | | Ribosomal protein S8 | −2004 | 0 |
| 69 | 15295 | 6 | 78 | H | I | U | U | U | NCY015295 | | INCYTE clone 015295 | 0 | 0 |
| 70 | 15458 | 6 | 78 | H | O | C | C | R | RNRPS10R | R | Ribosomal protein S10 | 497 | 0 |
| 71 | 15832 | 6 | 78 | H | O | C | C | Q | RSGALEM | R | UDP-galactose epimerase | 888 | 2 |
| 72 | 15928 | 6 | 78 | H | E | P | S | I | HUMAPOJ | | Apolipoprotein J | 202 | 0 |
| 73 | 16598 | 6 | 78 | H | E | C | K | K | HUMTBBM40 | | Tubulin, beta | −705 | 0 |
| 74 | 18218 | 6 | 78 | H | I | U | U | U | NCY018218 | | INCYTE clone 018218 | 0 | 0 |
| 75 | 18499 | 6 | 78 | H | E | P | U | X | HSP27 | | Hydrophobic protein p27; IFN inducible | 395 | 0 |
| 76 | 18963 | 6 | 78 | H | I | U | U | U | NCY018963 | | INCYTE clone 018963 | 0 | 0 |
| 77 | 18997 | 6 | 78 | H | I | U | U | U | NCY018997 | | INCYTE clone 018997 | 0 | 0 |
| 78 | 15432 | 5 | 65 | H | E | C | C | Q | HSAGALAR | | Galactosidase A, alpha | 1004 | 0 |
| 79 | 15475 | 5 | 65 | H | I | U | U | U | NCY015475 | | INCYTE clone 015475 | 0 | 0 |
| 80 | 15721 | 5 | 65 | H | I | U | U | U | NCY015721 | | INCYTE clone 015721 | 0 | 0 |
| 81 | 15865 | 5 | 65 | H | I | U | U | U | NCY015865 | | INCYTE clone 015865 | 0 | 0 |
| 82 | 16270 | 5 | 65 | H | I | U | U | U | NCY016270 | | INCYTE clone 016270 | 0 | 0 |
| 83 | 16886 | 5 | 65 | H | I | U | U | U | NCY016886 | | INCYTE clone 016886 | 0 | 2 |
| 84 | 18500 | 5 | 65 | H | I | U | U | U | NCY018500 | | INCYTE clone 018500 | 0 | 0 |
| 85 | 18503 | 5 | 65 | H | I | U | U | U | NCY018503 | | INCYTE clone 018503 | 0 | 0 |
| 86 | 19672 | 5 | 65 | H | O | C | C | R | RRRPL34 | R | ribosomal protein L34 | 323 | 0 |
| 87 | 15086 | 4 | 52 | H | O | C | C | R | XLRPL1AR | F | Ribosomal protein L1a | 913 | 0 |
| 88 | 15113 | 4 | 52 | H | E | C | C | T | HUMIFNWRS | | tRNA synthetase, tryptophanyl; IFN-ind | −112 | 0 |
| 89 | 15242 | 4 | 52 | H | I | U | U | U | NCY015242 | | INCYTE clone 015242 | 0 | 0 |
| 90 | 15249 | 4 | 52 | H | I | U | U | U | NCY015249 | | INCYTE clone 015249 | 0 | 0 |
| 91 | 15377 | 4 | 52 | H | I | U | U | U | NCY015377 | | INCYTE clone 015377 | 0 | 0 |
| 92 | 15407 | 4 | 52 | H | I | U | U | U | NCY015407 | | INCYTE clone 015407 | 0 | 0 |
| 93 | 15473 | 4 | 52 | H | I | U | U | U | NCY015473 | | INCYTE clone 015473 | 0 | 0 |
| 94 | 15588 | 4 | 52 | H | E | C | C | R | HSRPS12 | | Ribosomal protein S12 | 218 | 0 |
| 95 | 15684 | 4 | 52 | H | E | C | C | T | HSEF1G | | Elongation factor 1-gamma | 378 | 0 |
| 96 | 15782 | 4 | 52 | H | I | U | U | U | NCY015782 | | INCYTE clone 015782 | 0 | 0 |
| 97 | 15916 | 4 | 52 | H | E | C | C | R | HSRPS18 | | Ribosomal protein S18 | 522 | 0 |
| 98 | 15930 | 4 | 52 | H | I | U | U | U | NCY015930 | | INCYTE clone 015930 | 0 | 0 |
| 99 | 16108 | 4 | 52 | H | I | U | U | U | NCY016108 | | INCYTE clone 016108 | 0 | 0 |
| 100 | 16133 | 4 | 52 | H | I | U | U | U | NCY016133 | | INCYTE clone 016133 | 0 | 0 |
| 101 | 16211 | 4 | 52 | H | X | U | U | U | M85502 | | EST HFBCJ05 (IGR) | 0 | 0 |
| 102 | 16301 | 4 | 52 | H | X | U | U | U | M78204 | | EST 01797 (IGR) | 0 | 0 |
| 103 | 16412 | 4 | 52 | H | E | C | C | R | HUMRPS7A | | Ribosomal protein S7a | 472 | 0 |
| 104 | 16413 | 4 | 52 | H | I | U | U | U | NCY016413 | | INCYTE clone 016413 | 0 | 0 |
| 105 | 16651 | 4 | 52 | H | I | U | U | U | NCY016651 | | INCYTE clone 016651 | 0 | 0 |
| 106 | 16668 | 4 | 52 | H | E | P | S | S | HSEPIT1 | | Growth factor, epithelial cell (EGF) | 132 | 0 |
| 107 | 17645 | 4 | 52 | H | X | U | U | U | M62279 | | EST HHCC14 (IGR) | 0 | 0 |
| 108 | 19175 | 4 | 52 | H | X | U | U | U | R | HSAAABTZR | EST AAABTZR (UK-HGMP) | 0 | 0 |
| 109 | 15028 | 3 | 39 | H | E | C | C | R | HUMSRAA | | Ribosomal protein S16 | 343 | 0 |
| 110 | 15047 | 3 | 39 | H | E | C | C | O | HSTUMP | | Translation controlled tumor protein | 593 | 0 |
| 111 | 15061 | 3 | 39 | H | E | P | E | B | HSFNRB | | Fibronectin receptor beta subunit | 227 | 0 |
| 112 | 15079 | 3 | 39 | H | X | U | U | U | M79268 | | EST 01423 (Venter) | 0 | 0 |
| 113 | 15104 | 3 | 39 | H | I | U | U | U | NCY015104 | | INCYTE clone 015104 | 0 | 0 |
| 114 | 15123 | 3 | 39 | H | E | C | C | R | HUMRPL18A | | Ribosomal protein L18 | 560 | 0 |
| 115 | 15190 | 3 | 39 | H | E | P | S | S | HUMMCAF | | Chemotactic protein MCP-1, monocyte | 330 | 0 |
| 116 | 15299 | 3 | 39 | H | E | C | C | Q | HUMTPI | | Triosephosphate isomerase | 9 | 0 |
| 117 | 15357 | 3 | 39 | H | I | U | U | U | NCY015357 | | INCYTE clone 015357 | 0 | 0 |
| 118 | 15368 | 3 | 39 | H | I | U | U | U | NCY015368 | | INCYTE clone 015368 | 0 | 0 |
| 119 | 15454 | 3 | 39 | H | I | U | U | U | NCY015454 | | INCYTE clone 015454 | 0 | 0 |
| 120 | 15506 | 3 | 39 | H | I | U | U | U | NCY015506 | | INCYTE clone 015506 | 0 | 0 |
| 121 | 15507 | 3 | 39 | H | I | U | U | U | NCY015507 | | INCYTE clone 015507 | 0 | 0 |
| 122 | 15510 | 3 | 39 | H | I | U | U | U | NCY015510 | | INCYTE clone 015510 | 0 | 0 |
| 123 | 15517 | 3 | 39 | H | I | U | U | U | NCY015517 | | INCYTE clone 015517 | 0 | 0 |
| 124 | 15774 | 3 | 39 | H | O | C | C | R | RNRPL37 | R | Ribosomal protein L37 | 3223 | 0 |
| 125 | 15785 | 3 | 39 | H | E | P | K | K | HSMRLCM | | Myosin regulatory L chain | 440 | 0 |
| 126 | 15919 | 3 | 39 | H | I | U | U | U | NCY015919 | | INCYTE clone 015919 | 0 | 0 |
| 127 | 15936 | 3 | 39 | H | I | U | U | U | NCY015936 | | INCYTE clone 015936 | 0 | 0 |
| 128 | 15937 | 3 | 39 | H | I | U | U | U | NCY015937 | | INCYTE clone 015937 | 0 | 0 |
| 129 | 15955 | 3 | 39 | H | I | U | U | U | NCY015955 | | INCYTE clone 015955 | 0 | 0 |
| 130 | 16071 | 3 | 39 | H | I | U | U | U | NCY016071 | | INCYTE clone 016071 | 0 | 0 |
| 131 | 16868 | 3 | 39 | H | I | U | U | U | NCY016868 | | INCYTE clone 016868 | 0 | 0 |
| 132 | 16923 | 3 | 39 | H | E | C | M | Z | HUMTLCA | | ADP/ATP translocase | 289 | 0 |

TABLE 2-continued

Clone numbers 15000 through 20000
Libraries: HUVEC
Designations: All
Condensed format analysis
Arranged by ABUNDANCE
Total clones represented: 5000
Total clones analyzed: 5000
l = library   d = designation   f = distribution   z = location   r = function   c = certain?   s = species
319 genes, for a total of 1713 clones

| Coincidence number | V N | V Clones/10000 % | l | d | f | z | r | c | entry | s | descriptor | length | init | i |
|---|---|---|---|---|---|---|---|---|---|---|---|---|---|---|
| 133 | 17097 | 3 39 | H | I | U | U | U | | NCY017097 | | INCYTE clone 017097 | 0 | 0 | |
| 134 | 17114 | 3 39 | H | E | C | C | R | | HUMRRL3A | | Ribosomal protein L3 | 303 | 0 | |
| 135 | 17160 | 3 39 | H | I | U | U | U | | NCY017160 | | INCYTE clone 017160 | 0 | 0 | |
| 136 | 17530 | 3 39 | H | I | U | U | U | | NCY017530 | | INCYTE clone 017530 | 0 | 0 | |
| 137 | 17543 | 3 39 | H | E | P | E | B | | HSLAMBR | | laminin binding protein | 0 | 0 | |
| 138 | 17599 | 3 39 | H | X | U | U | U | | T02946 | | EST FB17B2 (Sikela) | 0 | 0 | |
| 139 | 17602 | 3 39 | H | I | U | U | U | | NCY017602 | | INCYTE clone 017602 | 0 | 0 | |
| 140 | 17700 | 3 39 | H | E | C | N | D | | HUMBTFC | | BTF3 tcr factor; Fc gamma receptor IIB | −36 | 0 | |
| 141 | 18085 | 3 39 | H | I | U | U | U | | NCY018085 | | INCYTE clone 018085 | 0 | 0 | |
| 142 | 18086 | 3 39 | H | E | C | C | R | | HUMRPS4X | | Ribosomal protein S4 | 742 | 0 | |
| 143 | 18258 | 3 39 | H | I | U | U | U | | NCY018258 | | INCYTE clone 018258 | 0 | 0 | |
| 144 | 18259 | 3 39 | H | X | U | U | U | | M62278 | | EST HHCJ64 (IGR) | 0 | 0 | |
| 145 | 18306 | 3 39 | H | I | U | U | U | | NCY018306 | | INCYTE clone 018306 | 0 | 0 | |
| 146 | 18324 | 3 39 | H | E | C | N | D | | HUMHMG14 | | Non-histone DNA-binding protein | −156 | 0 | |
| 147 | 18512 | 3 39 | H | I | U | U | U | | NCY018512 | | INCYTE clone 018512 | 0 | 0 | |
| 148 | 18635 | 3 39 | H | I | U | U | U | | NCY018635 | | INCYTE clone 018635 | 0 | 0 | |
| 149 | 18870 | 3 39 | H | E | P | C | Y | | HSCL100 | | Tyrosine phosphatase CL 100 | −107 | 0 | |
| 150 | 18968 | 3 39 | H | I | U | U | U | | NCY018968 | | INCYTE clone 018968 | 0 | 0 | |
| 151 | 19143 | 3 39 | H | I | U | U | U | | NCY019143 | | INCYTE clone 019143 | 0 | 0 | |
| 152 | 19186 | 3 39 | H | I | U | U | U | | NCY019186 | | INCYTE clone 019186 | 0 | 0 | |
| 153 | 19358 | 3 39 | H | H | U | U | P | | SYNSTFBFP | | MS-2; homologous to cystatin beta | 148 | 3 | |
| 154 | 19760 | 3 39 | H | I | U | U | U | | NCY019760 | | INCYTE clone 019760 | 0 | 0 | |
| 155 | 19783 | 3 39 | H | O | U | C | W | | S80257 | P | Phospholipid H-peroxide GT percxidase | 436 | 1 | |
| 156 | 15029 | 2 26 | H | X | U | U | U | | HUMXT01423 | | EST 01423 | 0 | 0 | |
| 157 | 15044 | 2 26 | H | I | U | U | U | | NCY015044 | | INCYTE clone 015044 | 0 | 0 | |
| 158 | 15092 | 2 26 | H | I | U | U | U | | NCY015092 | | INCYTE clone 015092 | 0 | 0 | |
| 159 | 15093 | 2 26 | H | I | U | U | U | | NCY015093 | | INCYTE clone 015093 | 0 | 0 | |
| 160 | 15136 | 2 26 | H | O | C | C | R | | RNRIPRL38 | R | Ribosomal protein L38 | 0 | 0 | |
| 161 | 15191 | 2 26 | H | E | C | C | I | | HSTHIO | | Metallothionein | 0 | 0 | |
| 162 | 15203 | 2 26 | H | I | U | U | U | | NCY015203 | | INCYTE clone 015203 | 0 | 0 | |
| 163 | 15272 | 2 26 | H | E | C | N | V | | HUMRIRT | | Retinoic acid inducible retrovirus | 0 | 0 | |
| 164 | 15297 | 2 26 | H | I | U | U | U | | NCY015297 | | INCYTE clone 015297 | 0 | 0 | |
| 165 | 15303 | 2 26 | H | I | U | U | U | | NCY015303 | | INCYTE clone 015303 | 0 | 0 | |
| 166 | 15356 | 2 26 | H | O | C | C | R | | RRRPL21 | R | Ribosomal protein L21 | 508 | 0 | |
| 167 | 15366 | 2 26 | H | I | U | U | U | | NCY015366 | | INCYTE clone 015366 | 0 | 0 | |
| 168 | 15371 | 2 26 | H | E | C | N | D | | HUMH2AZ | | Histone H2A.Z | 188 | 0 | |
| 169 | 15381 | 2 26 | H | E | C | K | K | | HUMPROF | | Profilin | 214 | 0 | |
| 170 | 15570 | 2 26 | H | I | U | U | U | | NCY015570 | | INCYTE clone 015570 | 0 | 0 | |
| 171 | 15643 | 2 26 | H | E | U | E | B | | HUMQM | | Laminin rcptr homolog; Wilm's tmr rel | 629 | 0 | |
| 172 | 15652 | 2 26 | H | U | U | U | U | | NCY015652 | | INCYTE clone 015652 | 0 | 0 | |
| 173 | 15711 | 2 26 | H | E | U | U | O | | HUML6A | | Tumor antigen L6 | 367 | 0 | |
| 174 | 15776 | 2 26 | H | E | U | U | U | | HS23KDHBP | | Highly basic protein, 23 kDa | 594 | 0 | |
| 175 | 15788 | 2 26 | H | E | P | S | P | | HUM4COLA | | Collagenase, type IV | −291 | 0 | |
| 176 | 15817 | 2 26 | H | I | U | U | U | | NCY015817 | | INCYTE clone 015817 | 0 | 0 | |
| 177 | 15833 | 2 26 | H | E | U | U | U | | HSPGP95 | | Neuroendocrine protein PGP 9,5 | −113 | 0 | |
| 178 | 15834 | 2 26 | H | I | U | U | U | | NCY015834 | | INCYTE clone 015834 | 0 | 0 | |
| 179 | 15848 | 2 26 | H | I | U | U | U | | NCY015848 | | INCYTE clone 015848 | 0 | 0 | |
| 180 | 15854 | 2 26 | H | I | U | U | U | | NCY015854 | | INCYTE clone 015854 | 0 | 0 | |
| 181 | 15858 | 2 26 | H | I | U | U | U | | NCY015858 | | INCYTE clone 015858 | 0 | 0 | |
| 182 | 15866 | 2 26 | H | I | U | U | U | | NCY015866 | | INCYTE clone 015866 | 0 | 0 | |
| 183 | 15868 | 2 26 | H | E | C | C | W | | HUMSAP1 | | Saposin B; sphingolipid activator ptn | −492 | 0 | |
| 184 | 15887 | 2 26 | H | E | C | C | T | | HSWRSX11 | | tRNA synthetase, tryptophanyl | 414 | 0 | |
| 185 | 15920 | 2 26 | H | I | U | U | U | | NCY015920 | | INCYTE clone 015920 | 0 | 0 | |
| 186 | 15932 | 2 26 | H | I | U | U | U | | NCY015932 | | INCYTE clone 015932 | 0 | 0 | |
| 187 | 16004 | 2 26 | H | I | U | U | U | | NCY016004 | | INCYTE clone 016004 | 0 | 0 | |
| 188 | 16188 | 2 26 | H | I | U | U | U | | NCY016188 | | INCYTE clone 016188 | 0 | 0 | |
| 189 | 16210 | 2 26 | H | I | U | U | U | | NCY016210 | | INCYTE clone 016210 | 0 | 0 | |
| 190 | 16401 | 2 26 | H | I | U | U | U | | NCY016401 | | INCYTE clone 016401 | 0 | 0 | |
| 191 | 16554 | 2 26 | H | I | U | U | U | | NCY016554 | | INCYTE clone 016554 | 0 | 0 | |
| 192 | 16572 | 2 26 | H | I | U | U | U | | NCY016572 | | INCYTE clone 016572 | 0 | 0 | |
| 193 | 16625 | 2 26 | H | E | P | S | P | | HUMPAI | | Plasminogen activator inhibitor 1 | −880 | 0 | |
| 194 | 16635 | 2 26 | H | E | U | U | U | | HSPLAX | | PLA-X | 412 | 0 | |
| 195 | 16777 | 2 26 | H | E | C | C | Y | | HUMCAMPPK | | Protein kinase, cAMP-dependent, type 1a | −1172 | 0 | |
| 196 | 16951 | 2 26 | H | X | U | U | U | | HUM000S317 | | EST s317 (Okubo) | −150 | 0 | |
| 197 | 17024 | 2 26 | H | E | P | C | F | | HUMFERH | | Ferritin, heavy chain | 376 | 0 | |
| 198 | 17051 | 2 26 | H | I | U | U | U | | NCY017051 | | INCYTE clone 017051 | 0 | 0 | |

TABLE 2-continued

Clone numbers 15000 through 20000
Libraries: HUVEC
Designations: All
Condensed format analysis
Arranged by ABUNDANCE
Total clones represented: 5000
Total clones analyzed: 5000
l = library   d = designation   f = distribution   z = location   r = function   c = certain?   s = species
319 genes, for a total of 1713 clones

| Coincidence number | V | V Clones/10000 N | % | l | d | f | z | r | c | entry | s | descriptor | length | init | i |
|---|---|---|---|---|---|---|---|---|---|---|---|---|---|---|---|
| 199 | 17169 | 2 | 26 | H | I | U | U | U |   | NCY017169 |   | INCYTE clone 017169 | 0 | 0 |   |
| 200 | 17728 | 2 | 26 | H | E | C | C | R |   | HSHUMS3 |   | Ribosomal protein S3 | 721 | 0 |   |
| 201 | 17949 | 2 | 26 | H | I | U | U | U |   | NCY017949 |   | INCYTE clone 017949 | 0 | 0 |   |
| 202 | 18000 | 2 | 26 | H | E | P | S | S |   | HUMCONGRO |   | Growth factor, connective tissue | −55 | 0 |   |
| 203 | 18035 | 2 | 26 | H | E | C | K | K |   | HUMTUBAK |   | Tubulin, alpha | 947 | 0 |   |
| 204 | 18230 | 2 | 26 | H | I | U | U | U |   | NCY018230* |   | INCYTE clone 018230 | 0 | 0 |   |
| 205 | 18261 | 2 | 26 | H | E | C | C | R |   | HSRPL6AA |   | Ribosomal protein L6 | 481 | 0 |   |
| 206 | 18309 | 2 | 26 | H | E | C | K | K |   | HUMTRO |   | Tropomyosin | 73 | 0 |   |
| 207 | 18579 | 2 | 26 | H | O | C | C | M |   | RATODCAC | R | Ornithine decarboxylase antizyme | 1999 | 0 |   |
| 208 | 18696 | 2 | 26 | H | E | P | C | I |   | HSCYCR |   | Cyclophilin, T-cell | 292 | 0 |   |
| 209 | 18810 | 2 | 26 | H | O | U | U | U |   | MUSTUMSEQC | M | TNF-induced gene; poly A site | 867 | 0 |   |
| 210 | 18964 | 2 | 26 | H | I | U | U | U |   | NCY018964 |   | INCYTE clone 018964 | 0 | 0 |   |
| 211 | 19169 | 2 | 26 | H | I | U | U | U |   | NCY019169 |   | INCYTE clone 019169 | 0 | 0 |   |
| 212 | 19308 | 2 | 26 | H | E | C | N | D |   | HUMHISH3B |   | Histone H3.3 | 58 | 0 |   |
| 213 | 19309 | 2 | 26 | H | E | P | K | K |   | HUMMYLCB |   | Non-muscle myosin alkali lt. chain 3'e | 330 | 0 |   |
| 214 | 19362 | 2 | 26 | H | I | U | U | U |   | NCY019362 |   | INCYTE clone 019362 | 0 | 0 |   |
| 215 | 19712 | 2 | 26 | H | I | U | U | U |   | NCY019712 |   | INCYTE clone 019712 | 0 | 0 |   |
| 216 | 19787 | 2 | 26 | H | I | U | U | U |   | NCY019787 |   | INCYTE clone 019787 | 0 | 0 |   |
| 217 | 19901 | 2 | 26 | H | X | U | U | U |   | HSAFIC009 |   | EST FIc009 (Genexpress) | 0 | 0 |   |
| 218 | 15042 | 1 | 13 | H | O | C | C | R |   | XELRPL1BR | F | Ribosomal protein L1b | 931 | 0 |   |
| 219 | 15138 | 1 | 13 | H | E | P | S | S |   | S71513 |   | Chemotactic fctr MCAF, monocyte; MCP1 | 352 | 0 |   |
| 220 | 15160 | 1 | 13 | H | E | P | S | S |   | HUMIL1 |   | Interleukin-1 beta | 855 | 0 |   |
| 221 | 15168 | 1 | 13 | H | O | P | C | C |   | RABPCALG | B | Calgizzarin, lung | 290 | 0 |   |
| 222 | 15173 | 1 | 13 | H | E | C | N | T |   | HSRNPA1 |   | hnRNP core protein A1 | 470 | 0 |   |
| 223 | 15237 | 1 | 13 | H | E | U | E | B |   | HSKDEL |   | KDEL receptor | 265 | 0 |   |
| 224 | 15239 | 1 | 13 | H | X | U | U | U |   | M78695 |   | EST HHCMC28 (IGR) | 0 | 0 |   |
| 225 | 15320 | 1 | 13 | H | E | P | S | P |   | HUMCTSB |   | Cathepsin B | 829 | 0 |   |
| 226 | 15403 | 1 | 13 | H | X | U | U | U |   | HSAFIA044 |   | EST FIa044 (Genethon) | 0 | 0 |   |
| 227 | 15460 | 1 | 13 | H | E | C | C | E |   | HUMARF1BA |   | ADP-ribosylation factor 1 (ARF1) | 528 | 0 |   |
| 228 | 15512 | 1 | 13 | H | E | C | C | R |   | HUMS19RP |   | Ribosomal protein S19 | 440 | 0 |   |
| 229 | 15601 | 1 | 13 | H | X | U | U | U |   | HSAAACJWX |   | EST aaacjwx (UK-HGMP) | 0 | 0 |   |
| 230 | 15658 | 1 | 13 | H | E | C | C | R |   | HUMRPS6A |   | Ribosomal protein S6 | 767 | 0 |   |
| 231 | 15683 | 1 | 13 | H | E | C | E | B |   | HUMLCTHB |   | Clathrin, light chain-B | 239 | 0 |   |
| 232 | 15688 | 1 | 13 | H | O | C | M | Z |   | BOVATPS | V | ATP synthase gamma subunit | 2117 | 0 |   |
| 233 | 15753 | 1 | 13 | H | E | P | E | B |   | HUMCAM1V |   | Adhesion molecule VCAM1, vascular cell | 160 | 0 |   |
| 234 | 15771 | 1 | 13 | H | E | P | E | B |   | HUMLB2A26 |   | Laminin B2 chain | 0 | 0 |   |
| 235 | 15839 | 1 | 13 | H | E | U | U | S |   | S94424 |   | Cell adhesion regulator; CAR | 428 | 0 |   |
| 236 | 15853 | 1 | 13 | H | O | C | C | R |   | RNRPL28 | R | Ribosomal protein L28 | 407 | 0 |   |
| 237 | 15954 | 1 | 13 | H | E | P | Z | B |   | HSHPCP |   | Serglycin; sec granule proteoglycan cor | 463 | 0 |   |
| 238 | 15980 | 1 | 13 | H | E | C | C | Q |   | HUMBHAB |   | N-acetyl-beta-glucosaminidase | 1009 | 0 |   |
| 239 | 16123 | 1 | 13 | H | I | U | U | U |   | NCY015583 |   | INCYTE clone 015583 | 0 | 0 |   |
| 240 | 16136 | 1 | 13 | H | X | U | U | U |   | M78527 |   | EST 00675 (IGR) | 0 | 0 |   |
| 241 | 16170 | 1 | 13 | H | E | P | E | B |   | HUMHLAC |   | Human Leukocyte Antigen-C, class I | 235 | 0 |   |
| 242 | 16222 | 1 | 13 | H | E | C | U | Y |   | HUMCSISA |   | Oncogene cis | 0 | 0 |   |
| 243 | 16241 | 1 | 13 | H | E | C | C | E |   | HUMSAMS |   | S-adenosylmethionine synthetase | 1455 | 0 |   |
| 244 | 16299 | 1 | 13 | H | O | P | E | B |   | RATADRB | R | Adrenergic receptor, BTF protein | −774 | 0 |   |
| 245 | 16421 | 1 | 13 | H | X | U | U | U |   | M78858 |   | EST 01006 (IGR) | 0 | 0 |   |
| 246 | 16425 | 1 | 13 | H | E | U | U | H |   | HSDINFIG |   | Interferon inducible protein | −128 | 0 |   |
| 247 | 16498 | 1 | 13 | H | E | U | C | G |   | HUMRASAC |   | Oncogene ras-like protein | 433 | 2 |   |
| 248 | 16542 | 1 | 13 | H | X | U | U | U |   | HSAFIC082 |   | EST FIc082 (Genethon) | 0 | 0 |   |
| 249 | 16595 | 1 | 13 | H | O | P | Z | B |   | CFGPCR1 | D | G protein-coupled receptor | −314 | 1 |   |
| 250 | 16613 | 1 | 13 | H | E | C | C | N |   | HUMHPRTB |   | Hypoxanthine P-ribosyltransferase | 0 | 0 |   |
| 251 | 16622 | 1 | 13 | H | X | U | U | U |   | T03027 |   | EST FB20G3 (Sikela) | 0 | 0 |   |
| 252 | 16636 | 1 | 13 | H | E | P | U | Q |   | HUMSA |   | co-beta glucosidase, sulfatide activat | −478 | 0 |   |
| 253 | 16639 | 1 | 13 | H | E | C | C | U |   | HUMHLGPB5 |   | Lysosomal sialoglycoprotein | 1198 | 0 |   |
| 254 | 16669 | 1 | 13 | H | E | C | C | T |   | HUM4AI |   | initiation factor 4AI | 387 | 0 |   |
| 255 | 16884 | 1 | 13 | H | E | C | E | Q |   | HUMGLBA |   | co-beta glucosidase | −502 | 0 |   |
| 256 | 16892 | 1 | 13 | H | O | C | E | E |   | BOVIOPPP | V | Inorganic pyrophosphatase | 0 | 1 |   |
| 257 | 16897 | 1 | 13 | H | E | U | U | U |   | HSVIMENT |   | Vimentin; intermediate filament ptn | 31 | 0 |   |
| 258 | 16974 | 1 | 13 | H | E | C | C | R |   | HUMRPS14 |   | Ribosomal protein S14 | 3437 | 0 |   |
| 259 | 16983 | 1 | 13 | H | E | C | U | U |   | HLJMGRP78 |   | Glucose-regulated protein, 78 kDa | 2213 | 0 |   |
| 260 | 16988 | 1 | 13 | H | E | U | U | U |   | HUMEMS |   | Amplaxin, EMS1 gene | 487 | 0 |   |
| 261 | 17019 | 1 | 13 | H | E | C | C | R |   | HUMRGM |   | Ribosomal RNA, 28S | 3695 | 0 |   |
| 262 | 17151 | 1 | 13 | H | X | U | U | U |   | M77972 |   | EST HFBCF64 | 0 | 0 |   |
| 263 | 17159 | 1 | 13 | H | E | P | S | P |   | HUMCLI |   | Complement cytolysis inhibitor; apo J | 201 | 0 |   |
| 264 | 17175 | 1 | 13 | H | O | C | M | E |   | PIGACON | P | Aconitase, mitochondrial | 996 | 1 |   |

TABLE 2-continued

Clone numbers 15000 through 20000
Libraries: HUVEC
Designations: All
Condensed format analysis
Arranged by ABUNDANCE
Total clones represented: 5000
Total clones analyzed: 5000 l = library     d = designation     f = distribution     z = location     r = function     c = certain?     s = species
319 genes, for a total of 1713 clones

| Coincidence number | V number | V N | Clones/10000 % | l | d | f | z | r | c | entry | s | descriptor | length | init | i |
|---|---|---|---|---|---|---|---|---|---|---|---|---|---|---|---|
| 265 | 17175 | 1 | 13 | H | E | U | U | H |   | HUMIFN15K |   | Interferon-induced 17 kD/15 kD protein | 560 | 0 |   |
| 266 | 17184 | 1 | 13 | H | E | U | U | E |   | HSDHPR |   | Dihydropteridine reductase | 717 | 0 |   |
| 267 | 17254 | 1 | 13 | H | E | P | E | B |   | HUMB2M2 |   | Microglobulin, beta-2 | 0 | 0 |   |
| 268 | 17278 | 1 | 13 | H | E | P | E |   |   | HSCD59A |   | lymphocytic antigen CD59 | 268 | 0 |   |
| 269 | 17408 | 1 | 13 | H | H | U | U | D | ? | HSPHL1 |   | Oncogene myc; cytochrome c oxidase | 0 | 0 |   |
| 270 | 17438 | 1 | 13 | H | E | C | C | R |   | HUMRPSA3A |   | Ribosomal protein S3a; v-fos tf effect | 706 | 0 |   |
| 271 | 17459 | 1 | 13 | H | E |   |   |   | R | HSTRA1 |   | homologue of murine tumor rejection at | -15 | 0 |   |
| 272 | 17572 | 1 | 13 | H | E | P | S | S |   | HUMGRANUL |   | Granulin | 129 | 0 |   |
| 273 | 17642 | 1 | 13 | H | O | C | K | K |   | MMTALINR | M | Talin (cytoskeletal protein) | 180 | 0 |   |
| 274 | 17800 | 1 | 13 | H | E | C | N | D |   | HUMNSEP |   | Nuclease-sensitive element | -85 | 0 |   |
| 275 | 17871 | 1 | 13 | H | E | C | C | R |   | HSRPL32 |   | Ribosomal protein L32 | 299 | 0 |   |
| 276 | 18001 | 1 | 13 | H | E | C | U | O |   | HSRAPB1 |   | Rap 1B; ras-related oncogene | -88 | 0 |   |
| 277 | 18008 | 1 | 13 | H | E | P | C | I |   | HUMFABPHA |   | Fatty acid binding protein homologue | 439 | 0 |   |
| 278 | 18040 | 1 | 13 | H | E | C | E | C |   | HUMIP90 |   | Calnexin, integral membrane ptn IP90 | 143 | 0 |   |
| 279 | 18049 | 1 | 13 | H | E | P | E | B |   | HUMENDO |   | Endoglin, endothelial RGD-glycoprotein | 82 | 0 |   |
| 280 | 18214 | 1 | 13 | H | E | C | C | R |   | HSRP26AA |   | Ribosomal protein L26 | 437 | 0 |   |
| 281 | 18217 | 1 | 13 | H | X | U | U | U |   | M78700 |   | EST HHCMC44 (IGR) | 0 | 0 |   |
| 282 | 18220 | 1 | 13 | H | E | C | N | D |   | HSBTF3B |   | BTF 3B; transcription factor | 522 | 0 |   |
| 283 | 18311 | 1 | 13 | H | E | C | N | D |   | HUMNAP |   | Nucleosome assembly protein | 426 | 0 |   |
| 284 | 18313 | 1 | 13 | H | X | U | U | U |   | HSAAABQCB |   | EST AAABQCB (UK-HGMP) | 0 | 0 |   |
| 285 | 18414 | 1 | 13 | H | X | U | U | U |   | M78415 |   | EST HFBCB73 (Kerlavage) | 0 | 0 |   |
| 286 | 18446 | 1 | 13 | H | E | P | S | S |   | HSCSP40 |   | Complement cytolysis inhibitor SP40-40 | 198 | 0 |   |
| 287 | 18518 | 1 | 13 | H | E | C | C | E |   | HSGSTPI |   | Glutathione S-transferase | 633 | 0 |   |
| 288 | 18528 | 1 | 13 | H | E | C | C | L |   | HUMUBI13 |   | Ubiquitin | 1777 | 0 |   |
| 289 | 18532 | 1 | 13 | H | E | C | N | N |   | HUMAPE |   | Endonuclease, apurinic (APEX) | 621 | 0 |   |
| 290 | 18538 | 1 | 13 | H | E | C | U | U |   | HUMTHD |   | Thioredoxin | 353 | 0 |   |
| 291 | 18542 | 1 | 13 | H | E | P | U | U | ? | HUMIEF |   | Transformation-sens ptn IEF-SSP-3521 | 534 | 0 |   |
| 292 | 18630 | 1 | 13 | H | E | C | C | Z |   | HUMATPC |   | ADP/ATP carrier ptn | 400 | 0 |   |
| 293 | 18699 | 1 | 13 | H | E | C | U | D |   | HSRD |   | RD protein, RNA-binding, MHC class III | 481 | 0 |   |
| 294 | 18812 | 1 | 13 | H | X | U | U | U |   | M85505 |   | EST HFBCJ11 (Kerlavage) | 0 | 0 |   |
| 295 | 18899 | 1 | 13 | H | E | P | E | B | ? | HUMMUC18B |   | Glycoprotein MUC18; adhesion molecule | -596 | 0 |   |
| 296 | 18927 | 1 | 13 | H | E | U | U | H |   | HUMIFI16A |   | Interferon-gamma induced protein | -16 | 0 |   |
| 297 | 18985 | 1 | 13 | H | E | P | C | I |   | HUMCYCLO |   | Cyclophillin | 337 | 0 |   |
| 298 | 19003 | 1 | 13 | H | X | U | U | U |   | HSB20H022 |   | EST 20H02 (Genethon) | 0 | 0 |   |
| 299 | 19007 | 1 | 13 | H | E | C | C | R |   | HUMRPS17 |   | Ribosomal protein S17 | 287 | 0 |   |
| 300 | 19088 | 1 | 13 | H | E | C | C | R |   | HUMPPARP1 |   | Acidic ribosomal phosphoprotein P1 | 452 | 0 |   |
| 301 | 19145 | 1 | 13 | H | O | U | C | Y |   | RATERK3 | R | Kinase, extracellular signal-related | 0 | 0 |   |
| 302 | 19152 | 1 | 13 | H | X | C | C | R |   | M78040 |   | EST HHCMG86; ribosomal ptn L1a | 0 | 0 |   |
| 303 | 19188 | 1 | 13 | H | E | P | E | B |   | HUMMHBA123 |   | HLA protein, chicken B complex homolog | 1006 | 0 |   |
| 304 | 19195 | 1 | 13 | H | E | C | U | H |   | HUMHSP90 |   | Heat shock protein, 90-kDa | 916 | 0 |   |
| 305 | 19440 | 1 | 13 | H | E | P | S | E |   | HUMCN2 |   | Collagenase, skin | 1224 | 0 |   |
| 306 | 19459 | 1 | 13 | H | E |   |   |   |   | HUMGAPDR |   | Glyceraldehyde-3-phosphate dehydrogena | 760 | 0 |   |
| 307 | 19520 | 1 | 13 | H | X | U | U | U | R | HSAFIF047 |   | EST FIf047 (Genexpress) | 0 | 0 |   |
| 308 | 19542 | 1 | 13 | H | X | U | U | U |   | HSAAABIRO |   | EST AAABIRO (UK-HGMP) | 0 | 0 |   |
| 309 | 19614 | 1 | 13 | H | E | C | C | R |   | HUMPPARP0 |   | Acidic ribosomal phosphoprotein P0 | 733 | 0 |   |
| 310 | 19719 | 1 | 13 | H | O | U | C | C |   | MMCABIN | M | Calcium-binding protein | 337 | 1 |   |
| 311 | 19731 | 1 | 13 | H | O | U | U | U |   | MMI3RNA | M | I3 gene; specific expression pattern | 165 | 1 |   |
| 312 | 19738 | 1 | 13 | H | I | U | U | U |   | NCY018313 |   | INCYTE clone 018313 | 0 | 0 |   |
| 313 | 19811 | 1 | 13 | H | O | C | M | Z |   | BTNADHDUA | V | NADH dehydrogenase; ubiquinone | 309 | 0 |   |
| 314 | 19813 | 1 | 13 | H | X | U | U | U |   | HSB07A082 |   | EST 07A08 (Genexpress) | 0 | 0 |   |
| 315 | 19834 | 1 | 13 | H | E | C | C | R |   | HUMRPL7A |   | Ribosomal protein L7A; PLA-X; surf3 | 422 | 0 |   |
| 316 | 19918 | 1 | 13 | H | H | C | C | Y |   | HUMFAK |   | Kinase, focal adhesion; tyrosine kinase | -45 | 0 |   |
| 317 | 19953 | 1 | 13 | H | E | U | C | G |   | HSGIR |   | G (i) protein alpha-aubunit | -37 | 0 |   |
| 318 | 19955 | 1 | 13 | H | E | U | U | U |   | HSLLREP3 |   | LLrep3; repetitive DNA | 530 | 0 |   |
| 319 | 19963 | 1 | 13 | H | E | P | S | S |   | HUMVWFM |   | Von Willebrand factor, glycoprotein | 1008 | 0 | Z |

TABLE 3

NORMAL MONOCYTE VERSUS ACTIVATED MACROPHAGE
Top 15 Most Abundant Genes

| | Normal | Activated |
|---|---|---|
| 1 | Elongation factor-1 alpha | Interleukin-1 beta |
| 2 | Ribosomal phosphoprotein | Macrophage inflammatory protein-1 |
| 3 | Ribosomal protein S8 homolog | |
| 4 | Beta-Globin | Interleukin-8 |
| 5 | Ferritin H chain | Lymphocyte activation gene |
| 6 | Ribosomal protein L7 | Elongation factor-1 alpha |
| 7 | Nucleoplasmin | Beta actin |
| 8 | Ribosomal protein S20 homolog | Rantes T-cell specific protein |
| 9 | Transferrin receptor | Poky A binding protein |
| 10 | Poly-A binding protein | Osteopontin; nephropontin |
| 11 | Translationally controlled tumor ptn | Tumor Necrosis Factor-alpha |
| | | INCYTE clone 011050 |
| 12 | Ribosomal protein S25 | Cu/Zn superoxide dismutase |
| 13 | Signal recognition particle SRP9 | Adenylate cyclase (yeast homolog) |
| 14 | Histone H2A.Z | NGF-related B cell activation molecule |
| 15 | Ribosomal protein Ke-3 | Protease Nexin-1, glial-derived |

TABLE 4

01/25/94  16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes d = designation  f = distribution  z = location  r = function  s = species  i = interest
1057 genes, for a total of 2151 clones

| number | d | f | z | r | entry | s | descriptor | bgfreq | rfend | ratio | i |
|---|---|---|---|---|---|---|---|---|---|---|---|
| 10022 | E | P | S | S | HUMIL1 | | Interleukin 1-beta | 0 | 131 | 262.00 | 0 |
| 10036 | E | P | S | S | HSMDNCF | | Interleukin-8; neutrophil activat ptn | 0 | 119 | 238.00 | 0 |
| 10089 | E | P | S | S | HSLAG1CDN | | Lymphocyte activation gene LAG1; Act-2 | 0 | 71 | 142.00 | 0 |
| 10060 | E | P | S | S | HUMTCSM | | T-cell specific chemokine RANTES | 0 | 23 | 46.000 | 0 |
| 10003 | E | P | S | S | HUMMIP1A | | Macrophage inflammatory protein-1 | 3 | 121 | 40.333 | 0 |
| 10689 | E | P | C | C | HSOP | | Osteopontin; nephropontin | 0 | 20 | 40.000 | 0 |
| 11050 | I | U | U | U | NCY011050 | | INCYTE clone 011050 | 0 | 17 | 34.000 | 0 |
| 10937 | E | P | S | S | HSTNFR | | TNF-alpha | 0 | 17 | 34.000 | 0 |
| 10176 | E | P | C | E | HSSOD | | Superoxide dismutase, Cu/Zn | 0 | 14 | 28.000 | 0 |
| 10886 | E | P | E | B | HSCDW40 | | B-cell activation molecule, NGF-relate | 0 | 10 | 20.000 | 0 |
| 10186 | E | P | U | H | HUMAPR | | Immediate early response PMA-ind gene | 0 | 9 | 18.000 | 0 |
| 10967 | E | P | S | P | HUMGDN | | Protease nexin-1, glial-derived | 0 | 9 | 18.000 | 0 |
| 11353 | I | U | U | U | NCY011353 | | INCYTE clone 011353 | 0 | 8 | 16.000 | 0 |
| 10298 | I | U | U | U | NCY010298 | | INCYTE clone 010298 | 0 | 7 | 14.000 | 0 |
| 10215 | E | P | S | P | HUM4COLA | | Collagenase type IV | 0 | 6 | 12.000 | 0 |
| 10276 | I | U | U | U | NCY010276 | | INCYTE clone 010276 | 0 | 6 | 12.000 | 0 |
| 10488 | I | U | U | U | NCY010488 | | INCYTE clone 010488 | 0 | 6 | 12.000 | 0 |
| 11138 | I | U | U | U | NCY011138 | | INCYTE clone 011138 | 0 | 6 | 12.000 | 2 |
| 10037 | E | P | C | E | HUMCAPPRO | | Adenylate cyclase-assoc ptn (CAP) | 1 | 10 | 10.000 | 0 |
| 10840 | E | C | C | E | HUMADCY | | Adenylyl cyclase-assoc protein | 0 | 5 | 10.000 | 0 |
| 10672 | E | P | E | B | HSCD44E | | Cell adhesion glycoprotein CD44 | 0 | 5 | 10.000 | 0 |
| 12837 | E | P | C | W | HUMCYCLOX | | Cyclooxygenase-2 | 0 | 5 | 10.000 | 0 |
| 10001 | I | U | U | U | NCY010001 | | INCYTE clone 010001 | 0 | 5 | 10.000 | 0 |
| 10005 | I | U | U | U | NCY010005 | | INCYTE clone 010005 | 0 | 5 | 10.000 | 0 |
| 10294 | I | U | U | U | NCY010294 | | INCYTE clone 010294 | 0 | 5 | 10.000 | 0 |
| 10297 | I | U | U | U | NCY010297 | | INCYTE clone 010297 | 0 | 5 | 10.000 | 0 |
| 10403 | I | U | U | U | NCY010403 | | INCYTE clone 010403 | 0 | 5 | 10.000 | 0 |
| 10699 | Z | U | U | U | NCY010699 | | INCYTE clone 010699 | 0 | 5 | 10.000 | 0 |
| 10966 | I | U | U | U | NCY010966 | | INCYTE clone 010966 | 0 | 5 | 10.000 | 0 |
| 12092 | I | U | U | U | NCY012092 | | INCYTE clone 012092 | 0 | 5 | 10.000 | 0 |
| 12549 | E | C | N | O | HSRHOB | | Oncogene rho | 0 | 5 | 10.000 | 0 |
| 10691 | E | C | C | E | HUMARF1BA | | ADP-ribosylation factor 1 (ARF1) | 0 | 4 | 8.000 | 0 |
| 12106 | E | C | C | E | HSADSS | | Adenylosuccinate synthetase | 0 | 4 | 8.000 | 0 |
| 10194 | E | P | S | P | HSCATHL | | Cathepsin L (Major Excreted Protein) | 0 | 4 | 8.000 | 0 |
| 10479 | O | C | C | S | CLMCYCA | I | Cyclin A (cell cycle inducer) | 0 | 4 | 8.000 | 1 |
| 10031 | I | U | U | U | NCY010031 | | INCYTE clone 010031 | 0 | 4 | 8.000 | 0 |
| 10203 | I | U | U | U | NCY010203 | | INCYTE clone 010203 | 0 | 4 | 8.000 | 0 |

TABLE 4-continued

01/25/94   16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes d = designation   f = distribution   z = location   r = function   s = species   i = interest
1057 genes, for a total of 2151 clones

| number | d | f | z | r | entry | s | descriptor | bgfreq | rfend | ratio | i |
|---|---|---|---|---|---|---|---|---|---|---|---|
| 10288 | I | U | U | U | NCY010288 | | INCYTE clone 010288 | 0 | 4 | 8.000 | 0 |
| 10372 | Z | U | U | U | NCY010372 | | INCYTE clone 010372 | 0 | 4 | 8.000 | 0 |
| 10411 | I | U | U | U | NCY010471 | | INCYTE clone 010471 | 0 | 4 | 8.000 | 0 |
| 10484 | I | U | U | U | NCY010484 | | INCYTE clone 010484 | 0 | 4 | 8.000 | 0 |
| 10859 | I | U | U | U | NCY010859 | | INCYTE clone 010859 | 0 | 4 | 8.000 | 0 |
| 10890 | I | U | U | U | NCY010890 | | INCYTE clone 010890 | 0 | 4 | 8.000 | 0 |
| 11511 | I | U | U | U | NCY011511 | | INCYTE clone 011511 | 0 | 4 | 8.000 | 0 |
| 11868 | I | U | U | U | NCY011868 | | INCYTE clone 011868 | 0 | 4 | 8.000 | 0 |
| 12820 | I | U | U | U | NCY012820 | | INCYTE clone 012820 | 0 | 4 | 8.000 | 0 |
| 10133 | E | P | S | S | HSI1RAP | | Interleukin-1 antagonist, IRAP | 0 | 4 | 8.000 | 0 |
| 10516 | E | P | C | Y | HUMP2A | | Phosphatase, regulatory subunit 2A | 0 | 4 | 8.000 | 0 |
| 11063 | E | P | U | H | HUMB94 | | TNF-inducible primary response gene | 0 | 4 | 8.000 | 0 |
| 11140 | E | P | E | B | HSHB15RNA | | HB15 gene; new Ig superfamily member | 0 | 3 | 6.000 | 0 |
| 10788 | I | U | U | U | NCY001713 | | INCYTE clone 01713 | 0 | 3 | 6.000 | 0 |
| 10033 | I | U | U | U | NCY010033 | | INCYTE clone 10033 | 0 | 3 | 6.000 | 0 |
| 10035 | I | U | U | U | NCY010035 | | INCYTE clone 10035 | 0 | 3 | 6.000 | 0 |
| 10084 | I | U | U | U | NCY010084 | | INCYTE clone 10084 | 0 | 3 | 6.000 | 0 |
| 10236 | I | U | U | U | NCY010236 | | INCYTE clone 10236 | 0 | 3 | 6.000 | 0 |
| 10383 | I | U | U | U | NCY010383 | | INCYTE clone 10383 | 0 | 3 | 6.000 | 0 |
| 10450 | I | U | U | U | NCY010450 | | INCYTE clone 10450 | 0 | 3 | 6.000 | 0 |
| 10470 | I | U | U | U | NCY010470 | | INCYTE clone 10470 | 0 | 3 | 6.000 | 0 |
| 10504 | I | U | U | U | NCY010504 | | INCYTE clone 10504 | 0 | 3 | 6.000 | 0 |
| 10507 | I | U | U | U | NCY010507 | | INCYTE clone 10507 | 0 | 3 | 6.000 | 0 |
| 10598 | I | U | U | U | NCY010598 | | INCYTE clone 10598 | 0 | 3 | 6.000 | 0 |
| 10799 | I | U | U | U | NCY010779 | | INCYTE clone 10779 | 0 | 3 | 6.000 | 0 |
| 10909 | I | U | U | U | NCY010909 | | INCYTE clone 10909 | 0 | 3 | 6.000 | 0 |
| 10976 | I | U | U | U | NCY010976 | | INCYTE clone 10976 | 0 | 3 | 6.000 | 0 |
| 10985 | I | U | U | U | NCY010985 | | INCYTE clone 10985 | 0 | 3 | 6.000 | 0 |
| 11052 | I | U | U | U | NCY011052 | | INCYTE clone 11052 | 0 | 3 | 6.000 | 0 |
| 11068 | I | U | U | U | NCY011068 | | INCYTE clone 11068 | 0 | 3 | 6.000 | 0 |
| 11134 | I | U | U | U | NCY011134 | | INCYTE clone 11134 | 0 | 3 | 6.000 | 0 |
| 11136 | I | U | U | U | NCY011136 | | INCYTE clone 11136 | 0 | 3 | 6.000 | 0 |
| 11191 | I | U | U | U | NCY011191 | | INCYTE clone 11191 | 0 | 3 | 6.000 | 0 |
| 11219 | I | U | U | U | NCY011219 | | INCYTE clone 11219 | 0 | 3 | 6.000 | 0 |
| 11386 | I | U | U | U | NCY011386 | | INCYTE clone 11386 | 0 | 3 | 6.000 | 0 |
| 11403 | I | U | U | U | NCY011403 | | INCYTE clone 011403 | 0 | 3 | 6.000 | 0 |
| 11460 | I | U | U | U | NCY011460 | | INCYTE clone 011460 | 0 | 3 | 6.000 | 0 |
| 11618 | I | U | U | U | NCY011618 | | INCYTE clone 011618 | 0 | 3 | 6.000 | 0 |
| 11686 | I | U | U | U | NCY011686 | | INCYTE clone 011686 | 0 | 3 | 6.000 | 0 |
| 12021 | I | U | U | U | NCY012021 | | INCYTE clone 012021 | 0 | 3 | 6.000 | 0 |
| 12025 | I | U | U | U | NCY012025 | | INCYTE clone 012025 | 0 | 3 | 6.000 | 0 |
| 12320 | I | U | U | U | NCY012320 | | INCYTE clone 012320 | 0 | 3 | 6.000 | 0 |
| 12330 | I | U | U | U | NCY012330 | | INCYTE clone 012330 | 0 | 3 | 6.000 | 0 |
| 12853 | I | U | U | U | NCY012853 | | INCYTE clone 012853 | 0 | 3 | 6.000 | 0 |
| 14386 | I | U | U | U | NCY014386 | | INCYTE clone 014386 | 0 | 3 | 6.000 | 0 |
| 14391 | I | U | U | U | NCY014391 | | INCYTE clone 014391 | 0 | 3 | 6.000 | 0 |
| 14795 | I | U | U | U | NCY014795 | | INCYTE clone 014795 | 0 | 3 | 6.000 | 0 |
| 11165 | E | P | C | C | HUMLIC | | Lipocortin II | 0 | 3 | 6.000 | 0 |
| 12006 | O | P | S | P | CHKHIMP3A | C | Metalloproteinase inhibitor TIMP-3 | 0 | 3 | 6.000 | 4 |
| 13363 | E | P | U | A | HUMMGC24 | | Mucin, gastric carcinoma epithelial | 0 | 3 | 6.000 | 0 |
| 11112 | O | C | C | Q | DOGOST48A | D | Oligosaccharyltransferase, 48 kDa | 0 | 3 | 6.000 | 3 |
| 10847 | E | P | E | D | HSETS23 | | Oncogene ETS2 | 0 | 3 | 6.000 | 0 |
| 11426 | E | C | U | O | HSRAB2 | | Oncogene rab-2; ras, YPT1-related ptn | 0 | 3 | 6.000 | 0 |
| 10153 | E | U | U | U | HSPM5 | | PM5 (collagenase homolog?) | 0 | 3 | 6.000 | 0 |
| 12083 | E | C | K | K | HSPGSR | | Plasma gelsolin | 0 | 3 | 6.000 | 0 |
| 11330 | H | P | U | U | HUM22SM | | Smooth muscle senescent ptn, 22 kDa | 0 | 3 | 6.000 | 3 |
| 12630 | E | P | S | S | HSTNFABX | | TNF a/b gene (noncoding) | 0 | 3 | 6.000 | 0 |
| 13104 | E | P | N | D | HUMISGF3A | | Transcription factor ISGF-3 | 0 | 3 | 6.000 | 0 |
| 11312 | E | P | E | B | HSUPARAA | | Urokinase plasminogen act surf receptg | 0 | 3 | 6.000 | 0 |
| 10513 | E | P | E | B | HUMVDAC1X | | Voltage-dep anion channel, isoform 1 | 0 | 3 | 6.000 | 0 |
| 10503 | E | U | N | D | HUMHXBP1 | | X box binding protein XBP-1 | 0 | 3 | 6.000 | 0 |
| 10199 | E | C | C | F | HUMFERL | | Ferritin, light chain | 3 | 13 | 4.333 | 0 |
| 10653 | E | P | S | P | HSTIMPR | | Metalloproteinase inhibitor TIMP-1 | 1 | 4 | 4.000 | 0 |
| 14741 | E | C | E | C | HUMHO2A | | ATPase calcium pump | 0 | 2 | 4.000 | 0 |
| 13018 | E | C | U | Z | HUMPMPCA | | ATPase, calcium pumping | 0 | 2 | 4.000 | 0 |

TABLE 4-continued

01/25/94  16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes d = designation   f = distribution   z = location   r = function   s = species   i = interest 1057 genes, for a total of 2151 clones

| number | d | f | z | r | entry | s | descriptor | bgfreq | rfend | ratio | i |
|---|---|---|---|---|---|---|---|---|---|---|---|
| 13326 | E | C | C | G | HSGSA1R | | Adenyl cyclase coupling ptn G(s)-A-S1 | 0 | 2 | 4.000 | 1 |
| 11869 | E | P | S | P | HSAMPEPN | | Aminopeptidase N, intestinal; CD13 | 0 | 2 | 4.000 | 0 |
| 10477 | E | P | S | P | HUMCATS | | Cathepsin S, elastinolytic Cys proteas | 0 | 2 | 4.000 | 0 |
| 14888 | O | S | E | K | RATCARHC | R | Clathrin, heavy chain | 0 | 2 | 4.000 | 0 |
| 11577 | E | C | Z | L | HSDOCKP | | Docking protein, signal recognition | 0 | 2 | 4.000 | 0 |
| 12893 | O | C | C | Q | CRUACAPT | S | GlcNac-1-PO4 transferase | 0 | 2 | 4.000 | 3 |
| 10826 | E | C | N | D | HSHMGY | | High mobility group protein; Y/I | 0 | 2 | 4.000 | 0 |
| 10798 | E | P | N | T | HUMSRP20 | | HnRNA splicing factor 20 (SRp20) | 0 | 2 | 4.000 | 0 |
| 12347 | I | U | U | U | NCY000942 | | INCYTE clone 000942 | 0 | 2 | 4.000 | 0 |
| 11317 | I | U | U | U | NCY001367 | | INCYTE clone 001367 | 0 | 2 | 4.000 | 0 |
| 10013 | I | U | U | U | NCY010013 | | INdYTE clone 010013 | 0 | 2 | 4.000 | 0 |
| 10018 | I | U | U | U | NCY010018 | | INCYTE clone 010018 | 0 | 2 | 4.000 | 0 |
| 10086 | I | U | U | U | NCY010086 | | INCYTE clone 010086 | 0 | 2 | 4.000 | 0 |
| 10092 | I | U | U | U | NCY010092 | | INCYTE clone 010092 | 0 | 2 | 4.000 | 0 |
| 10137 | I | U | U | U | NCY010137 | | INCYTE clone 010137 | 0 | 2 | 4.000 | 0 |
| 10213 | I | U | U | U | NCY010213 | | INCYTE clone 010213 | 0 | 2 | 4.000 | 0 |
| 10214 | I | U | U | U | NCY010214 | | INCYTE clone 010214 | 0 | 2 | 4.000 | 0 |
| 10285 | I | U | U | U | NCY010285 | | INCYTE clone 010285 | 0 | 2 | 4.000 | 0 |
| 10290 | I | U | U | U | NCY010290 | | INCYTE clone 010290 | 0 | 2 | 4.000 | 0 |
| 10291 | I | U | U | U | NCY010291 | | INCYTE clone 010291 | 0 | 2 | 4.000 | 0 |
| 10386 | I | U | U | U | NCY010386 | | INCYTE clone 016386 | 0 | 2 | 4.000 | 0 |
| 10410 | I | U | U | U | NCY010410 | | INCYTE clone 010410 | 0 | 2 | 4.000 | 0 |
| 10419 | I | U | U | U | NCY010419 | | INCYTE clone 010419 | 0 | 2 | 4.000 | 0 |
| 10459 | I | U | U | U | NCY010459 | | INCYTE clone 010459 | 0 | 2 | 4.000 | 0 |
| 10469 | I | U | U | U | NCY010469 | | INCYTE clone 010469 | 0 | 2 | 4.000 | 0 |
| 10621 | I | U | U | U | NCY010621 | | INCYTE clone 010621 | 0 | 2 | 4.000 | 0 |
| 10649 | I | U | U | U | NCY010649 | | INCYTE clone 010649 | 0 | 2 | 4.000 | 0 |
| 10863 | I | U | U | U | NCY010863 | | INCYTE clone 010863 | 0 | 2 | 4.000 | 0 |
| 10907 | I | U | U | U | NCY010907 | | INCYTE clone 010907 | 0 | 2 | 4.000 | 0 |
| 10914 | I | U | U | U | NCY010914 | | XNCYTE clone 010914 | 0 | 2 | 4.000 | 0 |
| 10936 | I | U | U | U | NCY010936 | | INCYTE clone 010936 | 0 | 2 | 4.000 | 0 |
| 10982 | I | U | U | U | NCY010982 | | INCYTE clone 010982 | 0 | 2 | 4.000 | 0 |
| 11032 | I | U | U | U | NCY011032 | | INCYTE clone 011032 | 0 | 2 | 4.000 | 0 |
| 11041 | I | U | U | U | NCY011041 | | INCYTE clone 011041 | 0 | 2 | 4.000 | 0 |
| 11045 | I | U | U | U | NCY011045 | | INCYTE clone 011045 | 0 | 2 | 4.000 | 0 |
| 11048 | I | U | U | U | NCY011048 | | INCYTE clone 011048 | 0 | 2 | 4.000 | 0 |
| 11055 | I | U | U | U | NCY011055 | | INCYTE clone 011055 | 0 | 2 | 4.000 | 0 |
| 11059 | I | U | U | U | NCY011059 | | INCYTE clone 011059 | 0 | 2 | 4.000 | 0 |
| 11129 | I | U | U | U | NCY011129 | | INCYTE clone 011129 | 0 | 2 | 4.000 | 0 |
| 11148 | I | U | U | U | NCY011148 | | INCYTE clone 011148 | 0 | 2 | 4.000 | 0 |
| 11260 | I | U | U | U | NCY011260 | | INCYTE clone 011260 | 0 | 2 | 4.000 | 0 |
| 11316 | I | U | U | U | NCY011316 | | INCYTE clone 011316 | 0 | 2 | 4.000 | 0 |
| 11375 | I | U | U | U | NCY011375 | | INCYTE clone 011375 | 0 | 2 | 4.000 | 0 |
| 11383 | I | U | U | U | NCY011383 | | INCYTE clone 011383 | 0 | 2 | 4.000 | 0 |
| 11388 | I | U | U | U | NCY011388 | | INCYTE clone 0.11388 | 0 | 2 | 4.000 | 0 |
| 11390 | I | U | U | U | NCY011390 | | INCYTE clone 011390 | 0 | 2 | 4.000 | 0 |
| 11436 | I | U | U | U | NCY011436 | | INCYTE clone 011436 | 0 | 2 | 4.000 | 0 |
| 11483 | I | U | U | U | NCY011483 | | INCYTE clone 011483 | 0 | 2 | 4.000 | 0 |
| 11519 | I | U | U | U | NCY011519 | | INCYTE clone 011519 | 0 | 2 | 4.000 | 0 |
| 11520 | I | U | U | U | NCY011520 | | INCYTE clone 011520 | 0 | 2 | 4.000 | 0 |
| 11556 | I | U | U | U | NCY011556 | | INCYTE clone 011556 | 0 | 2 | 4.000 | 0 |
| 11614 | I | U | U | U | NCY011614 | | INCYTE clone 011614 | 0 | 2 | 4.000 | 0 |
| 11629 | I | U | U | U | NCY011629 | | INCYTE clone 011629 | 0 | 2 | 4.000 | 0 |
| 11695 | I | U | U | U | NCY011695 | | INCYTE cyclone 011695 | 0 | 2 | 4.000 | 0 |
| 11744 | I | U | U | U | NCY011744 | | INCYTE clone 011744 | 0 | 2 | 4.000 | 0 |
| 11777 | I | U | U | U | NCY011777 | | INCYTE clone 011777 | 0 | 2 | 4.000 | 0 |
| 11848 | I | U | U | U | NCY011848 | | INCYTE clone 011848 | 0 | 2 | 4.000 | 0 |
| 12058 | I | U | U | U | NCY012058 | | INCYTE clone 012058 | 0 | 2 | 4.000 | 0 |
| 12072 | I | U | U | U | NCY012072 | | INCYTE clone 012072 | 0 | 2 | 4.000 | 0 |
| 12420 | I | U | U | U | NCY012420 | | INCYTE clone 012420 | 0 | 2 | 4.000 | 0 |
| 12466 | I | U | U | U | NCY012466 | | INCYTE clone 012466 | 0 | 2 | 4.000 | 0 |
| 12548 | I | U | U | U | NCY012548 | | INCYTE clone 012548 | 0 | 2 | 4.000 | 0 |
| 12802 | I | U | U | U | NCY012802 | | INCYTE clone 012802 | 0 | 2 | 4.000 | 0 |
| 12803 | I | U | U | U | NCY012803 | | INCYTE clone 012803 | 0 | 2 | 4.000 | 0 |
| 12813 | I | U | U | U | NCY012813 | | INCYTE clone 012813 | 0 | 2 | 4.000 | 0 |

TABLE 4-continued

01/25/94  16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes d = designation   f = distribution   z = location   r = function   s = species   i = interest 1057 genes, for a total of 2151 clones

| number | d | f | z | r | entry | s | descriptor | bgfreq | rfend | ratio | i |
|---|---|---|---|---|---|---|---|---|---|---|---|
| 12824 | I | U | U | U | NCY012824 |   | INCYTE clbne 012824 | 0 | 2 | 4.000 | 0 |
| 12881 | I | U | U | U | NCY012881 |   | INCYTE clone 012881 | 0 | 2 | 4.000 | 0 |
| 12902 | I | U | U | U | NCY012902 |   | INCYTE clone 012902 | 0 | 2 | 4.000 | 0 |
| 12960 | I | U | U | U | NCY012960 |   | INCYTE clone 012960 | 0 | 2 | 4.000 | 0 |
| 13027 | I | U | U | U | NCY013027 |   | INCYTE clone 013027 | 0 | 2 | 4.000 | 0 |
| 13120 | I | U | U | U | NCY013120 |   | INCYTE clone 013120 | 0 | 2 | 4.000 | 0 |
| 13156 | I | U | U | U | NCY013156 |   | INCYTE clone 013156 | 0 | 2 | 4.000 | 0 |
| 13165 | I | U | U | U | NCY013165 |   | INCYTE clone 013165 | 0 | 2 | 4.000 | 0 |
| 13174 | I | U | U | U | NCY013174 |   | INCYTE clone 013174 | 0 | 2 | 4.000 | 0 |
| 13284 | I | U | U | U | NCY013284 |   | INCYTE clone 013284 | 0 | 2 | 4.000 | 0 |
| 13517 | I | U | U | U | NCY013517 |   | INCYTE clone 013517 | 0 | 2 | 4.000 | 0 |
| 13567 | I | U | U | U | NCY013567 |   | INCYTE clone 013567 | 0 | 2 | 4.000 | 0 |
| 11690 | I | U | U | U | NCY013690 |   | INCYTE clone 013690 | 0 | 2 | 4.000 | 0 |
| 13899 | I | U | U | U | NCY013899 |   | INCYTE clone 013899 | 0 | 2 | 4.000 | 0 |
| 13903 | I | U | U | U | NCY013903 |   | INCYTE clone 013903 | 0 | 2 | 4.000 | 0 |
| 14057 | I | U | U | U | NCY014057 |   | INCYTE clone 014057 | 0 | 2 | 4.000 | 0 |
| 14130 | I | U | U | U | NCY014130 |   | INCYTE clone 014130 | 0 | 2 | 4.000 | 0 |
| 14161 | I | U | U | U | NCY014161 |   | INCYTE clone 014161 | 0 | 2 | 4.000 | 0 |
| 14179 | I | U | U | U | NCY014179 |   | INCYTE clone 014179 | 0 | 2 | 4.000 | 0 |
| 14185 | I | U | U | U | NCY014185 |   | INCYTE clone 014185 | 0 | 2 | 4.000 | 0 |
| 14306 | I | U | U | U | NCY014308 |   | INCYTE clone 014308 | 0 | 2 | 4.000 | 0 |
| 14314 | I | U | U | U | NCY014314 |   | INCYTE clone 014314 | 0 | 2 | 4.000 | 0 |
| 11542 | I | U | U | U | NCY014542 |   | INCYTE clone 014542 | 0 | 2 | 4.000 | 0 |
| 14573 | I | U | U | U | NCY014573 |   | INCYTE clone 014573 | 0 | 2 | 4.000 | 0 |
| 14853 | I | U | U | U | NCY014853 |   | INCYTE clone 014853 | 0 | 2 | 4.000 | 0 |
| 12710 | E | P | U | H | HUMISG2 |   | Interferonstimulated gene; ISG-54K | 0 | 2 | 4.000 | 0 |
| 10190 | E | P | E | B | HUMLAP |   | Leukocyte adhesicn ptn LFA-1/Mac-1 | 0 | 2 | 4.000 | 0 |
| 11167 | O | P | E | B | MMMACR |   | Macrosialin, lamp/lpg glycoptn family | 0 | 2 | 4.000 | 3 |
| 10861 | O | P | U | U | RATNP25GN | R | Neuronal protein NP25 | 0 | 2 | 4.000 | 2 |
| 13085 | E | P | C | G | HSRHOG |   | Oncogene rhoG GTpase, ras family member | 0 | 2 | 4.000 | 0 |
| 13358 | E | P | S | P | HUMPAI2 |   | Plasminogen activator inhibitor | 0 | 2 | 4.000 | 0 |
| 12858 | E | C | C | Y | HSPKA |   | Protein kinase, cAMP-dependent | 0 | 2 | 4.000 | 0 |
| 13177 | O | U | C | Y | S90449 |   | Protein phosphatase 2C | 0 | 2 | 4.000 | 1 |
| 10508 | E | C | C | N | HSPNP |   | Purine nucleoside phosphorylase | 0 | 2 | 4.000 | 0 |
| 11415 | O | C | C | T | DOGSEC61A | D | SEC61 homologue (rib-assoc ptn) | 0 | 2 | 4.000 | 0 |
| 11245 | E | U | N | D | M28372 |   | Sterol DNA-binding protein | 0 | 2 | 4.000 | 0 |
| 11954 | E | U | U | U | HSHSP1 |   | Synaptophysin related protein, H-Sp1 | 0 | 2 | 4.000 | 0 |
| 10786 | E | C | C | T | HUMWRSAA |   | TRNA synthetase, tryptophanyl; IFPS3 | 0 | 2 | 4.000 | 0 |
| 12042 | E | C | N | D | HUMTFIID |   | Transcription factor IID; TATA bdg ptn | 0 | 2 | 4.000 | 0 |
| 11121 | E | C | C | T | HUMEIF2A |   | Translational initiation factor eIF-2 | 0 | 2 | 4.000 | 0 |
| 13074 | E | P | K | K | HSTM30R |   | Tropomyoain TM30, fibroblaat | 0 | 2 | 4.000 | 0 |
| 10657 | E | C | K | K | HSVIMENT |   | Vimentin; intermediate filament ptn | 0 | 2 | 4.000 | 0 |
| 12856 | E | P | C | X | HSPLE |   | Pleckstrin (p47); pkc substtate | 2 | 7 | 3.500 | 0 |
| 10485 | E | P | E | B | HSMGLO |   | Microglobulin, beta-2- | 1 | 3 | 3.000 | 0 |
| 10990 | E | P | N | D | HUMMAD3A |   | Monocyte IkB-like activity, MAD-3 | 1 | 3 | 3.000 | 0 |
| 10927 | E | C | C | R | HSRPL6AA |   | Ribosomal protein L6 | 1 | 3 | 3.000 | 0 |
| 11489 | E | C | C | Y | HUMLYN |   | Tyrosine kinase, lyn B | 1 | 3 | 3.000 | 0 |
| 10293 | E | C | C | T | HSPOLYAB |   | Binding protein, polyadenylate | 7 | 20 | 2.857 | 0 |
| 10392 | E | P | C | Q | HUMPKM2L |   | Pyruvate kinase; thyroid hormone bnd pt | 3 | 7 | 2.333 | 0 |
| 12627 | E | P | C | S | HUMP6S |   | Plastin,T-, phosphoprotein (65 Kd) | 2 | 4 | 2.000 | 1 |
| 10438 | E | P | N | D | HUMYB1A |   | Y box binding ptn-1/DNA binding ptn B | 2 | 4 | 2.000 | 0 |
| 11132 | E | C | E | Q | HUMSA |   | Co-beta glucosidase | 1 | 2 | 2.000 | 0 |
| 12731 | E | P | C | E | HUMENOA |   | Enolase, alpha (non-neuronal) | 1 | 2 | 2.000 | 0 |
| 10995 | E | P | C | E | HUMGLP |   | Glutathione peroxidase; rhoh12 | 1 | 2 | 2.000 | 0 |
| 13521 | E | C | N | D | HSHMGI |   | High mobility group-1 protein; HMG-1 | 1 | 2 | 2.000 | 0 |
| 13682 | E | C | U | U | HSRIBIIR |   | Ribophorin II | 1 | 2 | 2.000 | 0 |
| 10694 | E | C | C | Z | HUMATPC |   | ADP/ATP carrier ptn | 0 | 1 | 2.000 | 0 |
| 13320 | O | C | M | Z | M24103 | V | ADP/ATP translocase, mt, T1 & T2 | 0 | 1 | 2.000 | 0 |
| 13324 | E | U | U | U | HUMTRLALL1 |   | ALL-1 gene (chromosome 4) | 0 | 1 | 2.000 | 0 |
| 14446 | E | C | C | N | HUMAMPD2 |   | AMP deaminase isoform L | 0 | 1 | 2.000 | 0 |
| 11735 | E | C | M | Z | HSATPF1M |   | ATP synthase F1; alpha subunit, mt | 0 | 1 | 2.000 | 0 |
| 13338 | E | C | C | N | HUMHK1A |   | ATPase, Ca++ | 0 | 1 | 2.000 | 0 |
| 14468 | O | C | K | K | D12816 | V | Actin 2 | 0 | 1 | 2.000 | 0 |
| 13943 | E | P | U | O | HUMAML1BP |   | Acute myeloid leukemia mRNA | 0 | 1 | 2.000 | 1 |
| 14590 | O | C | C | E | RATADCY3 | R | Adenylyl cyclase, type III | 0 | 1 | 2.000 | 0 |

TABLE 4-continued

01/25/94   16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes
d = designation   f = distribution   z = location   r = function   s = species   i = interest
1057 genes, for a total of 2151 clones

| number | d | f | z | r | entry | s | descriptor | bgfreq | rfend | ratio | i |
|---|---|---|---|---|---|---|---|---|---|---|---|
| 10134 | E | C | C | Q | HSALDAR |   | Aldolase A | 0 | 1 | 2.000 | 0 |
| 10202 | E | C | C | Q | HUMALDC |   | Aldolase C | 0 | 1 | 2.000 | 0 |
| 13559 | E | C | C | Q | HSALRE |   | Aldose reductase | 0 | 1 | 2.000 | 0 |
| 13817 | O | P | E | B | RNBCOP | R | B-COP, non-clathrin coated vessicle pt | 0 | 1 | 2.000 | 2 |
| 14967 | E | P | S | S | HSBSF2 |   | B-cell stimulatory factor-2 | 0 | 1 | 2.000 | 0 |
| 10502 | E | P | E | B | HUMMAC2 |   | B-gal binding lectin, 29 kDa; Mac-2 | 0 | 1 | 2.000 | 0 |
| 11066 | O | P | C | E | RATBRED | R | Biliverdin reductase | 0 | 1 | 2.000 | 3 |
| 13898 | E | C | C | L | HUMCBP |   | Binding protein, 5'-cap | 0 | 1 | 2.000 | 0 |
| 14850 | O | U | C | C | MUSRCA1 |   | Binding protein, ER-Ca | 0 | 1 | 2.000 | 0 |
| 14595 | O | P | U | U | MMF41RNA | M | Brain-specific cDNA clone F41 | 0 | 1 | 2.000 | 1 |
| 13029 | E | U | U | U | HSBCR |   | Break point cluster cDNA | 0 | 1 | 2.000 | 0 |
| 12622 | E | C | C | E | HUMCAMPHOS |   | CAMP phosphodiesterase | 0 | 1 | 2.000 | 0 |
| 11205 | E | U | U | U | HUMHDABCD |   | CDNA match to three cosmids | 0 | 1 | 2.000 | 0 |
| 13826 | E | U | U | U | HSAAABMEZ |   | CDNA of unknown function | 0 | 1 | 2.000 | 0 |
| 10139 | E | P | C | Y | HUMCSK2B |   | Casein kinase II beta | 0 | 1 | 2.000 | 0 |
| 14582 | E | P | S | P | HUMCTSB |   | Cathepsin B (homolog?) | 0 | 1 | 2.000 | 0 |
| 14965 | E | U | Z | U | HSCAVEOMR |   | Caveolin; VIP2I transfer vessicle ptn | 0 | 1 | 2.000 | 0 |
| 14615 | E | P | E | B | HUMCD3621 |   | Cell surface antigen CD36 | 0 | 1 | 2.000 | 0 |
| 14562 | E | P | E | B | HUMA15 |   | Cell surface glycoptn A-15, CD63 famil | 0 | 1 | 2.000 | 0 |
| 11743 | O | C | M | Q | PIGCITSYN | P | Citrate synthase | 0 | 1 | 2.000 | 0 |
| 10028 | E | S | E | K | RATCARHC | R | Clathrin, heavy chain | 0 | 1 | 2.000 | 0 |
| 14762 | E | C | K | K | HUMCOL4A |   | Collagen, type IV, alpha-1 | 0 | 1 | 2.000 | 0 |
| 13335 | E | P | S | P | HSCOLL1 |   | Collagenase | 0 | 1 | 2.000 | 0 |
| 13843 | E | P | S | P | HUMOGCA |   | Collagenase inhibitor | 0 | 1 | 2.000 | 0 |
| 12910 | H | P | U | U | HSFSCT |   | Corticotropin; 5' flanking sequence | 0 | 1 | 2.000 | 0 |
| 11832 | E | U | U | U | HUMCRPR |   | Cysteine-rich peptide | 0 | 1 | 2.000 | 0 |
| 10548 | O | U | N | D | RATCEBP | R | DNA binding protein C/EB; CCAAT bp | 0 | 1 | 2.000 | 1 |
| 12187 | E | C | M | D | HUMMTSSB |   | DNA binding protein, single strand, mt | 0 | 1 | 2.000 | 0 |
| 14597 | E | P | U | U | HUMELP1A |   | ERD-2-lik protein, ELP-1 | 0 | 1 | 2.000 | 0 |
| 13665 | I | U | U | U | HUMXT01708 |   | EST01708; 01817; 01669 (actin-like) | 0 | 1 | 2.000 | 0 |
| 14403 | E | P | S | S | HUMBCI |   | Endoexin II; lipocortin V; vasc a-coag | 0 | 1 | 2.000 | 0 |
| 11439 | E | P | C | I | HUMFABPHA |   | Fatty acid binding protein homologue | 0 | 1 | 2.000 | 1 |
| 11365 | E | P | E | B | HUMFCREA |   | Fc receptor, epsilon, gamms chain | 0 | 1 | 2.000 | 0 |
| 12867 | E | P | E | B | HSFNRA |   | Fibronectin receptor alpha subunit | 0 | 1 | 2.000 | 0 |
| 13885 | O | P | C | G | DOGRAB10 | D | GTP binding protein, brain-specific | 0 | 1 | 2.000 | 2 |
| 14198 | E | P | C | G | HUMRACB |   | GTP binding protein, ras-related | 0 | 1 | 2.000 | 0 |
| 11189 | E | P | C | G | HSGTPCYI |   | GTP cyclohydrolase I | 0 | 1 | 2.000 | 0 |
| 12742 | H | C | C | Q | HSG6PDGEN |   | Glucose-6-phosphate dehydrogenase G6PD | 0 | 1 | 2.000 | 0 |
| 13992 | E | U | U | E | HUMGLY1 |   | Glyoxalase I | 0 | 1 | 2.000 | 0 |
| 14618 | E | U | U | H | HSDNAJ |   | Heat shock protein dnaJ, homolog | 0 | 1 | 2.000 | 0 |
| 12776 | H | C | N | D | HSHISH2B |   | Histone H2B.1 | 0 | 1 | 2.000 | 0 |
| 10116 | E | P | E | B | HUMBA2A |   | Human leukocyte ag-B-assoc/transcr2 | 0 | 1 | 2.000 | 0 |
| 10034 | I | U | U | U | NCY000079 |   | INCYTE clone 000079 | 0 | 1 | 2.000 | 0 |
| 14581 | I | U | U | U | NCY000216 |   | INCYTE clone 000216 | 0 | 1 | 2.000 | 0 |
| 14834 | I | U | U | U | NCY000223 |   | INCYTE clone 000223 | 0 | 1 | 2.000 | 0 |
| 10924 | I | U | U | U | NCY000526 |   | INCYTE clone 000526 | 0 | 1 | 2.000 | 0 |
| 10678 | I | U | U | U | NCY000578 |   | INCYTE clone 000578 | 0 | 1 | 2.000 | 0 |
| 14383 | I | U | U | U | NCY001102 |   | INCYTE clone 001102 | 0 | 1 | 2.000 | 0 |
| 11215 | I | U | U | U | NCY001123 |   | INCYTE clone 001123 | 0 | 1 | 2.000 | 0 |
| 14361 | I | U | U | U | NCY001234 |   | INCYTE clone 001234 | 0 | 1 | 2.000 | 0 |
| 10004 | I | U | U | U | NCY001556 |   | INCYTE clone 001556 | 0 | 1 | 2.000 | 0 |
| 10903 | I | U | U | U | NCY001668 |   | INCYTE clone 001668 | 0 | 1 | 2.000 | 0 |
| 14219 | I | U | U | U | NCY002240 |   | INCYTE clone 002240 | 0 | 1 | 2.000 | 0 |
| 10397 | I | U | U | U | NCY002293 |   | INCYTE clone 002293 | 0 | 1 | 2.000 | 0 |
| 10370 | I | U | U | U | NCY010370 |   | INCYTE clone 010370 | 0 | 1 | 2.000 | 0 |
| 10002 | N |   |   |   | NYC010002 |   | INCYTE unique clone #010002 | 0 | 1 | 2.000 | 0 |
| 10007 | N |   |   |   | NYC010007 |   | INCYTE unique clone #010007 | 0 | 1 | 2.000 | 0 |
| 10008 | N |   |   |   | NYC010008 |   | INCYTE unique clone #010008 | 0 | 1 | 2.000 | 0 |
| 10011 | N |   |   |   | NYC010011 |   | INCYTE unique clone #010011 | 0 | 1 | 2.000 | 0 |
| 10017 | N |   |   |   | NYC010017 |   | INCYTE unique clone #010017 | 0 | 1 | 2.000 | 0 |
| 10027 | N |   |   |   | NYC010027 |   | INCYTE unique clone #010027 | 0 | 1 | 2.000 | 0 |
| 10029 | N |   |   |   | NYC010029 |   | INCYTE unique clone #010029 | 0 | 1 | 2.000 | 0 |
| 10083 | N |   |   |   | NYC010083 |   | INCYTE unique clone #010083 | 0 | 1 | 2.000 | 0 |
| 10087 | N |   |   |   | NYC010087 |   | INCYTE unique clone #010087 | 0 | 1 | 2.000 | 0 |
| 10095 | N |   |   |   | NYC010095 |   | INCYTE unique clone #010095 | 0 | 1 | 2.000 | 0 |

TABLE 4-continued

```
           01/25/94   16:32:50
       Clone numbers 1 through 15000
             Libraries: THP-1
             Subtracting: HMC,
             Designations: All
            Sorted by ABUNDANCE
        Total clones represented: 15000
          Total clones analyzed: 7375
       Total computation time: 31.35 minutes
d = designation  f = distribution  z = location  r = function  s = species  i = interest
         1057 genes, for a total of 2151 clones
```

| number | d | f | z | r | entry | s | descriptor | bgfreq | rfend | ratio | i |
|---|---|---|---|---|---|---|---|---|---|---|---|
| 10096 | N | | | | NYC010096 | | INCYTE unique clone #010096 | 0 | 1 | 2.000 | 0 |
| 10098 | N | | | | NYC010098 | | INCYTE unique clone #010098 | 0 | 1 | 2.000 | 0 |
| 10102 | N | | | | NYC010102 | | INCYTE unique clone #010102 | 0 | 1 | 2.000 | 0 |
| 10113 | N | | | | NYC010113 | | INCYTE unique clone #010113 | 0 | 1 | 2.000 | 0 |
| 10114 | N | | | | NYC010114 | | INCYTE unique clone #010114 | 0 | 1 | 2.000 | 0 |
| 10115 | N | | | | NYC010115 | | INCYTE unique clone #010115 | 0 | 1 | 2.000 | 0 |
| 10118 | N | | | | NYC010118 | | INCYTE unique clone #010118 | 0 | 1 | 2.000 | 0 |
| 10119 | N | | | | NYC010119 | | INCYTE unique clone #010119 | 0 | 1 | 2.000 | 0 |
| 10121 | N | | | | NYC010121 | | INCYTE unique clone #010121 | 0 | 1 | 2.000 | 0 |
| 10122 | N | | | | NYC010122 | | INCYTE unique clone #010122 | 0 | 1 | 2.000 | 0 |
| 10124 | N | | | | NYC010124 | | INCYTE unique clone #010124 | 0 | 1 | 2.000 | 0 |
| 10125 | N | | | | NYC010125 | | INCYTE unique clone #010125 | 0 | 1 | 2.000 | 0 |
| 10128 | N | | | | NYC010128 | | INCYTE unique clone #010128 | 0 | 1 | 2.000 | 0 |
| 10136 | N | | | | NYC010136 | | INCYTE unique clone #010136 | 0 | 1 | 2.000 | 0 |
| 10138 | N | | | | NYC010138 | | INCYTE unique clone #010138 | 0 | 1 | 2.000 | 0 |
| 10156 | N | | | | NYC010156 | | INCYTE unique clone #010156 | 0 | 1 | 2.000 | 0 |
| 10166 | N | | | | NYC010166 | | INCYTE unique clone #010166 | 0 | 1 | 2.000 | 0 |
| 10167 | N | | | | NYC010167 | | INCYTE unique clone #010167 | 0 | 1 | 2.000 | 0 |
| 10168 | N | | | | NYC010168 | | INCYTE unique clone #010168 | 0 | 1 | 2.000 | 0 |
| 10175 | N | | | | NYC010175 | | INCYTE unique clone #010175 | 0 | 1 | 2.000 | 0 |
| 10177 | N | | | | NYC010177 | | INCYTE unique clone #010177 | 0 | 1 | 2.000 | 0 |
| 10188 | N | | | | NYC010188 | | INCYTE unique clone #010188 | 0 | 1 | 2.000 | 0 |
| 10192 | N | | | | NYC010192 | | INCYTE unique clone #010192 | 0 | 1 | 2.000 | 0 |
| 10198 | N | | | | NYC010198 | | INCYTE unique clone #010198 | 0 | 1 | 2.000 | 0 |
| 10201 | N | | | | NYC010201 | | INCYTE unique clone #010201 | 0 | 1 | 2.000 | 0 |
| 10209 | N | | | | NYC010209 | | INCYTE unique clone #010209 | 0 | 1 | 2.000 | 0 |
| 10216 | N | | | | NYC010216 | | INCYTE unique clone #010216 | 0 | 1 | 2.000 | 0 |
| 10223 | N | | | | NYC010223 | | INCYTE unique clone #010223 | 0 | 1 | 2.000 | 0 |
| 10226 | N | | | | NYC010226 | | INCYTE unique clone #010226 | 0 | 1 | 2.000 | 0 |
| 10229 | N | | | | NYC010229 | | INCYTE unique clone #010229 | 0 | 1 | 2.000 | 0 |
| 10232 | N | | | | NYC010232 | | INCYTE unique clone #010232 | 0 | 1 | 2.000 | 0 |
| 10247 | N | | | | NYC010247 | | INCYTE unique clone #010247 | 0 | 1 | 2.000 | 0 |
| 10257 | N | | | | NYC010257 | | INCYTE unique clone #010257 | 0 | 1 | 2.000 | 0 |
| 10282 | N | | | | NYC010282 | | INCYTE unique clone #010282 | 0 | 1 | 2.000 | 0 |
| 10300 | N | | | | NYC010300 | | INCYTE unique clone #010300 | 0 | 1 | 2.000 | 0 |
| 10371 | N | | | | NYC010371 | | INCYTE unique clone #010371 | 0 | 1 | 2.000 | 0 |
| 10400 | N | | | | NYC010400 | | INCYTE unique clone #010400 | 0 | 1 | 2.000 | 0 |
| 10406 | N | | | | NYC010406 | | INCYTE unique clone #010406 | 0 | 1 | 2.000 | 0 |
| 10409 | N | | | | NYC010409 | | INCYTE unique clone #010409 | 0 | 1 | 2.000 | 0 |
| 10417 | N | | | | NYC010417 | | INCYTE unique clone #010417 | 0 | 1 | 2.000 | 0 |
| 10423 | N | | | | NYC010423 | | INCYTE unique clone #010423 | 0 | 1 | 2.000 | 0 |
| 10424 | N | | | | NYC010424 | | INCYTE unique clone #010424 | 0 | 1 | 2.000 | 0 |
| 10425 | N | | | | NYC010425 | | INCYTE unique clone #010425 | 0 | 1 | 2.000 | 0 |
| 10426 | N | | | | NYC010426 | | INCYTE unique clone #010426 | 0 | 1 | 2.000 | 0 |
| 10431 | N | | | | NYC010431 | | INCYTE unique clone #010431 | 0 | 1 | 2.000 | 0 |
| 10439 | N | | | | NYC010439 | | INCYTE unique clone #010439 | 0 | 1 | 2.000 | 0 |
| 10443 | N | | | | NYC010443 | | INCYTE unique clone #010443 | 0 | 1 | 2.000 | 0 |
| 10447 | N | | | | NYC010447 | | INCYTE unique clone #010447 | 0 | 1 | 2.000 | 0 |
| 10456 | N | | | | NYC010456 | | INCYTE unique clone #010456 | 0 | 1 | 2.000 | 0 |
| 10464 | N | | | | NYC010464 | | INCYTE unique clone #010464 | 0 | 1 | 2.000 | 0 |
| 10466 | N | | | | NYC010466 | | INCYTE unique clone #010466 | 0 | 1 | 2.000 | 0 |
| 10473 | N | | | | NYC010473 | | INCYTE unique clone #010473 | 0 | 1 | 2.000 | 0 |
| 10478 | N | | | | NYC010478 | | INCYTE unique clone #010478 | 0 | 1 | 2.000 | 0 |
| 10486 | N | | | | NYC010486 | | INCYTE unique clone #010486 | 0 | 1 | 2.000 | 0 |
| 10494 | N | | | | NYC010494 | | INCYTE unique clone #010494 | 0 | 1 | 2.000 | 0 |
| 10496 | N | | | | NYC010496 | | INCYTE unique clone #010496 | 0 | 1 | 2.000 | 0 |
| 10494 | N | | | | NYC010494 | | INCYTE unique clone #010494 | 0 | 1 | 2.000 | 0 |
| 10496 | N | | | | NYC010496 | | INCYTE unique clone #010496 | 0 | 1 | 2.000 | 0 |
| 10500 | N | | | | NYC010500 | | INCYTE unique clone #010500 | 0 | 1 | 2.000 | 0 |
| 10509 | N | | | | NYC010509 | | INCYTE unique clone #010509 | 0 | 1 | 2.000 | 0 |
| 10519 | N | | | | NYC010519 | | INCYTE unique clone #010519 | 0 | 1 | 2.000 | 0 |
| 10523 | N | | | | NYC010523 | | INCYTE unique clone #010523 | 0 | 1 | 2.000 | 0 |
| 10524 | N | | | | NYC010524 | | INCYTE unique clone #010524 | 0 | 1 | 2.000 | 0 |
| 10525 | N | | | | NYC010525 | | INCYTE unique clone #010525 | 0 | 1 | 2.000 | 0 |
| 10541 | N | | | | NYC010541 | | INCYTE unique clone #010541 | 0 | 1 | 2.000 | 0 |

TABLE 4-continued

```
                        01/25/94  16:32:50
                    Clone numbers 1 through 15000
                         Libraries: THP-1
                         Subtracting: HMC,
                         Designations: All
                       Sorted by ABUNDANCE
                    Total clones represented: 15000
                      Total clones analyzed: 7375
                    Total computation time: 31.35 minutes
     d = designation   f = distribution   z = location   r = function   s = species   i = interest
                      1057 genes, for a total of 2151 clones
```

| number | d | f | z | r | entry | s | descriptor | bgfreq | rfend | ratio | i |
|---|---|---|---|---|---|---|---|---|---|---|---|
| 10542 | N | | | | NYC010542 | | INCYTE unique clone #010542 | 0 | 1 | 2.000 | 0 |
| 10565 | N | | | | NYC010565 | | INCYTE unique clone #010565 | 0 | 1 | 2.000 | 0 |
| 10568 | N | | | | NYC010568 | | INCYTE unique clone #010568 | 0 | 1 | 2.000 | 0 |
| 10569 | N | | | | NYC010569 | | INCYTE unique clone #010569 | 0 | 1 | 2.000 | 0 |
| 10573 | N | | | | NYC010573 | | INCYTE unique clone #010573 | 0 | 1 | 2.000 | 0 |
| 10575 | N | | | | NYC010575 | | INCYTE unique clone #010575 | 0 | 1 | 2.000 | 0 |
| 10577 | N | | | | NYC010577 | | INCYTE unique clone #010577 | 0 | 1 | 2.000 | 0 |
| 10578 | N | | | | NYC010578 | | INCYTE unique clone #010578 | 0 | 1 | 2.000 | 0 |
| 10579 | N | | | | NYC010579 | | INCYTE unique clone #010579 | 0 | 1 | 2.000 | 0 |
| 10581 | N | | | | NYC010581 | | INCYTE unique clone #010581 | 0 | 1 | 2.000 | 0 |
| 10583 | N | | | | NYC010583 | | INCYTE unique clone #010583 | 0 | 1 | 2.000 | 0 |
| 10587 | N | | | | NYC010587 | | INCYTE unique clone #010587 | 0 | 1 | 2.000 | 0 |
| 10604 | N | | | | NYC010604 | | INCYTE unique clone #010604 | 0 | 1 | 2.000 | 0 |
| 10616 | N | | | | NYC010616 | | INCYTE unique clone #010616 | 0 | 1 | 2.000 | 0 |
| 10617 | N | | | | NYC010617 | | INCYTE unique clone #010617 | 0 | 1 | 2.000 | 0 |
| 10623 | N | | | | NYC010623 | | INCYTE unique clone #010623 | 0 | 1 | 2.000 | 0 |
| 10625 | N | | | | NYC010625 | | INCYTE unique clone #010625 | 0 | 1 | 2.000 | 0 |
| 10635 | N | | | | NYC010635 | | INCYTE unique clone #010635 | 0 | 1 | 2.000 | 0 |
| 10636 | N | | | | NYC010636 | | INCYTE unique clone #010636 | 0 | 1 | 2.000 | 0 |
| 10642 | N | | | | NYC010642 | | INCYTE unique clone #010642 | 0 | 1 | 2.000 | 0 |
| 10650 | N | | | | NYC010650 | | INCYTE unique clone #010650 | 0 | 1 | 2.000 | 0 |
| 10662 | N | | | | NYC010662 | | INCYTE unique clone #010662 | 0 | 1 | 2.000 | 0 |
| 10665 | N | | | | NYC010665 | | INCYTE unique clone #010665 | 0 | 1 | 2.000 | 0 |
| 10669 | N | | | | NYC010669 | | INCYTE unique clone #010669 | 0 | 1 | 2.000 | 0 |
| 10676 | N | | | | NYC010676 | | INCYTE unique clone #010676 | 0 | 1 | 2.000 | 0 |
| 10677 | N | | | | NYC010677 | | INCYTE unique clone #010677 | 0 | 1 | 2.000 | 0 |
| 10680 | N | | | | NYC010680 | | INCYTE unique clone #010680 | 0 | 1 | 2.000 | 0 |
| 10681 | N | | | | NYC010681 | | INCYTE unique clone #010681 | 0 | 1 | 2.000 | 0 |
| 10686 | N | | | | NYC010686 | | INCYTE unique clone #010686 | 0 | 1 | 2.000 | 0 |
| 10688 | N | | | | NYC010688 | | INCYTE unique clone #010688 | 0 | 1 | 2.000 | 0 |
| 10693 | N | | | | NYC010693 | | INCYTE unique clone #010693 | 0 | 1 | 2.000 | 0 |
| 10697 | N | | | | NYC010697 | | INCYTE unique clone #010697 | 0 | 1 | 2.000 | 0 |
| 10763 | N | | | | NYC010763 | | INCYTE unique clone #010763 | 0 | 1 | 2.000 | 0 |
| 10767 | N | | | | NYC010767 | | INCYTE unique clone #010767 | 0 | 1 | 2.000 | 0 |
| 10773 | N | | | | NYC010773 | | INCYTE unique clone #010773 | 0 | 1 | 2.000 | 0 |
| 10787 | N | | | | NYC010787 | | INCYTE unique clone #010787 | 0 | 1 | 2.000 | 0 |
| 10830 | N | | | | NYC010830 | | INCYTE unique clone #010830 | 0 | 1 | 2.000 | 0 |
| 10841 | N | | | | NYC010841 | | INCYTE unique clone #010841 | 0 | 1 | 2.000 | 0 |
| 10844 | N | | | | NYC010844 | | INCYTE unique clone #010844 | 0 | 1 | 2.000 | 0 |
| 10846 | N | | | | NYC010846 | | INCYTE unique clone #010846 | 0 | 1 | 2.000 | 0 |
| 10860 | N | | | | NYC010860 | | INCYTE unique clone #010860 | 0 | 1 | 2.000 | 0 |
| 10865 | N | | | | NYC010865 | | INCYTE unique clone #010865 | 0 | 1 | 2.000 | 0 |
| 10885 | N | | | | NYC010885 | | INCYTE unique clone #010885 | 0 | 1 | 2.000 | 0 |
| 10892 | N | | | | NYC010892 | | INCYTE unique clone #010892 | 0 | 1 | 2.000 | 0 |
| 10900 | N | | | | NYC010900 | | INCYTE unique clone #010900 | 0 | 1 | 2.000 | 0 |
| 10904 | N | | | | NYC010904 | | INCYTE unique clone #010904 | 0 | 1 | 2.000 | 0 |
| 10905 | N | | | | NYC010905 | | INCYTE unique clone #010905 | 0 | 1 | 2.000 | 0 |
| 10922 | N | | | | NYC010922 | | INCYTE unique clone #010922 | 0 | 1 | 2.000 | 0 |
| 10925 | N | | | | NYC010925 | | INCYTE unique clone #010925 | 0 | 1 | 2.000 | 0 |
| 10940 | N | | | | NYC010940 | | INCYTE unique clone #010940 | 0 | 1 | 2.000 | 0 |
| 10942 | N | | | | NYC010942 | | INCYTE unique clone #010942 | 0 | 1 | 2.000 | 0 |
| 10944 | N | | | | NYC010944 | | INCYTE unique clone #010944 | 0 | 1 | 2.000 | 0 |
| 10957 | N | | | | NYC010957 | | INCYTE unique clone #010957 | 0 | 1 | 2.000 | 0 |
| 10961 | N | | | | NYC010961 | | INCYTE unique clone #010961 | 0 | 1 | 2.000 | 0 |
| 10997 | N | | | | NYC010997 | | INCYTE unique clone #010997 | 0 | 1 | 2.000 | 0 |
| 11008 | N | | | | NYC011008 | | INCYTE unique clone #011008 | 0 | 1 | 2.000 | 0 |
| 11034 | N | | | | NYC011034 | | INCYTE unique clone #011034 | 0 | 1 | 2.000 | 0 |
| 11047 | N | | | | NYC011047 | | INCYTE unique clone #011047 | 0 | 1 | 2.000 | 0 |
| 11051 | N | | | | NYC011051 | | INCYTE unique clone #011051 | 0 | 1 | 2.000 | 0 |
| 11057 | N | | | | NYC011057 | | INCYTE unique clone #011057 | 0 | 1 | 2.000 | 0 |
| 11115 | N | | | | NYC011115 | | INCYTE unique clone #011115 | 0 | 1 | 2.000 | 0 |
| 11118 | N | | | | NYC011118 | | INCYTE unique clone #011118 | 0 | 1 | 2.000 | 0 |
| 11119 | N | | | | NYC011119 | | INCYTE unique clone #011119 | 0 | 1 | 2.000 | 0 |
| 11150 | N | | | | NYC011150 | | INCYTE unique clone #011150 | 0 | 1 | 2.000 | 0 |
| 11152 | N | | | | NYC011152 | | INCYTE unique clone #011152 | 0 | 1 | 2.000 | 0 |

TABLE 4-continued

01/25/94  16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes
d = designation  f = distribution  z = location  r = function  s = species  i = interest
1057 genes, for a total of 2151 clones

| number | d | f | z | r | entry | s | descriptor | bgfreq | rfend | ratio | i |
|---|---|---|---|---|---|---|---|---|---|---|---|
| 11177 | N | | | | NYC011177 | | INCYTE unique clone #011177 | 0 | 1 | 2.000 | 0 |
| 11197 | N | | | | NYC011197 | | INCYTE unique clone #011197 | 0 | 1 | 2.000 | 0 |
| 11204 | N | | | | NYC011204 | | INCYTE unique clone #011204 | 0 | 1 | 2.000 | 0 |
| 11213 | N | | | | NYC011213 | | INCYTE unique clone #011213 | 0 | 1 | 2.000 | 0 |
| 11214 | N | | | | NYC011214 | | INCYTE unique clone #011214 | 0 | 1 | 2.000 | 0 |
| 11220 | N | | | | NYC011220 | | INCYTE unique clone #011220 | 0 | 1 | 2.000 | 0 |
| 11230 | N | | | | NYC011230 | | INCYTE unique clone #011230 | 0 | 1 | 2.000 | 0 |
| 11237 | N | | | | NYC011237 | | INCYTE unique clone #011237 | 0 | 1 | 2.000 | 0 |
| 11250 | N | | | | NYC011250 | | INCYTE unique clone #011250 | 0 | 1 | 2.000 | 0 |
| 11263 | N | | | | NYC011263 | | INCYTE unique clone #011263 | 0 | 1 | 2.000 | 0 |
| 11264 | N | | | | NYC011264 | | INCYTE unique clone #011264 | 0 | 1 | 2.000 | 0 |
| 11268 | N | | | | NYC011268 | | INCYTE unique clone #011268 | 0 | 1 | 2.000 | 0 |
| 11270 | N | | | | NYC011270 | | INCYTE unique clone #011270 | 0 | 1 | 2.000 | 0 |
| 11275 | N | | | | NYC011275 | | INCYTE unique clone #011275 | 0 | 1 | 2.000 | 0 |
| 11293 | N | | | | NYC011293 | | INCYTE unique clone #011293 | 0 | 1 | 2.000 | 0 |
| 11318 | N | | | | NYC011318 | | INCYTE unique clone #011318 | 0 | 1 | 2.000 | 0 |
| 11322 | N | | | | NYC011322 | | INCYTE unique clone #011322 | 0 | 1 | 2.000 | 0 |
| 11324 | N | | | | NYC011324 | | INCYTE unique clone #011324 | 0 | 1 | 2.000 | 0 |
| 11352 | N | | | | NYC011352 | | INCYTE unique clone #011352 | 0 | 1 | 2.000 | 0 |
| 11332 | N | | | | NYC011332 | | INCYTE unique clone #011332 | 0 | 1 | 2.000 | 0 |
| 11333 | N | | | | NYC011333 | | INCYTE unique clone #011333 | 0 | 1 | 2.000 | 0 |
| 11338 | N | | | | NYC011338 | | INCYTE unique clone #011338 | 0 | 1 | 2.000 | 0 |
| 11339 | N | | | | NYC011339 | | INCYTE unique clone #011339 | 0 | 1 | 2.000 | 0 |
| 11340 | N | | | | NYC011340 | | INCYTE unique clone #011340 | 0 | 1 | 2.000 | 0 |
| 11348 | N | | | | NYC011348 | | INCYTE unique clone #011348 | 0 | 1 | 2.000 | 0 |
| 11378 | N | | | | NYC011378 | | INCYTE unique clone #011378 | 0 | 1 | 2.000 | 0 |
| 11391 | N | | | | NYC011391 | | INCYTE unique clone #011391 | 0 | 1 | 2.000 | 0 |
| 11392 | N | | | | NYC011392 | | INCYTE unique clone #011392 | 0 | 1 | 2.000 | 0 |
| 11398 | N | | | | NYC011398 | | INCYTE unique clone #011398 | 0 | 1 | 2.000 | 0 |
| 11408 | N | | | | NYC011408 | | INCYTE unique clone #011408 | 0 | 1 | 2.000 | 0 |
| 11413 | N | | | | NYC011413 | | INCYTE unique clone #011413 | 0 | 1 | 2.000 | 0 |
| 11425 | N | | | | NYC011425 | | INCYTE unique clone #011425 | 0 | 1 | 2.000 | 0 |
| 11435 | N | | | | NYC011435 | | INCYTE unique clone #011435 | 0 | 1 | 2.000 | 0 |
| 11441 | N | | | | NYC011441 | | INCYTE unique clone #011441 | 0 | 1 | 2.000 | 0 |
| 11442 | N | | | | NYC011442 | | INCYTE unique clone #011442 | 0 | 1 | 2.000 | 0 |
| 11484 | N | | | | NYC011484 | | INCYTE unique clone #011484 | 0 | 1 | 2.000 | 0 |
| 11503 | N | | | | NYC011503 | | INCYTE unique clone #011503 | 0 | 1 | 2.000 | 0 |
| 11521 | N | | | | NYC011521 | | INCYTE unique clone #011521 | 0 | 1 | 2.000 | 0 |
| 11522 | N | | | | NYC011522 | | INCYTE unique clone #011522 | 0 | 1 | 2.000 | 0 |
| 11525 | N | | | | NYC011525 | | INCYTE unique clone #011525 | 0 | 1 | 2.000 | 0 |
| 11528 | N | | | | NYC011528 | | INCYTE unique clone #011528 | 0 | 1 | 2.000 | 0 |
| 11532 | N | | | | NYC011532 | | INCYTE unique clone #011532 | 0 | 1 | 2.000 | 0 |
| 11565 | N | | | | NYC011565 | | INCYTE unique clone #011565 | 0 | 1 | 2.000 | 0 |
| 11570 | N | | | | NYC011570 | | INCYTE unique clone #011570 | 0 | 1 | 2.000 | 0 |
| 11581 | N | | | | NYC011581 | | INCYTE unique clone #011581 | 0 | 1 | 2.000 | 0 |
| 11594 | N | | | | NYC011594 | | INCYTE unique clone #011594 | 0 | 1 | 2.000 | 0 |
| 11596 | N | | | | NYC011596 | | INCYTE unique clone #011596 | 0 | 1 | 2.000 | 0 |
| 11597 | N | | | | NYC011597 | | INCYTE unique clone #011597 | 0 | 1 | 2.000 | 0 |
| 11599 | N | | | | NYC011599 | | INCYTE unique clone #011599 | 0 | 1 | 2.000 | 0 |
| 11600 | N | | | | NYC011600 | | INCYTE unique clone #011600 | 0 | 1 | 2.000 | 0 |
| 11602 | N | | | | NYC011602 | | INCYTE unique clone #011602 | 0 | 1 | 2.000 | 0 |
| 11603 | N | | | | NYC011603 | | INCYTE unique clone #011603 | 0 | 1 | 2.000 | 0 |
| 11609 | N | | | | NYC011609 | | INCYTE unique clone #011609 | 0 | 1 | 2.000 | 0 |
| 11624 | N | | | | NYC011624 | | INCYTE unique clone #011624 | 0 | 1 | 2.000 | 0 |
| 11689 | N | | | | NYC011689 | | INCYTE unique clone #011689 | 0 | 1 | 2.000 | 0 |
| 11692 | N | | | | NYC011692 | | INCYTE unique clone #011692 | 0 | 1 | 2.000 | 0 |
| 11707 | N | | | | NYC011707 | | INCYTE unique clone #011707 | 0 | 1 | 2.000 | 0 |
| 11709 | N | | | | NYC011709 | | INCYTE unique clone #011709 | 0 | 1 | 2.000 | 0 |
| 11712 | N | | | | NYC011712 | | INCYTE unique clone #011712 | 0 | 1 | 2.000 | 0 |
| 11725 | N | | | | NYC011725 | | INCYTE unique clone #011725 | 0 | 1 | 2.000 | 0 |
| 11729 | N | | | | NYC011729 | | INCYTE unique clone #011729 | 0 | 1 | 2.000 | 0 |
| 11734 | N | | | | NYC011734 | | INCYTE unique clone #011734 | 0 | 1 | 2.000 | 0 |
| 11763 | N | | | | NYC011763 | | INCYTE unique clone #011763 | 0 | 1 | 2.000 | 0 |
| 11774 | N | | | | NYC011774 | | INCYTE unique clone #011774 | 0 | 1 | 2.000 | 0 |
| 11807 | N | | | | NYC011807 | | INCYTE unique clone #011807 | 0 | 1 | 2.000 | 0 |

TABLE 4-continued

```
                       01/25/94   16:32:50
                  Clone numbers 1 through 15000
                        Libraries: THP-1
                       Subtracting: HMC,
                       Designations: All
                      Sorted by ABUNDANCE
                  Total clones represented: 15000
                     Total clones analyzed: 7375
                  Total computation time: 31.35 minutes
    d = designation  f = distribution  z = location  r = function  s = species  i = interest
                  1057 genes, for a total of 2151 clones
```

| number | d | f | z | r | entry | s | descriptor | bgfreq | rfend | ratio | i |
|---|---|---|---|---|---|---|---|---|---|---|---|
| 11808 | N | | | | NYC011808 | | INCYTE unique clone #011808 | 0 | 1 | 2.000 | 0 |
| 11809 | N | | | | NYC011809 | | INCYTE unique clone #011809 | 0 | 1 | 2.000 | 0 |
| 11812 | N | | | | NYC011812 | | INCYTE unique clone #011812 | 0 | 1 | 2.000 | 0 |
| 11814 | N | | | | NYC011814 | | INCYTE unique clone #011814 | 0 | 1 | 2.000 | 0 |
| 11820 | N | | | | NYC011820 | | INCYTE unique clone #011820 | 0 | 1 | 2.000 | 0 |
| 11822 | N | | | | NYC011822 | | INCYTE unique clone #011822 | 0 | 1 | 2.000 | 0 |
| 11833 | N | | | | NYC011833 | | INCYTE unique clone #011833 | 0 | 1 | 2.000 | 0 |
| 11835 | N | | | | NYC011835 | | INCYTE unique clone #011835 | 0 | 1 | 2.000 | 0 |
| 11839 | N | | | | NYC011839 | | INCYTE unique clone #011839 | 0 | 1 | 2.000 | 0 |
| 11841 | N | | | | NYC011841 | | INCYTE unique clone #011841 | 0 | 1 | 2.000 | 0 |
| 11844 | N | | | | NYC011844 | | INCYTE unique clone #011844 | 0 | 1 | 2.000 | 0 |
| 11846 | N | | | | NYC011846 | | INCYTE unique clone #011846 | 0 | 1 | 2.000 | 0 |
| 11849 | N | | | | NYC011849 | | INCYTE unique clone #011849 | 0 | 1 | 2.000 | 0 |
| 11851 | N | | | | NYC011851 | | INCYTE unique clone #011851 | 0 | 1 | 2.000 | 0 |
| 11854 | N | | | | NYC011854 | | INCYTE unique clone #011854 | 0 | 1 | 2.000 | 0 |
| 11856 | N | | | | NYC011856 | | INCYTE unique clone #011856 | 0 | 1 | 2.000 | 0 |
| 11857 | N | | | | NYC011857 | | INCYTE unique clone #011857 | 0 | 1 | 2.000 | 0 |
| 11864 | N | | | | NYC011864 | | INCYTE unique clone #011864 | 0 | 1 | 2.000 | 0 |
| 11865 | N | | | | NYC011865 | | INCYTE unique clone #011865 | 0 | 1 | 2.000 | 0 |
| 11870 | N | | | | NYC011870 | | INCYTE unique clone #011870 | 0 | 1 | 2.000 | 0 |
| 11872 | N | | | | NYC011872 | | INCYTE unique clone #011872 | 0 | 1 | 2.000 | 0 |
| 11876 | N | | | | NYC011876 | | INCYTE unique clone #011876 | 0 | 1 | 2.000 | 0 |
| 11878 | N | | | | NYC011878 | | INCYTE unique clone #011878 | 0 | 1 | 2.000 | 0 |
| 11885 | N | | | | NYC011885 | | INCYTE unique clone #011885 | 0 | 1 | 2.000 | 0 |
| 11886 | N | | | | NYC011886 | | INCYTE unique clone #011886 | 0 | 1 | 2.000 | 0 |
| 11887 | N | | | | NYC011887 | | INCYTE unique clone #011887 | 0 | 1 | 2.000 | 0 |
| 11889 | N | | | | NYC011889 | | INCYTE unique clone #011889 | 0 | 1 | 2.000 | 0 |
| 11890 | N | | | | NYC011890 | | INCYTE unique clone #011890 | 0 | 1 | 2.000 | 0 |
| 11891 | N | | | | NYC011891 | | INCYTE unique clone #011891 | 0 | 1 | 2.000 | 0 |
| 11896 | N | | | | NYC011896 | | INCYTE unique clone #011896 | 0 | 1 | 2.000 | 0 |
| 11900 | N | | | | NYC011900 | | INCYTE unique clone #011900 | 0 | 1 | 2.000 | 0 |
| 11903 | N | | | | NYC011903 | | INCYTE unique clone #011903 | 0 | 1 | 2.000 | 0 |
| 11913 | N | | | | NYC011913 | | INCYTE unique clone #011913 | 0 | 1 | 2.000 | 0 |
| 11956 | N | | | | NYC011956 | | INCYTE unique clone #011956 | 0 | 1 | 2.000 | 0 |
| 11958 | N | | | | NYC011958 | | INCYTE unique clone #011958 | 0 | 1 | 2.000 | 0 |
| 11978 | N | | | | NYC011978 | | INCYTE unique clone #011978 | 0 | 1 | 2.000 | 0 |
| 12019 | N | | | | NYC012019 | | INCYTE unique clone #012019 | 0 | 1 | 2.000 | 0 |
| 12032 | N | | | | NYC012032 | | INCYTE unique clone #012032 | 0 | 1 | 2.000 | 0 |
| 12033 | N | | | | NYC012033 | | INCYTE unique clone #012033 | 0 | 1 | 2.000 | 0 |
| 12063 | N | | | | NYC012063 | | INCYTE unique clone #012063 | 0 | 1 | 2.000 | 0 |
| 12065 | N | | | | NYC012065 | | INCYTE unique clone #012065 | 0 | 1 | 2.000 | 0 |
| 12067 | N | | | | NYC012067 | | INCYTE unique clone #012067 | 0 | 1 | 2.000 | 0 |
| 12073 | N | | | | NYC012073 | | INCYTE unique clone #012073 | 0 | 1 | 2.000 | 0 |
| 12076 | N | | | | NYC012076 | | INCYTE unique clone #012076 | 0 | 1 | 2.000 | 0 |
| 12080 | N | | | | NYC012080 | | INCYTE unique clone #012080 | 0 | 1 | 2.000 | 0 |
| 12084 | N | | | | NYC012084 | | INCYTE unique clone #012084 | 0 | 1 | 2.000 | 0 |
| 12186 | N | | | | NYC012186 | | INCYTE unique clone #012186 | 0 | 1 | 2.000 | 0 |
| 12212 | N | | | | NYC012212 | | INCYTE unique clone #012212 | 0 | 1 | 2.000 | 0 |
| 12231 | N | | | | NYC012231 | | INCYTE unique clone #012231 | 0 | 1 | 2.000 | 0 |
| 12247 | N | | | | NYC012247 | | INCYTE unique clone #012247 | 0 | 1 | 2.000 | 0 |
| 12249 | N | | | | NYC012249 | | INCYTE unique clone #012249 | 0 | 1 | 2.000 | 0 |
| 12291 | N | | | | NYC012291 | | INCYTE unique clone #012291 | 0 | 1 | 2.000 | 0 |
| 12335 | N | | | | NYC012335 | | INCYTE unique clone #012335 | 0 | 1 | 2.000 | 0 |
| 12336 | N | | | | NYC012336 | | INCYTE unique clone #012336 | 0 | 1 | 2.000 | 0 |
| 12353 | N | | | | NYC012353 | | INCYTE unique clone #012353 | 0 | 1 | 2.000 | 0 |
| 12356 | N | | | | NYC012356 | | INCYTE unique clone #012356 | 0 | 1 | 2.000 | 0 |
| 12364 | N | | | | NYC012364 | | INCYTE unique clone #012364 | 0 | 1 | 2.000 | 0 |
| 12386 | N | | | | NYC012386 | | INCYTE unique clone #012386 | 0 | 1 | 2.000 | 0 |
| 12410 | N | | | | NYC012410 | | INCYTE unique clone #012410 | 0 | 1 | 2.000 | 0 |
| 12411 | N | | | | NYC012411 | | INCYTE unique clone #012411 | 0 | 1 | 2.000 | 0 |
| 12423 | N | | | | NYC012423 | | INCYTE unique clone #012423 | 0 | 1 | 2.000 | 0 |
| 12426 | N | | | | NYC012426 | | INCYTE unique clone #012426 | 0 | 1 | 2.000 | 0 |
| 12437 | N | | | | NYC012437 | | INCYTE unique clone #012437 | 0 | 1 | 2.000 | 0 |
| 12440 | N | | | | NYC012440 | | INCYTE unique clone #012440 | 0 | 1 | 2.000 | 0 |
| 12477 | N | | | | NYC012477 | | INCYTE unique clone #012477 | 0 | 1 | 2.000 | 0 |

TABLE 4-continued

```
                    01/25/94  16:32:50
              Clone numbers 1 through 15000
                     Libraries: THP-1
                     Subtracting: HMC,
                     Designations: All
                    Sorted by ABUNDANCE
              Total clones represented: 15000
                  Total clones analyzed: 7375
              Total computation time: 31.35 minutes
  d = designation  f = distribution  z = location  r = function  s = species  i = interest
              1057 genes, for a total of 2151 clones
```

| number | d | f | z | r | entry | s | descriptor | bgfreq | rfend | ratio | i |
|---|---|---|---|---|---|---|---|---|---|---|---|
| 12496 | N | | | | NYC012496 | | INCYTE unique clone #012496 | 0 | 1 | 2.000 | 0 |
| 12498 | N | | | | NYC012498 | | INCYTE unique clone #012498 | 0 | 1 | 2.000 | 0 |
| 12502 | N | | | | NYC012502 | | INCYTE unique clone #012502 | 0 | 1 | 2.000 | 0 |
| 12503 | N | | | | NYC012503 | | INCYTE unique clone #012503 | 0 | 1 | 2.000 | 0 |
| 12517 | N | | | | NYC012517 | | INCYTE unique clone #012517 | 0 | 1 | 2.000 | 0 |
| 12519 | N | | | | NYC012519 | | INCYTE unique clone #012519 | 0 | 1 | 2.000 | 0 |
| 12530 | N | | | | NYC012530 | | INCYTE unique clone #012530 | 0 | 1 | 2.000 | 0 |
| 12541 | N | | | | NYC012541 | | INCYTE unique clone #012541 | 0 | 1 | 2.000 | 0 |
| 12547 | N | | | | NYC012547 | | INCYTE unique clone #012547 | 0 | 1 | 2.000 | 0 |
| 12566 | N | | | | NYC012566 | | INCYTE unique clone #012566 | 0 | 1 | 2.000 | 0 |
| 12568 | N | | | | NYC012568 | | INCYTE unique clone #012568 | 0 | 1 | 2.000 | 0 |
| 12569 | N | | | | NYC012569 | | INCYTE unique clone #012569 | 0 | 1 | 2.000 | 0 |
| 12583 | N | | | | NYC012583 | | INCYTE unique clone #012583 | 0 | 1 | 2.000 | 0 |
| 12621 | N | | | | NYC012621 | | INCYTE unique clone #012621 | 0 | 1 | 2.000 | 0 |
| 12636 | N | | | | NYC012636 | | INCYTE unique clone #012636 | 0 | 1 | 2.000 | 0 |
| 12638 | N | | | | NYC012638 | | INCYTE unique clone #012638 | 0 | 1 | 2.000 | 0 |
| 12643 | N | | | | NYC012643 | | INCYTE unique clone #012643 | 0 | 1 | 2.000 | 0 |
| 12662 | N | | | | NYC012662 | | INCYTE unique clone #012662 | 0 | 1 | 2.000 | 0 |
| 12669 | N | | | | NYC012669 | | INCYTE unique clone #012669 | 0 | 1 | 2.000 | 0 |
| 12679 | N | | | | NYC012679 | | INCYTE unique clone #012679 | 0 | 1 | 2.000 | 0 |
| 12702 | N | | | | NYC012702 | | INCYTE unique clone #012702 | 0 | 1 | 2.000 | 0 |
| 12705 | N | | | | NYC012705 | | INCYTE unique clone #012705 | 0 | 1 | 2.000 | 0 |
| 12748 | N | | | | NYC012748 | | INCYTE unique clone #012748 | 0 | 1 | 2.000 | 0 |
| 12757 | N | | | | NYC012757 | | INCYTE unique clone #012757 | 0 | 1 | 2.000 | 0 |
| 12786 | N | | | | NYC012786 | | INCYTE unique clone #012786 | 0 | 1 | 2.000 | 0 |
| 12808 | N | | | | NYC012808 | | INCYTE unique clone #012808 | 0 | 1 | 2.000 | 0 |
| 12810 | N | | | | NYC012810 | | INCYTE unique clone #012810 | 0 | 1 | 2.000 | 0 |
| 12828 | N | | | | NYC012828 | | INCYTE unique clone #012828 | 0 | 1 | 2.000 | 0 |
| 12830 | N | | | | NYC012830 | | INCYTE unique clone #012830 | 0 | 1 | 2.000 | 0 |
| 12843 | N | | | | NYC012843 | | INCYTE unique clone #012843 | 0 | 1 | 2.000 | 0 |
| 12844 | N | | | | NYC012844 | | INCYTE unique clone #012844 | 0 | 1 | 2.000 | 0 |
| 12845 | N | | | | NYC012845 | | INCYTE unique clone #012845 | 0 | 1 | 2.000 | 0 |
| 12851 | N | | | | NYC012851 | | INCYTE unique clone #012851 | 0 | 1 | 2.000 | 0 |
| 12852 | N | | | | NYC012852 | | INCYTE unique clone #012852 | 0 | 1 | 2.000 | 0 |
| 12854 | N | | | | NYC012854 | | INCYTE unique clone #012854 | 0 | 1 | 2.000 | 0 |
| 12855 | N | | | | NYC012855 | | INCYTE unique clone #012855 | 0 | 1 | 2.000 | 0 |
| 12860 | N | | | | NYC012860 | | INCYTE unique clone #012860 | 0 | 1 | 2.000 | 0 |
| 12866 | N | | | | NYC012866 | | INCYTE unique clone #012866 | 0 | 1 | 2.000 | 0 |
| 12868 | N | | | | NYC012868 | | INCYTE unique clone #012868 | 0 | 1 | 2.000 | 0 |
| 12870 | N | | | | NYC012870 | | INCYTE unique clone #012870 | 0 | 1 | 2.000 | 0 |
| 12880 | N | | | | NYC012880 | | INCYTE unique clone #012880 | 0 | 1 | 2.000 | 0 |
| 12884 | N | | | | NYC012884 | | INCYTE unique clone #012884 | 0 | 1 | 2.000 | 0 |
| 12885 | N | | | | NYC012885 | | INCYTE unique clone #012885 | 0 | 1 | 2.000 | 0 |
| 12892 | N | | | | NYC012892 | | INCYTE unique clone #012892 | 0 | 1 | 2.000 | 0 |
| 12898 | N | | | | NYC012898 | | INCYTE unique clone #012898 | 0 | 1 | 2.000 | 0 |
| 12904 | N | | | | NYC012904 | | INCYTE unique clone #012904 | 0 | 1 | 2.000 | 0 |
| 12950 | N | | | | NYC012950 | | INCYTE unique clone #012950 | 0 | 1 | 2.000 | 0 |
| 12958 | N | | | | NYC012958 | | INCYTE unique clone #012958 | 0 | 1 | 2.000 | 0 |
| 13011 | N | | | | NYC013011 | | INCYTE unique clone #013011 | 0 | 1 | 2.000 | 0 |
| 13020 | N | | | | NYC013020 | | INCYTE unique clone #013020 | 0 | 1 | 2.000 | 0 |
| 13023 | N | | | | NYC013023 | | INCYTE unique clone #013023 | 0 | 1 | 2.000 | 0 |
| 13025 | N | | | | NYC013025 | | INCYTE unique clone #013025 | 0 | 1 | 2.000 | 0 |
| 13026 | N | | | | NYC013026 | | INCYTE unique clone #013026 | 0 | 1 | 2.000 | 0 |
| 13028 | N | | | | NYC013028 | | INCYTE unique clone #013028 | 0 | 1 | 2.000 | 0 |
| 13031 | N | | | | NYC013031 | | INCYTE unique clone #013031 | 0 | 1 | 2.000 | 0 |
| 13032 | N | | | | NYC013032 | | INCYTE unique clone #013032 | 0 | 1 | 2.000 | 0 |
| 13058 | N | | | | NYC013058 | | INCYTE unique clone #013058 | 0 | 1 | 2.000 | 0 |
| 13061 | N | | | | NYC013061 | | INCYTE unique clone #013061 | 0 | 1 | 2.000 | 0 |
| 13064 | N | | | | NYC013064 | | INCYTE unique clone #013064 | 0 | 1 | 2.000 | 0 |
| 13068 | N | | | | NYC013068 | | INCYTE unique clone #013068 | 0 | 1 | 2.000 | 0 |
| 13071 | N | | | | NYC013071 | | INCYTE unique clone #013071 | 0 | 1 | 2.000 | 0 |
| 13073 | N | | | | NYC013073 | | INCYTE unique clone #013073 | 0 | 1 | 2.000 | 0 |
| 13077 | N | | | | NYC013077 | | INCYTE unique clone #013077 | 0 | 1 | 2.000 | 0 |
| 13079 | N | | | | NYC013079 | | INCYTE unique clone #013079 | 0 | 1 | 2.000 | 0 |
| 13082 | N | | | | NYC013082 | | INCYTE unique clone #013082 | 0 | 1 | 2.000 | 0 |

TABLE 4-continued

```
                      01/25/94   16:32:50
                  Clone numbers 1 through 15000
                       Libraries: THP-1
                       Subtracting: HMC,
                       Designations: All
                      Sorted by ABUNDANCE
                  Total clones represented: 15000
                     Total clones analyzed: 7375
                  Total computation time: 31.35 minutes
     d = designation   f = distribution   z = location   r = function   s = species   i = interest
                   1057 genes, for a total of 2151 clones
```

| number | d | f | z | r | entry | s | descriptor | bgfreq | rfend | ratio | i |
|---|---|---|---|---|---|---|---|---|---|---|---|
| 13083 | N | | | | NYC013083 | | INCYTE unique clone #013083 | 0 | 1 | 2.000 | 0 |
| 13105 | N | | | | NYC013105 | | INCYTE unique clone #013105 | 0 | 1 | 2.000 | 0 |
| 13106 | N | | | | NYC013106 | | INCYTE unique clone #013106 | 0 | 1 | 2.000 | 0 |
| 13108 | N | | | | NYC013108 | | INCYTE unique clone #013108 | 0 | 1 | 2.000 | 0 |
| 13109 | N | | | | NYC013109 | | INCYTE unique clone #013109 | 0 | 1 | 2.000 | 0 |
| 13143 | N | | | | NYC013143 | | INCYTE unique clone #013143 | 0 | 1 | 2.000 | 0 |
| 13152 | N | | | | NYC013152 | | INCYTE unique clone #013152 | 0 | 1 | 2.000 | 0 |
| 13157 | N | | | | NYC013157 | | INCYTE unique clone #013157 | 0 | 1 | 2.000 | 0 |
| 13158 | N | | | | NYC013158 | | INCYTE unique clone #013158 | 0 | 1 | 2.000 | 0 |
| 13161 | N | | | | NYC013161 | | INCYTE unique clone #013161 | 0 | 1 | 2.000 | 0 |
| 13164 | N | | | | NYC013164 | | INCYTE unique clone #013164 | 0 | 1 | 2.000 | 0 |
| 13167 | N | | | | NYC013167 | | INCYTE unique clone #013167 | 0 | 1 | 2.000 | 0 |
| 13175 | N | | | | NYC013175 | | INCYTE unique clone #013175 | 0 | 1 | 2.000 | 0 |
| 13179 | N | | | | NYC013179 | | INCYTE unique clone #013179 | 0 | 1 | 2.000 | 0 |
| 13189 | N | | | | NYC013189 | | INCYTE unique clone #013189 | 0 | 1 | 2.000 | 0 |
| 13218 | N | | | | NYC013218 | | INCYTE unique clone #013218 | 0 | 1 | 2.000 | 0 |
| 13223 | N | | | | NYC013223 | | INCYTE unique clone #013223 | 0 | 1 | 2.000 | 0 |
| 13234 | N | | | | NYC013234 | | INCYTE unique clone #013234 | 0 | 1 | 2.000 | 0 |
| 12243 | N | | | | NYC012243 | | INCYTE unique clone #012243 | 0 | 1 | 2.000 | 0 |
| 13253 | N | | | | NYC013253 | | INCYTE unique clone #013253 | 0 | 1 | 2.000 | 0 |
| 13255 | N | | | | NYC013255 | | INCYTE unique clone #013255 | 0 | 1 | 2.000 | 0 |
| 13256 | N | | | | NYC013256 | | INCYTE unique clone #013256 | 0 | 1 | 2.000 | 0 |
| 13262 | N | | | | NYC013262 | | INCYTE unique clone #013262 | 0 | 1 | 2.000 | 0 |
| 13274 | N | | | | NYC013274 | | INCYTE unique clone #013274 | 0 | 1 | 2.000 | 0 |
| 13279 | N | | | | NYC013279 | | INCYTE unique clone #013279 | 0 | 1 | 2.000 | 0 |
| 13286 | N | | | | NYC013286 | | INCYTE unique clone #013286 | 0 | 1 | 2.000 | 0 |
| 13292 | N | | | | NYC013292 | | INCYTE unique clone #013292 | 0 | 1 | 2.000 | 0 |
| 13293 | N | | | | NYC013293 | | INCYTE unique clone #013293 | 0 | 1 | 2.000 | 0 |
| 13323 | N | | | | NYC013323 | | INCYTE unique clone #013323 | 0 | 1 | 2.000 | 0 |
| 13332 | N | | | | NYC013332 | | INCYTE unique clone #013332 | 0 | 1 | 2.000 | 0 |
| 13333 | N | | | | NYC013333 | | INCYTE unique clone #013333 | 0 | 1 | 2.000 | 0 |
| 13337 | N | | | | NYC013337 | | INCYTE unique clone #013337 | 0 | 1 | 2.000 | 0 |
| 13356 | N | | | | NYC013356 | | INCYTE unique clone #013356 | 0 | 1 | 2.000 | 0 |
| 13361 | N | | | | NYC013361 | | INCYTE unique clone #013361 | 0 | 1 | 2.000 | 0 |
| 13421 | N | | | | NYC013421 | | INCYTE unique clone #013421 | 0 | 1 | 2.000 | 0 |
| 13433 | N | | | | NYC013433 | | INCYTE unique clone #013433 | 0 | 1 | 2.000 | 0 |
| 13443 | N | | | | NYC013443 | | INCYTE unique clone #013443 | 0 | 1 | 2.000 | 0 |
| 13454 | N | | | | NYC013454 | | INCYTE unique clone #013454 | 0 | 1 | 2.000 | 0 |
| 13478 | N | | | | NYC013478 | | INCYTE unique clone #013478 | 0 | 1 | 2.000 | 0 |
| 13485 | N | | | | NYC013485 | | INCYTE unique clone #013485 | 0 | 1 | 2.000 | 0 |
| 13490 | N | | | | NYC013490 | | INCYTE unique clone #013490 | 0 | 1 | 2.000 | 0 |
| 13494 | N | | | | NYC013494 | | INCYTE unique clone #013494 | 0 | 1 | 2.000 | 0 |
| 13508 | N | | | | NYC013508 | | INCYTE unique clone #013508 | 0 | 1 | 2.000 | 0 |
| 13522 | N | | | | NYC013522 | | INCYTE unique clone #013522 | 0 | 1 | 2.000 | 0 |
| 13535 | N | | | | NYC013535 | | INCYTE unique clone #013535 | 0 | 1 | 2.000 | 0 |
| 13543 | N | | | | NYC013543 | | INCYTE unique clone #013543 | 0 | 1 | 2.000 | 0 |
| 13553 | N | | | | NYC013553 | | INCYTE unique clone #013553 | 0 | 1 | 2.000 | 0 |
| 13563 | N | | | | NYC013563 | | INCYTE unique clone #013563 | 0 | 1 | 2.000 | 0 |
| 13565 | N | | | | NYC013565 | | INCYTE unique clone #013565 | 0 | 1 | 2.000 | 0 |
| 13585 | N | | | | NYC013585 | | INCYTE unique clone #013585 | 0 | 1 | 2.000 | 0 |
| 13666 | N | | | | NYC013666 | | INCYTE unique clone #013666 | 0 | 1 | 2.000 | 0 |
| 13691 | N | | | | NYC013691 | | INCYTE unique clone #013691 | 0 | 1 | 2.000 | 0 |
| 13714 | N | | | | NYC013714 | | INCYTE unique clone #013714 | 0 | 1 | 2.000 | 0 |
| 13716 | N | | | | NYC013716 | | INCYTE unique clone #013716 | 0 | 1 | 2.000 | 0 |
| 13719 | N | | | | NYC013719 | | INCYTE unique clone #013719 | 0 | 1 | 2.000 | 0 |
| 13726 | N | | | | NYC013726 | | INCYTE unique clone #013726 | 0 | 1 | 2.000 | 0 |
| 13727 | N | | | | NYC013727 | | INCYTE unique clone #013727 | 0 | 1 | 2.000 | 0 |
| 13728 | N | P | S | S | NYC013728 | | INCYTE unique clone #013728 | 0 | 1 | 2.000 | 0 |
| 13729 | N | U | U | U | NYC013729 | | INCYTE unique clone #013729 | 0 | 1 | 2.000 | 0 |
| 13735 | N | P | S | S | NYC013735 | | INCYTE unique clone #013735 | 0 | 1 | 2.000 | 0 |
| 13751 | N | | | | NYC013751 | | INCYTE unique clone #013751 | 0 | 1 | 2.000 | 0 |
| 13764 | N | | | | NYC013764 | | INCYTE unique clone #013764 | 0 | 1 | 2.000 | 0 |
| 13770 | N | | | | NYC013770 | | INCYTE unique clone #013770 | 0 | 1 | 2.000 | 0 |
| 13811 | N | | | | NYC013811 | | INCYTE unique clone #013811 | 0 | 1 | 2.000 | 0 |
| 13815 | N | | | | NYC013815 | | INCYTE unique clone #013815 | 0 | 1 | 2.000 | 0 |

TABLE 4-continued

01/25/94  16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes
d = designation   f = distribution   z = location   r = function   s = species   i = interest
1057 genes, for a total of 2151 clones

| number | d | f | z | r | entry | s | descriptor | bgfreq | rfend | ratio | i |
|---|---|---|---|---|---|---|---|---|---|---|---|
| 13833 | N | | | | NYC013833 | | INCYTE unique clone #013833 | 0 | 1 | 2.000 | 0 |
| 13840 | N | | | | NYC013840 | | INCYTE unique clone #013840 | 0 | 1 | 2.000 | 0 |
| 13877 | N | | | | NYC013877 | | INCYTE unique clone #013877 | 0 | 1 | 2.000 | 0 |
| 13884 | N | | | | NYC013884 | | INCYTE unique clone #013884 | 0 | 1 | 2.000 | 0 |
| 13889 | N | | | | NYC013889 | | INCYTE unique clone #013889 | 0 | 1 | 2.000 | 0 |
| 13896 | N | | | | NYC013896 | | INCYTE unique clone #013896 | 0 | 1 | 2.000 | 0 |
| 13930 | N | | | | NYC013930 | | INCYTE unique clone #013930 | 0 | 1 | 2.000 | 0 |
| 13936 | N | | | | NYC013936 | | INCYTE unique clone #013936 | 0 | 1 | 2.000 | 0 |
| 13939 | N | | | | NYC013939 | | INCYTE unique clone #013939 | 0 | 1 | 2.000 | 0 |
| 13954 | N | | | | NYC013954 | | INCYTE unique clone #013954 | 0 | 1 | 2.000 | 0 |
| 13959 | N | | | | NYC013959 | | INCYTE unique clone #013959 | 0 | 1 | 2.000 | 0 |
| 13985 | N | | | | NYC013985 | | INCYTE unique clone #013985 | 0 | 1 | 2.000 | 0 |
| 13991 | N | | | | NYC013991 | | INCYTE unique clone #013991 | 0 | 1 | 2.000 | 0 |
| 13994 | N | | | | NYC013994 | | INCYTE unique clone #013994 | 0 | 1 | 2.000 | 0 |
| 14000 | N | | | | NYC014000 | | INCYTE unique clone #014000 | 0 | 1 | 2.000 | 0 |
| 14006 | N | | | | NYC014006 | | INCYTE unique clone #014006 | 0 | 1 | 2.000 | 0 |
| 14016 | N | | | | NYC014016 | | INCYTE unique clone #014016 | 0 | 1 | 2.000 | 0 |
| 14019 | N | | | | NYC014019 | | INCYTE unique clone #014019 | 0 | 1 | 2.000 | 0 |
| 14021 | N | | | | NYC014021 | | INCYTE unique clone #014021 | 0 | 1 | 2.000 | 0 |
| 14023 | N | | | | NYC014023 | | INCYTE unique clone #014023 | 0 | 1 | 2.000 | 0 |
| 14024 | N | | | | NYC014024 | | INCYTE unique clone #014024 | 0 | 1 | 2.000 | 0 |
| 14025 | N | | | | NYC014025 | | INCYTE unique clone #014025 | 0 | 1 | 2.000 | 0 |
| 14026 | N | | | | NYC014026 | | INCYTE unique clone #014026 | 0 | 1 | 2.000 | 0 |
| 14030 | N | | | | NYC014030 | | INCYTE unique clone #014030 | 0 | 1 | 2.000 | 0 |
| 14031 | N | | | | NYC014031 | | INCYTE unique clone #014031 | 0 | 1 | 2.000 | 0 |
| 14034 | N | | | | NYC014034 | | INCYTE unique clone #014034 | 0 | 1 | 2.000 | 0 |
| 14041 | N | | | | NYC014041 | | INCYTE unique clone #014041 | 0 | 1 | 2.000 | 0 |
| 14043 | N | | | | NYC014043 | | INCYTE unique clone #014043 | 0 | 1 | 2.000 | 0 |
| 14044 | N | | | | NYC014044 | | INCYTE unique clone #014044 | 0 | 1 | 2.000 | 0 |
| 14046 | N | | | | NYC014046 | | INCYTE unique clone #014046 | 0 | 1 | 2.000 | 0 |
| 14049 | N | | | | NYC014049 | | INCYTE unique clone #014049 | 0 | 1 | 2.000 | 0 |
| 14050 | N | | | | NYC014050 | | INCYTE unique clone #014050 | 0 | 1 | 2.000 | 0 |
| 14054 | N | | | | NYC014054 | | INCYTE unique clone #014054 | 0 | 1 | 2.000 | 0 |
| 14061 | N | | | | NYC014061 | | INCYTE unique clone #014061 | 0 | 1 | 2.000 | 0 |
| 14063 | N | | | | NYC014063 | | INCYTE unique clone #014063 | 0 | 1 | 2.000 | 0 |
| 14065 | N | | | | NYC014065 | | INCYTE unique clone #014065 | 0 | 1 | 2.000 | 0 |
| 14071 | N | | | | NYC014071 | | INCYTE unique clone #014071 | 0 | 1 | 2.000 | 0 |
| 14073 | N | | | | NYC014073 | | INCYTE unique clone #014073 | 0 | 1 | 2.000 | 0 |
| 14075 | N | | | | NYC014075 | | INCYTE unique clone #014075 | 0 | 1 | 2.000 | 0 |
| 14087 | N | | | | NYC014087 | | INCYTE unique clone #014087 | 0 | 1 | 2.000 | 0 |
| 14088 | N | | | | NYC014088 | | INCYTE unique clone #014088 | 0 | 1 | 2.000 | 0 |
| 14089 | N | | | | NYC014089 | | INCYTE unique clone #014089 | 0 | 1 | 2.000 | 0 |
| 14092 | N | | | | NYC014092 | | INCYTE unique clone #014092 | 0 | 1 | 2.000 | 0 |
| 14094 | N | | | | NYC014094 | | INCYTE unique clone #014094 | 0 | 1 | 2.000 | 0 |
| 14095 | N | | | | NYC014095 | | INCYTE unique clone #014095 | 0 | 1 | 2.000 | 0 |
| 14098 | N | | | | NYC014098 | | INCYTE unique clone #014098 | 0 | 1 | 2.000 | 0 |
| 14099 | N | | | | NYC014099 | | INCYTE unique clone #014099 | 0 | 1 | 2.000 | 0 |
| 14100 | N | | | | NYC014100 | | INCYTE unique clone #014100 | 0 | 1 | 2.000 | 0 |
| 14102 | N | | | | NYC014102 | | INCYTE unique clone #014102 | 0 | 1 | 2.000 | 0 |
| 14106 | N | | | | NYC014106 | | INCYTE unique clone #014106 | 0 | 1 | 2.000 | 0 |
| 14111 | N | | | | NYC014111 | | INCYTE unique clone #014111 | 0 | 1 | 2.000 | 0 |
| 14112 | N | | | | NYC014112 | | INCYTE unique clone #014112 | 0 | 1 | 2.000 | 0 |
| 14115 | N | | | | NYC014115 | | INCYTE unique clone #014115 | 0 | 1 | 2.000 | 0 |
| 14118 | N | | | | NYC014118 | | INCYTE unique clone #014118 | 0 | 1 | 2.000 | 0 |
| 14119 | N | | | | NYC014119 | | INCYTE unique clone #014119 | 0 | 1 | 2.000 | 0 |
| 14121 | N | | | | NYC014121 | | INCYTE unique clone #014121 | 0 | 1 | 2.000 | 0 |
| 14122 | N | | | | NYC014122 | | INCYTE unique clone #014122 | 0 | 1 | 2.000 | 0 |
| 14123 | N | | | | NYC014123 | | INCYTE unique clone #014123 | 0 | 1 | 2.000 | 0 |
| 14135 | N | | | | NYC014135 | | INCYTE unique clone #014135 | 0 | 1 | 2.000 | 0 |
| 14137 | N | | | | NYC014137 | | INCYTE unique clone #014137 | 0 | 1 | 2.000 | 0 |
| 14142 | N | | | | NYC014142 | | INCYTE unique clone #014142 | 0 | 1 | 2.000 | 0 |
| 14144 | N | | | | NYC014144 | | INCYTE unique clone #014144 | 0 | 1 | 2.000 | 0 |
| 14147 | N | | | | NYC014147 | | INCYTE unique clone #014147 | 0 | 1 | 2.000 | 0 |
| 14151 | N | | | | NYC014151 | | INCYTE unique clone #014151 | 0 | 1 | 2.000 | 0 |
| 14172 | N | | | | NYC014172 | | INCYTE unique clone #014172 | 0 | 1 | 2.000 | 0 |

TABLE 4-continued

```
                    01/25/94  16:32:50
              Clone numbers 1 through 15000
                     Libraries: THP-1
                     Subtracting: HMC,
                     Designations: All
                   Sorted by ABUNDANCE
             Total clones represented: 15000
                 Total clones analyzed: 7375
              Total computation time: 31.35 minutes
  d = designation  f = distribution  z = location  r = function  s = species  i = interest
              1057 genes, for a total of 2151 clones
```

| number | d | f | z | r | entry | s | descriptor | bgfreq | rfend | ratio | i |
|---|---|---|---|---|---|---|---|---|---|---|---|
| 14178 | N | | | | NYC014178 | | INCYTE unique clone #014178 | 0 | 1 | 2.000 | 0 |
| 14181 | N | | | | NYC014181 | | INCYTE unique clone #014181 | 0 | 1 | 2.000 | 0 |
| 14186 | N | | | | NYC014186 | | INCYTE unique clone #014186 | 0 | 1 | 2.000 | 0 |
| 14194 | N | | | | NYC014194 | | INCYTE unique clone #014194 | 0 | 1 | 2.000 | 0 |
| 14197 | N | | | | NYC014197 | | INCYTE unique clone #014197 | 0 | 1 | 2.000 | 0 |
| 14203 | N | | | | NYC014203 | | INCYTE unique clone #014203 | 0 | 1 | 2.000 | 0 |
| 14204 | N | | | | NYC014204 | | INCYTE unique clone #014204 | 0 | 1 | 2.000 | 0 |
| 14211 | N | | | | NYC014211 | | INCYTE unique clone #014211 | 0 | 1 | 2.000 | 0 |
| 14217 | N | | | | NYC014217 | | INCYTE unique clone #014217 | 0 | 1 | 2.000 | 0 |
| 14221 | N | | | | NYC014221 | | INCYTE unique clone #014221 | 0 | 1 | 2.000 | 0 |
| 14222 | N | | | | NYC014222 | | INCYTE unique clone #014222 | 0 | 1 | 2.000 | 0 |
| 14226 | N | | | | NYC014226 | | INCYTE unique clone #014226 | 0 | 1 | 2.000 | 0 |
| 14227 | N | | | | NYC014227 | | INCYTE unique clone #014227 | 0 | 1 | 2.000 | 0 |
| 14229 | N | | | | NYC014229 | | INCYTE unique clone #014229 | 0 | 1 | 2.000 | 0 |
| 14236 | N | | | | NYC014236 | | INCYTE unique clone #014236 | 0 | 1 | 2.000 | 0 |
| 14241 | N | | | | NYC014241 | | INCYTE unique clone #014241 | 0 | 1 | 2.000 | 0 |
| 14288 | N | | | | NYC014288 | | INCYTE unique clone #014288 | 0 | 1 | 2.000 | 0 |
| 14293 | N | | | | NYC014293 | | INCYTE unique clone #014293 | 0 | 1 | 2.000 | 0 |
| 14303 | N | | | | NYC014303 | | INCYTE unique clone #014303 | 0 | 1 | 2.000 | 0 |
| 14307 | N | | | | NYC014307 | | INCYTE unique clone #014307 | 0 | 1 | 2.000 | 0 |
| 14310 | N | | | | NYC014310 | | INCYTE unique clone #014310 | 0 | 1 | 2.000 | 0 |
| 14319 | N | | | | NYC014319 | | INCYTE unique clone #014319 | 0 | 1 | 2.000 | 0 |
| 14324 | N | | | | NYC014324 | | INCYTE unique clone #014324 | 0 | 1 | 2.000 | 0 |
| 14339 | N | | | | NYC014339 | | INCYTE unique clone #014339 | 0 | 1 | 2.000 | 0 |
| 14342 | N | | | | NYC014342 | | INCYTE unique clone #014342 | 0 | 1 | 2.000 | 0 |
| 14345 | N | | | | NYC014345 | | INCYTE unique clone #014345 | 0 | 1 | 2.000 | 0 |
| 14346 | N | | | | NYC014346 | | INCYTE unique clone #014346 | 0 | 1 | 2.000 | 0 |
| 14348 | N | | | | NYC014348 | | INCYTE unique clone #014348 | 0 | 1 | 2.000 | 0 |
| 14355 | N | | | | NYC014355 | | INCYTE unique clone #014355 | 0 | 1 | 2.000 | 0 |
| 14358 | N | | | | NYC014358 | | INCYTE unique clone #014358 | 0 | 1 | 2.000 | 0 |
| 14360 | N | | | | NYC014360 | | INCYTE unique clone #014360 | 0 | 1 | 2.000 | 0 |
| 14367 | N | | | | NYC014367 | | INCYTE unique clone #014367 | 0 | 1 | 2.000 | 0 |
| 14370 | N | | | | NYC014370 | | INCYTE unique clone #014370 | 0 | 1 | 2.000 | 0 |
| 14378 | N | | | | NYC014378 | | INCYTE unique clone #014378 | 0 | 1 | 2.000 | 0 |
| 14387 | N | | | | NYC014387 | | INCYTE unique clone #014387 | 0 | 1 | 2.000 | 0 |
| 14388 | N | | | | NYC014388 | | INCYTE unique clone #014388 | 0 | 1 | 2.000 | 0 |
| 14392 | N | | | | NYC014392 | | INCYTE unique clone #014392 | 0 | 1 | 2.000 | 0 |
| 14398 | N | | | | NYC014398 | | INCYTE unique clone #014398 | 0 | 1 | 2.000 | 0 |
| 14401 | N | | | | NYC014401 | | INCYTE unique clone #014401 | 0 | 1 | 2.000 | 0 |
| 14405 | N | | | | NYC014405 | | INCYTE unique clone #014405 | 0 | 1 | 2.000 | 0 |
| 14604 | N | | | | NYC014604 | | INCYTE unique clone #014604 | 0 | 1 | 2.000 | 0 |
| 14607 | N | | | | NYC014607 | | INCYTE unique clone #014607 | 0 | 1 | 2.000 | 0 |
| 14612 | N | | | | NYC014612 | | INCYTE unique clone #014612 | 0 | 1 | 2.000 | 0 |
| 14620 | N | | | | NYC014620 | | INCYTE unique clone #014620 | 0 | 1 | 2.000 | 0 |
| 14625 | N | | | | NYC014625 | | INCYTE unique clone #014625 | 0 | 1 | 2.000 | 0 |
| 14630 | N | | | | NYC014630 | | INCYTE unique clone #014630 | 0 | 1 | 2.000 | 0 |
| 14636 | N | | | | NYC014636 | | INCYTE unique clone #014636 | 0 | 1 | 2.000 | 0 |
| 14639 | N | | | | NYC014639 | | INCYTE unique clone #014639 | 0 | 1 | 2.000 | 0 |
| 14642 | N | | | | NYC014642 | | INCYTE unique clone #014642 | 0 | 1 | 2.000 | 0 |
| 14645 | N | | | | NYC014645 | | INCYTE unique clone #014645 | 0 | 1 | 2.000 | 0 |
| 14654 | N | | | | NYC014654 | | INCYTE unique clone #014654 | 0 | 1 | 2.000 | 0 |
| 14657 | N | | | | NYC014657 | | INCYTE unique clone #014657 | 0 | 1 | 2.000 | 0 |
| 14661 | N | | | | NYC014661 | | INCYTE unique clone #014661 | 0 | 1 | 2.000 | 0 |
| 14667 | N | | | | NYC014667 | | INCYTE unique clone #014667 | 0 | 1 | 2.000 | 0 |
| 14669 | N | | | | NYC014669 | | INCYTE unique clone #014669 | 0 | 1 | 2.000 | 0 |
| 14671 | N | | | | NYC014671 | | INCYTE unique clone #014671 | 0 | 1 | 2.000 | 0 |
| 14673 | N | | | | NYC014673 | | INCYTE unique clone #014673 | 0 | 1 | 2.000 | 0 |
| 14674 | N | | | | NYC014674 | | INCYTE unique clone #014674 | 0 | 1 | 2.000 | 0 |
| 14677 | N | | | | NYC014677 | | INCYTE unique clone #014677 | 0 | 1 | 2.000 | 0 |
| 14683 | N | | | | NYC014683 | | INCYTE unique clone #014683 | 0 | 1 | 2.000 | 0 |
| 14698 | N | | | | NYC014698 | | INCYTE unique clone #014698 | 0 | 1 | 2.000 | 0 |
| 14703 | N | | | | NYC014703 | | INCYTE unique clone #014703 | 0 | 1 | 2.000 | 0 |
| 14710 | N | | | | NYC014710 | | INCYTE unique clone #014710 | 0 | 1 | 2.000 | 0 |
| 14744 | N | | | | NYC014744 | | INCYTE unique clone #014744 | 0 | 1 | 2.000 | 0 |
| 14746 | N | | | | NYC014746 | | INCYTE unique clone #014746 | 0 | 1 | 2.000 | 0 |

TABLE 4-continued

```
                01/25/94    16:32:50
            Clone numbers 1 through 15000
                  Libraries: THP-1
                  Subtracting: HMC,
                  Designations: All
                 Sorted by ABUNDANCE
             Total clones represented: 15000
              Total clones analyzed: 7375
            Total computation time: 31.35 minutes
   d = designation  f = distribution  z = location  r = function  s = species  i = interest
              1057 genes, for a total of 2151 clones
```

| number | d | f | z | r | entry | s | descriptor | bgfreq | rfend | ratio | i |
|---|---|---|---|---|---|---|---|---|---|---|---|
| 14756 | N | | | | NYC014756 | | INCYTE unique clone #014756 | 0 | 1 | 2.000 | 0 |
| 14758 | N | | | | NYC014758 | | INCYTE unique clone #014758 | 0 | 1 | 2.000 | 0 |
| 14760 | N | | | | NYC014760 | | INCYTE unique clone #014760 | 0 | 1 | 2.000 | 0 |
| 14761 | N | | | | NYC014761 | | INCYTE unique clone #014761 | 0 | 1 | 2.000 | 0 |
| 14764 | N | | | | NYC014764 | | INCYTE unique clone #014764 | 0 | 1 | 2.000 | 0 |
| 14766 | N | | | | NYC014766 | | INCYTE unique clone #014766 | 0 | 1 | 2.000 | 0 |
| 14771 | N | | | | NYC014771 | | INCYTE unique clone #014771 | 0 | 1 | 2.000 | 0 |
| 14775 | N | | | | NYC014775 | | INCYTE unique clone #014775 | 0 | 1 | 2.000 | 0 |
| 14780 | N | | | | NYC014780 | | INCYTE unique clone #014780 | 0 | 1 | 2.000 | 0 |
| 14782 | N | | | | NYC014782 | | INCYTE unique clone #014782 | 0 | 1 | 2.000 | 0 |
| 14785 | N | | | | NYC014785 | | INCYTE unique clone #014785 | 0 | 1 | 2.000 | 0 |
| 14786 | N | | | | NYC014786 | | INCYTE unique clone #014786 | 0 | 1 | 2.000 | 0 |
| 14794 | N | | | | NYC014794 | | INCYTE unique clone #014794 | 0 | 1 | 2.000 | 0 |
| 14798 | N | | | | NYC014798 | | INCYTE unique clone #014798 | 0 | 1 | 2.000 | 0 |
| 14799 | N | | | | NYC014799 | | INCYTE unique clone #014799 | 0 | 1 | 2.000 | 0 |
| 14830 | N | | | | NYC014830 | | INCYTE unique clone #014830 | 0 | 1 | 2.000 | 0 |
| 14831 | N | | | | NYC014831 | | INCYTE unique clone #014831 | 0 | 1 | 2.000 | 0 |
| 14835 | N | | | | NYC014835 | | INCYTE unique clone #014835 | 0 | 1 | 2.000 | 0 |
| 14839 | N | | | | NYC014839 | | INCYTE unique clone #014839 | 0 | 1 | 2.000 | 0 |
| 14840 | N | | | | NYC014840 | | INCYTE unique clone #014840 | 0 | 1 | 2.000 | 0 |
| 14843 | N | | | | NYC014843 | | INCYTE unique clone #014843 | 0 | 1 | 2.000 | 0 |
| 14845 | N | | | | NYC014845 | | INCYTE unique clone #014845 | 0 | 1 | 2.000 | 0 |
| 14847 | N | | | | NYC014847 | | INCYTE unique clone #014847 | 0 | 1 | 2.000 | 0 |
| 14852 | N | | | | NYC014852 | | INCYTE unique clone #014852 | 0 | 1 | 2.000 | 0 |
| 14855 | N | | | | NYC014855 | | INCYTE unique clone #014855 | 0 | 1 | 2.000 | 0 |
| 14887 | N | | | | NYC014887 | | INCYTE unique clone #014887 | 0 | 1 | 2.000 | 0 |
| 14892 | N | | | | NYC014892 | | INCYTE unique clone #014892 | 0 | 1 | 2.000 | 0 |
| 14896 | N | | | | NYC014896 | | INCYTE unique clone #014896 | 0 | 1 | 2.000 | 0 |
| 14898 | N | | | | NYC014898 | | INCYTE unique clone #014898 | 0 | 1 | 2.000 | 0 |
| 14903 | N | | | | NYC014903 | | INCYTE unique clone #014903 | 0 | 1 | 2.000 | 0 |
| 14909 | N | | | | NYC014909 | | INCYTE unique clone #014909 | 0 | 1 | 2.000 | 0 |
| 14910 | N | | | | NYC014910 | | INCYTE unique clone #014910 | 0 | 1 | 2.000 | 0 |
| 14912 | N | | | | NYC014912 | | INCYTE unique clone #014912 | 0 | 1 | 2.000 | 0 |
| 14914 | N | | | | NYC014914 | | INCYTE unique clone #014914 | 0 | 1 | 2.000 | 0 |
| 14915 | N | | | | NYC014915 | | INCYTE unique clone #014915 | 0 | 1 | 2.000 | 0 |
| 14917 | N | | | | NYC014917 | | INCYTE unique clone #014917 | 0 | 1 | 2.000 | 0 |
| 14918 | N | | | | NYC014918 | | INCYTE unique clone #014918 | 0 | 1 | 2.000 | 0 |
| 14922 | N | | | | NYC014922 | | INCYTE unique clone #014922 | 0 | 1 | 2.000 | 0 |
| 14930 | N | | | | NYC014930 | | INCYTE unique clone #014930 | 0 | 1 | 2.000 | 0 |
| 14931 | N | | | | NYC014931 | | INCYTE unique clone #014931 | 0 | 1 | 2.000 | 0 |
| 14932 | N | | | | NYC014932 | | INCYTE unique clone #014932 | 0 | 1 | 2.000 | 0 |
| 14935 | N | | | | NYC014935 | | INCYTE unique clone #014935 | 0 | 1 | 2.000 | 0 |
| 14939 | N | | | | NYC014939 | | INCYTE unique clone #014939 | 0 | 1 | 2.000 | 0 |
| 14943 | N | | | | NYC014943 | | INCYTE unique clone #014943 | 0 | 1 | 2.000 | 0 |
| 14944 | N | | | | NYC014944 | | INCYTE unique clone #014944 | 0 | 1 | 2.000 | 0 |
| 14961 | N | | | | NYC014961 | | INCYTE unique clone #014961 | 0 | 1 | 2.000 | 0 |
| 14974 | N | | | | NYC014974 | | INCYTE unique clone #014974 | 0 | 1 | 2.000 | 0 |
| 14976 | N | | | | NYC014976 | | INCYTE unique clone #014976 | 0 | 1 | 2.000 | 0 |
| 14979 | N | | | | NYC014979 | | INCYTE unique clone #014979 | 0 | 1 | 2.000 | 0 |
| 14981 | N | | | | NYC014981 | | INCYTE unique clone #014981 | 0 | 1 | 2.000 | 0 |
| 14990 | N | | | | NYC014990 | | INCYTE unique clone #014990 | 0 | 1 | 2.000 | 0 |
| 14991 | N | | | | NYC014991 | | INCYTE unique clone #014991 | 0 | 1 | 2.000 | 0 |
| 14926 | E | C | C | N | HUMIMPH | | Inosine mono-PO4 dehydrogenase, type 1 | 0 | 1 | 2.000 | 0 |
| 10061 | O | P | C | E | DOGSMIT | D | Inositol cotransporter, Na/Myo- | 0 | 1 | 2.000 | 0 |
| 11895 | E | P | U | B | HUMGFIBPA | | Insulin-like growth factor-binding ptn | 0 | 1 | 2.000 | 0 |
| 13354 | E | P | E | B | HSICAM1 | | Intercellular adhesion molecule ICAM-1 | 0 | 1 | 2.000 | 0 |
| 10097 | E | P | U | H | HUMIFNINI | | Interferon gamma inducible early resp | 0 | 1 | 2.000 | 0 |
| 11012 | E | P | S | S | HUMIL10 | | Interleukin-10 (includes intron) | 0 | 1 | 2.000 | 0 |
| 12403 | E | P | S | S | HUMIL6CSF | | Interleukin-6 | 0 | 1 | 2.000 | 0 |
| 10521 | E | U | E | B | HSKDEL | | KDEL receptor, ERD 2 | 0 | 1 | 2.000 | 0 |
| 12805 | E | P | C | K | HUMP13KIN | | Kinase P13; tyrosin kinase receptor | 0 | 1 | 2.000 | 0 |
| 10553 | O | U | C | Y | RATERK3 | R | Kinase, extracellular signal-relaed | 0 | 1 | 2.000 | 1 |
| 14670 | E | U | N | D | HUMHPF4 | | Kruppel related DNA binding protein 4 | 0 | 1 | 2.000 | 0 |
| 13873 | E | P | E | B | HUMCD53 | | Leukocyte surfaceantigen CD53 | 0 | 1 | 2.000 | 0 |
| 14108 | E | P | S | W | HUMLIPCHL | | Lipase, lysosomal, cid; cholesterase | 0 | 1 | 2.000 | 0 |

TABLE 4-continued

01/25/94  16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes
d = designation   f = distribution   z = location   r = function   s = species   i = interest
1057 genes, for a total of 2151 clones

| number | d | f | z | r | entry | s | descriptor | bgfreq | rfend | ratio | i |
|---|---|---|---|---|---|---|---|---|---|---|---|
| 11733 | E | P | C | I | HUMALBP |   | Lipid binding protein, adipocyte | 0 | 1 | 2.000 | 0 |
| 14083 | E | C | S | W | HUMLPL |   | Lipoprotein lipase | 0 | 1 | 2.000 | 0 |
| 12109 | E | C | C | E | HUMGLYI |   | Lyase, lactoyl glutathione | 0 | 1 | 2.000 | 0 |
| 11042 | E | P | E | B | HUMLAMP1B |   | Lysosomal membrane gp-2; LAMP-2 | 0 | 1 | 2.000 | 0 |
| 11827 | E | P | E | B | HSHLDR1B |   | MHC class II antigen; glycoprotein | 0 | 1 | 2.000 | 0 |
| 11246 | E | P | E | B | HUMA2MGRAP |   | Macroglobulin, (alpha-2)-associated pt | 0 | 1 | 2.000 | 0 |
| 12869 | E | P | E | B | HUMA2M |   | Macroglobulin, alpha-2- | 0 | 1 | 2.000 | 0 |
| 10511 | E | C | C | T | S57575 |   | Macropain, HMW proteosome SU zeta | 0 | 1 | 2.000 | 0 |
| 13339 | E | C | N | K | HUMMNMP |   | Major nuclear matrix protein | 0 | 1 | 2.000 | 0 |
| 14665 | E | P | S | A | HSMGSA |   | Melanoma growth stim factor (MIP-2a) | 0 | 1 | 2.000 | 0 |
| 12707 | E | C | C | E | HSNMTDC |   | Methylene THF dehydrogenase, NAD-dep | 0 | 1 | 2.000 | 0 |
| 12963 | O | U | E | W | CRUMEVTRSP | S | Mevalonte transporter | 0 | 1 | 2.000 | 3 |
| 14321 | E | C | E | B | HUMMCR |   | Mineralocorticoid receptor | 0 | 1 | 2.000 | 0 |
| 12838 | E | P | C | Y | HUMMKK |   | Mitogen activated ptn kinasekinase MAP | 0 | 1 | 2.000 | 0 |
| 13705 | O | C | M | Z | BTUBRE49 | V | NADH:ubiquinone oxidoreductase | 0 | 1 | 2.000 | 0 |
| 11030 | O | P | U | H | RATIRPRA | R | NGF-induced IFN-related ptn | 0 | 1 | 2.000 | 4 |
| 14036 | O | P | S | H | RATNIPS | R | NGF-inducible secreted protein | 0 | 1 | 2.000 | 1 |
| 11304 | O | P | U | U | M28274 | R | Neuronal protein NP25 | 0 | 1 | 2.000 | 1 |
| 14224 | E | C | N | U | HUMNUMB23 |   | Nuclear protein B23 | 0 | 1 | 2.000 | 0 |
| 13904 | E | C | N | U | HUMNAP |   | Nucleosome assembly protein | 0 | 1 | 2.000 | 0 |
| 14568 | E | C | U | U | HUMTB31A |   | Omnipotent suppressor 45, yeast; TB3-1 | 0 | 1 | 2.000 | 0 |
| 13542 | E | U | U | Y | HSCFMS |   | Oncogene fms | 0 | 1 | 2.000 | 0 |
| 10796 | E | P | U | D | HSRLF |   | Oncogene myc; rlf gene | 0 | 1 | 2.000 | 0 |
| 10032 | E | P | U | P | HMRAB5B |   | Oncogene rab5b, ras-related ptn | 0 | 1 | 2.000 | 0 |
| 12672 | E | C | U | O | HSRAPB1 |   | Oncogene rap 18; ras-related | 0 | 1 | 2.000 | 0 |
| 14707 | E | U | U | G | HSRAP1A |   | Oncogene rap1a; ras related protein | 0 | 1 | 2.000 | 0 |
| 14368 | E | U | U | D | HUMCRELA |   | Oncogene rel | 0 | 1 | 2.000 | 0 |
| 13353 | O | C | N | D | MMCRELM |   | Oncogene rel | 0 | 1 | 2.000 | 1 |
| 13829 | E | C | C | W | HUM2OGDH |   | Oxoglutarate dehydrogenase, 2- | 0 | 1 | 2.000 | 0 |
| 14309 | H | P | N | D | HSRDC1MR |   | POU homeodomain ptn, nerve-specific | 0 | 1 | 2.000 | 1 |
| 11512 | E | P | C | M | HUMPAM12 |   | Peptidylglycine a-amidating monoosy | 0 | 1 | 2.000 | 0 |
| 14549 | O | C | N | D | BTPAPOLY | V | Poly (A) polymerase | 0 | 1 | 2.000 | 0 |
| 12812 | O | C | C | T | M27072 | F | Poly-A binding protein | 0 | 1 | 2.000 | 1 |
| 13069 | E | C | C | T | HUMTIA1E |   | Poly-A binding protein homolog TIA-1 | 0 | 1 | 2.000 | 1 |
| 11314 | E | P | C | T | HSPROS27 |   | Prosomal RNA-binding ptn PROS-27 | 0 | 1 | 2.000 | 0 |
| 14640 | E | U | U | Y | HUMG19P1A |   | Protein 80-H, kinase c substrate | 0 | 1 | 2.000 | 0 |
| 11254 | E | P | U | U | HUMB12A |   | Protein B12; TNF-ind endothelial 1 res | 0 | 1 | 2.000 | 0 |
| 11445 | E | C | C | Y | HUMCAMPPK |   | Protein kinase, cAMP-dependent, type 1a | 0 | 1 | 2.000 | 0 |
| 10845 | O | U | U | U | MUSBRAF | M | Protein of unknown function | 0 | 1 | 2.000 | 0 |
| 13875 | O | C | C | Y | OCPP1 | B | Protein phosphatase 1 | 0 | 1 | 2.000 | 1 |
| 12494 | H | P | E | B | HSPMIPR |   | Putative receptor protein PMI | 0 | 1 | 2.000 | 3 |
| 13317 | E | C | C | N | HUMDUPTPP |   | Pyrophosphatase DUTP | 0 | 1 | 2.000 | 0 |
| 10949 | E | C | N | T | HSRING10 |   | RING10; proteasome-related MHC gene | 0 | 1 | 2.000 | 0 |
| 11728 | E | C | N | E | HUMPOLACB |   | Replicative polymerase accessory ptn | 0 | 1 | 2.000 | 0 |
| 13319 | E | P | N | O | HUMRETBLAS |   | Retinoblastoma susceptibility gene | 0 | 1 | 2.000 | 0 |
| 10271 | E | P | U | O | HUMRBS |   | Retinoblastoma-associated ptn | 0 | 1 | 2.000 | 0 |
| 12764 | E | P | U | V | HSINER11 |   | Retroposon SINE-R11 (endog retrovirus) | 0 | 1 | 2.000 | 0 |
| 13226 | E | P | U | V | HUMJNLTRB |   | Retroviral long terminal repeat | 0 | 1 | 2.000 | 0 |
| 10606 | E | C | C | G | HUMRHOGDI |   | Rho GTP dissociation inhibitor | 0 | 1 | 2.000 | 1 |
| 14886 | E | C | C | N | HSRIREM1 |   | Ribonucleotide reductase M1 subunit | 0 | 1 | 2.000 | 0 |
| 14564 | E | C | C | R | HSRRN18S |   | Ribosomal RNA, 18S | 0 | 1 | 2.000 | 0 |
| 14938 | E | C | C | R | HSRPS18 |   | Ribosomal protein S18 | 0 | 1 | 2.000 | 0 |
| 12955 | O | P | U | U | CHKGISM22A | C | SM22-alpha; gizzard smooth muscle | 0 | 1 | 2.000 | 1 |
| 11909 | O | C | C | T | DOGSRP9A | D | Signal recognition particle SRP9 | 0 | 1 | 2.000 | 0 |
| 14763 | O | C | C | T | CFSRP68 | D | Signal recognition particle, 68 kDa su | 0 | 1 | 2.000 | 0 |
| 10152 | E | P | E | B | HUMZP3 |   | Sperm receptor | 0 | 1 | 2.000 | 0 |
| 13888 | H | P | E | B | HUMARC1 |   | Steroid receptor, novel/transcr factor | 0 | 1 | 2.000 | 3 |
| 10256 | E | P | S | P | HUMPACE4A |   | Subtilisin-like ptn PACE4 | 0 | 1 | 2.000 | 0 |
| 13680 | E | P | S | E | HSMNSODR |   | Superoxide dismutase, Mn | 0 | 1 | 2.000 | 0 |
| 11706 | O | C | E | U | MUSSURF4A | M | Surfeit locus 4 protein | 0 | 1 | 2.000 | 1 |
| 12520 | O | P | U | U | MMTIS7M | M | TPA-induced sequence-7 | 0 | 1 | 2.000 | 1 |
| 11374 | E | C | C | T | HSGRS |   | TRNA synthetase, glutaminyl- | 0 | 1 | 2.000 | 0 |
| 10777 | O | C | C | M | CRUSTSTA | I | TRNA synthetase, seryl- | 0 | 1 | 2.000 | 0 |
| 12675 | E | C | N | D | HSBTF3A |   | Transcription factor | 0 | 1 | 2.000 | 0 |
| 10432 | E | P | E | B | HUMTFRRA |   | Transferrin receptor | 0 | 1 | 2.000 | 0 |

TABLE 4-continued

01/25/94  16:32:50
Clone numbers 1 through 15000
Libraries: THP-1
Subtracting: HMC,
Designations: All
Sorted by ABUNDANCE
Total clones represented: 15000
Total clones analyzed: 7375
Total computation time: 31.35 minutes
d = designation  f = distribution  z = location  r = function  s = species  i = interest
1057 genes, for a total of 2151 clones

| number | d | f | z | r | entry | s | descriptor | bgfreq | rfend | ratio | i |
|---|---|---|---|---|---|---|---|---|---|---|---|
| 11154 | E | P | S | S | HSTGFB1 | | Transforming growth factor-B1 | 0 | 1 | 2.000 | 0 |
| 10026 | E | C | C | T | HUMELF2 | | Translation initiation factor 2B | 0 | 1 | 2.000 | 0 |
| 12696 | E | P | C | Y | HSCL100 | | Tyrosine phosphatase CL 100 | 0 | 1 | 2.000 | 0 |
| 13423 | E | C | C | L | HSQAE1 | | Ubiquitin activating enzyme E1 | 0 | 1 | 2.000 | 0 |
| 10858 | E | U | U | U | HUMDHAD | | Unknown transcript from cosmid DHAD | 0 | 1 | 2.000 | 0 |
| 14425 | E | C | C | N | HSNGMRNA | | Utracil DNA glycosylase | 0 | 1 | 2.000 | 0 |
| 14213 | O | U | U | U | XELXLAN | F | Xlan4 | 0 | 1 | 2.000 | 0 |
| 13456 | E | P | N | D | SSMBPROT2 | | Zn finger protein, binds MHC enhancer | 0 | 1 | 2.000 | 0 |
| 10009 | E | C | K | K | HSAC07 | | Actin, beta- | 18 | 29 | 1.611 | 0 |
| 11341 | E | P | C | I | HUMFKBP | | FK506 binding protein | 2 | 3 | 1.500 | 0 |
| 11255 | O | U | C | E | MAP5PROMR | S | Isomerase/Pi-PLc, protein disulphide- | 2 | 3 | 1.500 | 3 |
| 10019 | E | C | N | K | HUMNPM | | Nucleophosmin | 2 | 3 | 1.500 | 0 |
| 10458 | E | C | C | R | HUMRPL7A | | Ribosomal protein L7A; PLA-X; surf3 | 2 | 3 | 1.500 | 0 |
| 10901 | O | C | C | R | RNRPS5 | R | Ribosomal protein S5; EST 000HE10 | 2 | 3 | 1.500 | 0 |
| 12431 | E | P | U | U | HUMSET | | SET gene (unknown function) | 2 | 3 | 1.500 | 0 |
| 11357 | E | P | E | A | HSTRA1 | | Tumor rejection Ag; tra1 (mouse homol) | 2 | 3 | 1.500 | 0 |
| 11021 | E | C | C | Q | HSGAPDR | | Glyceraldehyde-3-phosphate dehydrogen | 3 | 4 | 1.333 | 0 |
| 10172 | E | C | C | T | HSEF1AC | | Elongation factor 1-alpha | 32 | 38 | 1.188 | 0 |
| 10024 | E | C | K | K | HSACTCGR | | Actin, cytoskeletal gamma | 7 | 7 | 1.000 | 0 |
| 10842 | O | C | M | Q | PIGMDH | P | Malate dehydrogenase | 2 | 2 | 1.000 | 0 |
| 10250 | E | P | U | U | HUMMOESIN | | Moesin (Talin/ezrin family) | 2 | 2 | 1.000 | 0 |
| 10161 | E | C | K | K | HSMRLCM | | Myosin regulatory L chain | 2 | 2 | 1.000 | 0 |
| 12798 | E | C | C | E | HUMARF2A | | ADP-ribosyltion factor 2 (ARF2) | 1 | 1 | 1.000 | 0 |
| 14022 | E | C | C | N | HUMAMPD3 | | AMP deaminase AMPD3 | 1 | 1 | 1.000 | 0 |
| 14409 | O | C | K | K | CHKCAPZ | C | Actin-capping protein, alpha2 | 1 | 1 | 1.000 | 1 |
| 10517 | E | U | U | U | HSLLREP3 | | LLrep3; repetitive DNA | 2 | 1 | 0.500 | 0 |
| 12322 | E | C | N | D | HSPTBMR | | Polypyrimidine tract-binding ptn | 2 | 1 | 0.500 | 0 |
| 13693 | E | C | C | D | HSTF2B | | Transcription initiation factor 2B | 2 | 1 | 0.500 | 0 |
| 10091 | E | C | C | R | HUMPPARP0 | | Ribosomal phosphoprotein P0, acidic | 16 | 6 | 0.375 | 0 |
| 10266 | E | C | N | D | HSH2AZ | | Histone H2A.z | 3 | 1 | 0.333 | 0 |
| 10100 | E | C | C | R | HSRPL19 | | Ribosomal protein L19 | 3 | 1 | 0.333 | 0 |
| 10099 | E | C | C | R | HUMRPS14 | | Ribosomal protein S14 | 3 | 1 | 0.333 | 0 |
| 10564 | O | C | K | K | MMALINR | M | Talin | 3 | 1 | 0.333 | 0 |

TABLE 5

* Master menu for SUBTRACTION output
SET TALK OFF
SET SAFETY OFF
SET EXACT ON
SET TYPEAHEAD TO 0
CLEAR ALL
CLEAR
SET DEVICE TO SCREEN
USE "SmartGuy:FoxBASE+/Mac:fox files:Clones.dbf"
GO TOP
STORE NUMBER TO INITIATE
GO BOTTOM
STORE NUMBER TO TERMINATE
STORE 0 TO UON
STORE 0 TO MON
STORE 0 TO TON
STORE 0 TO HON
STORE 0 TO AON
STORE 0 TO SON
STORE 0 TO PON
STORE 0 TO CON
STORE 0 TO ION
STORE 0 TO YON
STORE 0 TO LON
STORE 0 TO FON
STORE 0 TO USUB TABLE 5-continued

```
STORE 0 TO MSUB
STORE 0 TO TSUB
STORE 0 TO HSUB
STORE 0 TO ASUB
STORE 0 TO SSUB
STORE 0 TO PSUB
STORE 0 TO CSUB
STORE 0 TO ISUB
STORE 0 TO YSUB
STORE 0 TO LSUB
STOFE 0 TO FSUB
STORE 0 TO ANAL
STORE 0 TO EMATCH
STORE 0 TO HMATCH
STORE 0 TO OMATCH
STORE 0 TO IMATCH
STORE 0 TO PTF
Do WHILE .T.
* Program.: Subtraction.fmt
* Date....: 1/13/94
* Version.: FoxBASE+/Mac, revision 1.10
* Notes....: Format file Subtraction
*
SCREEN 1 TYPE 0 HEADING "Screen 1" AT 40,2 SIZE 286,492 PIXELS     FONT "Geneva",9 COLOR 0,0,0,
@ PIXELS 75,120 TO 178,241 STYLE 799 COLOR 0,0,0,0,0,0
@ PIXELS 27,134 SAY "Substraction Menu" STYLE 65536 FONT "Geneva",274 COLOR 0,0,0,-1,-1,-1
@ PIXELS 117,126 GET EMATCH STYLE 65536 FONT "Chicago",12 PICTURE "@*C Exact " SIZE 15,62 CO
@ PIXELS 135,126 GET HMATCH STYLE 65536 FONT "Chicago",12 PICTURE "@*C Homologous" SIZE 15,1
@ PIXELS 153,126 GET OMATCH STYLE 65536 FONT "Chicago",12 PICTURE "@*C Other spc" SIZE 15,84
@ PIXELS 90,152 SAY "Matches:" STYLE 65536 FONT "Geneva",12 COLOR 0,0,0,-1,-1,31 1
@ PIXELS 171,126 GET Imatch STYLE 65536 FONT "Chicago",12 PICTURE "@*C Incyte" SIZE 15,65 CO
@ PIXELS 252,146 GET initiate STYLE 0 FONT "Geneva",12 SIZE 15,70 COLOR 0,0,0,-1,-1,-1
@ PIXELS 270,146 GET terminate STYLE 0 FONT "Geneva",12 SIZE 15,70 COLOR 0,0,0,-1,-1,-1
@ PIXELS 234,134 SAY "Include clones *" STYLE 65536 FONT "Geneva",12 COLOR 0,0,0,-1,-1,-1
@ PIXELS 270,125 SAY "->" STYLE 65536 FONT "Geneva",14 COLOR 0,0,0,-1,-1,-1
@ PIXELS 198,126 GET PTF STYLE 65536 FONT "Chicago",12 PICTURE "@*C Print to file" SIZE 15,9
@ PIXELS 72,9 TO 277,115 STYLE 799 COLOR 0,0,0,0,0,0
@ PIXELS 90,18 GET UON STYLE 65336 FONT "Chicago",10 PICTURE "@*C U937" SIZE 13,49 COLOR 0,0
@ PIXELS 99,18 GET MON STYLE 65536 FONT "Chicago",10 PICTURE '@*C HMC" SIZE 13,45 COLOR 0,0
@ PIXELS 108,18 GET TON STYLE 65536 FONT "Chicago",10 PICTURE "@"C THP-1* SIZE 13,54 COLOR
@ PIXELS 117,18 GET HON STYLE 65536 FONT "Chicago",10 PICTURE "@*C HUVEC" SIZE 13,55 COLOR 0
@ PIXELS 126,18 GET AON STYLE 65536 FONT "Chicago",10 PICTURE "@*C Adenoid" SIZE 13,67 COLOR
@ PIXELS 135,18 GET SON STYLE 65536 FONT "Chicago",10 PICTURE "@*C Spleen" SIZE 13,59 COLOR
@ PIXELS 144,18 GET PON STYLE 65536 FONT "Chicago",10 PICTURE "@*C Con THP" SIZE 13,65 COLOR
@ PIXELS 153,18 GET CON STYLE 65536 FONT "Chicago",10 PICTURE "@*C Con HUVEC" SIZE 13,79 COL
@ PIXELS 162,18 GET YON STYLE 65536 FONT "Chicago",10 PICTURE "@*C T + B cell" SIZE 13,70 CO
@ PIXELS 171,18 GET ION STYLE 65536 FONT "Chicago",10 PICTURE "@*C Cornea" SIZE 13,61 COLOR
@ PIXELS 180,18 GET LON STYLE 65536 FONT "Chicago",10 PICTURE "@*C Liver" SIZE 13,50 COLOR 0
@ PIXELS 189,18 GET FON STYLE 65536 FONT "Chicago",10 PICTURE "@*C Fibroblast" SIZE 13,80 CO
@ PIXELS 72,288 TO 277,394 STYLE 799 COLOR 0,0,0,0,0,0
@ PIXELS 90,297 GET USUB STYLE 65536 FONT "Chicago",10 PICTURE "@*C U937" SIZE 13,49 COLOR 0
@ PIXELS 99,297 GET HSUB STYLE 65536 FONT "Chicago",10 PICTURE "@*C HMC" SIZE 13,45 COLDR O,
@ PIXELS 108,297 GET TSUB STYLE 65536 FONT "Chicago",10 PICTURE "@*C THP-1" SIZE 13,54 COLOR
@ PIXELS 117,297 GET KSUB STYLE 65536 FONT "Chicago",10 PICTURE "@*C HUVEC" SIZE 13,55 COLOR
@ PIXELS 126,297 GET ASUB STYLE 65536 FONT "Chicago",10 PICTURE "@*C Adenoid" SIZE 13,67 COL
@ PIXELS 135,297 GET SSUB STYLE 65536 FONT "Chicago",10 PICTURE "@*C Spleen" SIZE 13,59 COLO
@ PIXELS 144,297 GET PSUB STYLE 65536 FONT "Chicago",10 PICTURE "@*C Con TMP" SIZE 13,65 COL
@ PIXELS 153,297 GET CSUB STYLE 65536 FONT "Chicago",10 PICTURE "@*C Con HUVEC" SIZE 13,79 C
@ PIXELS 162,297 GET YSUB STYLE 65536 FONT "Chicago",10 PICTURE "@*C T + B cell" SIZE 13,70
@ PIXELS 171,297 GET ISUB STYLE 65536 FONT "Chicago",10 PICTURE "@*C Cornea" SIZE 13,61 COLO
@ PIXELS 180,297 GET LSUB STYLE 65536 FONT "Chicago",10 PICTURE "@*C Liver" SIZE 13,50 COLOR
@ PIXELS 189,297 GET FSUB STYLE 65536 FONT "Chicago",10 PICTURE "@*C Fibroblast" SIZE 13,80
@ PIXELS 63,314 SAY "Subtract:" STYLE 65536 FONT "Geneva",14 COLOR 0,0,0,-1,-1,-1
@ PIXELS 54,72 GET ANAL STYLE 65536 FONT "Chicago",12 PICTURE "@*R Overall;Function" SIZE 41
*
* EOF: Subtraction.fmt
READ
    IF TERMINATE=0
    CLEAR
    CLOSE DATABASES
    USE "SmartGuy:FoxBASE+/Mac:fox files:clones.dbf"
    SET SAFETY ON
    SCREEN 1 OFF
    RETURN
    ENDIF
STORE VAL(SYS(2)) TD STARTIME
clear
SET TALK ON
GAP = TERMINATE-INITIATE+1
```

TABLE 5-continued

```
GO INITIATE
COPY NEXT GAP FIELDS NUMBER,L,D,F,Z,R,ENTRY,S,DESCRIPTOR,START,RFEND, I TO TEMPNUM
USE TEMPNUM
COUNT TO TOT
COPY TO TEMPRED FOR D='E'.OR.D='O'.OR.D='H'.OR.D='N'.D='I'
USE TEMPRED
    IF Ematch=0 .AND. Hmatch=0 .AND. Omatch=0 .AND. IMATCH=0
    COPY TO TEMPDESIG
    ELSE
    COPY STRUCTURE TD TEMPDESIG
    USE TEMPDESIG
    IF Ematch=1
    APPEND FROM TEMPNUM FOR D='E'
    ENDIF
    IF Hmatch=1
    APPEND FROM TEMPNUM FOR D='H'
    ENDIF
    IF Omatch=1
    APPEND FROM TEMPNUM FOR D='O'
    ENDIF
    IF Imatch=1
    APPEND FROM TEMPNUM FOR D='I'.OR.D='X'
*.OR.D='N'
    ENDIF
ENDIF
COUNT TO STARTOT
COPY STRUCTURE TO TEMPLIB
USE TEMPLIB
    IF UON=0 .AND. MON=0 .AND. TON=0 .AND. HON=0 .AND. AON=0.AND.SON=0.AND.PON=0.AND.CCN=0.AND
    APPEND FROM TEMPDESIG
    ENDIF
    IF UON=1
    APPEND FROM TEMPDESIG FOR L='U'
    ENDIF
    IF MON=1
    APPEND FROM TEMPDESIG FOR L='M'
    ENDIF
    IF TON=1
    APPEND FROM TEMPDESIG FOR L='T'
    ENDIF
    IF HON=1
    APPEND FROM TEMPDESIG FOR L='H'
    ENDIF
    IF AON=1
    APPEND FROM TEXPDESIG FOR L='A'
    ENDIF
    IF SON=1
    APFEND FROM TEMPDESIG FOR L='S'
    ENDIF
    IF PON=1
    APPEND FROM TEMPDESIG FOR L='P'
    ENDIF
    IF CON=1
    APPEND FROM TEMPDESIG FOR L='C'
    ENDIF
    IF ION=1
    APPEND FROM TEMPDESIG FOR L='I'
    ENDIF
    IF YON=1
    APPEND FROM TEMPDESIG FOR L='Y'
    ENDIF
    IF LON=1
    APPEND FROM TEMPDESIG FOR L='L'
    ENDIF
    IF FON=1
    APPEND FROM TEMPDESIG FOR L='F'
    ENDIF
COUNT TO ANALTOT
USE TEMPDESIG
COPY STRUCTURE TO TEMPSUB
USE TEMPSUB
    IF USUB=0 .AND. MSUB=0 .AND. TSUB=0 .AND. HSUB=0 .AND. ASUB=0.AND.SSUB=0.AND.PSUB=0.AND.CS
    APPEND FROM TEMPDESIG
    ENDIF
    IF USUB=1
    APPEND FROM TEMFDESIG FOR L='U'
    ENDIF
    IF MSUB=1
    APPEND FROM TEMPDESIG FOR L='M'
```

TABLE 5-continued

```
    ENDIF
    IF TSUB=1
    APPEND FROM TEMPDESIG FOR L='T'
    ENDIF
    IF HSUB=1
    APPEND FROM TEMPDESIG FOR L='H'
    ENDIF
    IF ASUB=1
    APPEND FROM TEMPDESIG FOR L='A'
    ENDIF
    IF SSUB=1
    APPEND FROM TEMPDESIG FOR L='S'
    ENDIF
    IF PSUB=1
    APPEND FROM TEMPDESIG FOR L='P'
    ENDIF
    IF CSUB=1
    APPEND FROM TEMPDESIG FOR L='C'
    ENDIF
    IF ISUB=1
    APPEND FROM TEMPDESIG FOR L='I'
    ENDIF
    IF YSUB=1
    APPEND FROM TEMPDESIG FOR L='Y'
    ENDIF
    IF LSUB=1
    APPEND FROM TFMPDESIG FOR L='L'
    ENDIF
    IF FSUB=1
    APPEND FROM TEMPDESIG FOR L='F'
    ENDIF
COUNT TO SUBTRACTOT
SET TALK OFF
*******************************************************************************
* COMPRESSION SUBROUTINE A
? 'COMPRESSING QUERY LIBRARY'
USE TEMPLIB
SORT ON ENTRY,NUMBER TO LIBSORT
USE LIBSORT
COUNT TO IDGENE
REPLACE ALL RFEND WITH 1
MARK1 = 1
SW2=0
DO WHILE SW2=0 ROLL
    IF MARK1 >= IDGENE
    PACK
    COUNT TO AUNIQUE
    SW2=1
    LOOP
    ENDIF
GO MARK1
DUP = 1
STORE ENTRY TD TESTA
STORE D TO DESIGA
SW = 0
DO WHILE SW=0 TEST
SKIP
STORE ENTRY TO TESTB
STDRE D TO DESIGB
    IF TESTA = TESTB.AND.DESIGA=DESIGB
    DELETE
    DUP = DUP+1
    LOOP
    ENDIF
GO MARK1
REPLACE RFEND WITH DUP
MARK1 = MARK1+DUP
SW=1
LOOP
ENDDO TEST
LOOP
ENDDO ROLL
SORT ON RFEND/D.NUMBER TO TEMPTARSORT
USE TEMPTARSORT
"REPLACE ALL START WITHRFEND IDGENE"10000
COUNT TO TEMPTARCO
*******************************************************************************
* COMPRESSION SUBROUTINE B
? 'COMPRESSING TARGET LIBRARY'
```

TABLE 5-continued

```
USE TEMPSUB
SORT ON ENTRY,NUMBER TO SUBSORT
USE SUBSORT
COUNT TO SUBGENE
REPLACE ALL RFEND WITH 1
MARK1 = 1
SW2=0
DO WHILE SW2=0 ROLL
    IF MARK1 >= SUBGENE
    PACK
    COUNT TO BUNIQUE
    SW2=1
    LOOP
    ENDIF
GO MARK1
DUP = 1
STORE ENTRY TO TESTA
STORE D TO DESIGA
SW = 0
DO WHILE SW=0 TEST
SKIP
STORE ENTRY TO TESTB
STORE D TO DESIGB
    IF TESTA = TESTB.AND.DESIGA=DESIGB
    DELETE
    DUP = DUP+1
    LOOP
    ENDIF
GO MARK1
REPLACE RFEND WITH DUP
MARK1 = MARK1+DUP
SW=1
LOOP
ENDDO TEST
LOOP
ENDDO ROLL
SORT ON RFEND/D,NUMBER TO TEMPSUBSORT
USE TEMPSUBSORT
*REPLACE ALL START WITH RFEND/IDGENE*10000
COUNT TO TEMPSUBCO
********************************************************************************
*FUSION ROUTINE
? 'SUBTRACTING LIBRARIES'
USE SUBTRACTION
COPY STRUCTURE TO CRUNCHER
SELECT 2
USE TEMPSUBSORT
SELECT 1
USE CRUNCHER
APPEND FROM TEMPTAPSORT
COUNT TO BAILOUT
MARK = 0
DO WHILE .T.
SELECT 1
MARK = MARK+1
    IF MARK>BAILOUT
    EXIT
    ENDIF
GO MARK
STORE ENTRY TO SCANNER
SELECT 2
LOCATE FOR ENTRY=SCANNER
IF FOUND( )
STORE RFEND TO BIT1
STORE RFEND TO BIT2
ELSE
STORE 1/2 TO BIT1
STORE 0 TO BIT2
ENDIF
SELECT 1
REPLACE BGFREQ WITH BIT2
REPLACE ACTUAL WITH BIT1
LOOP
ENDDO
SELECT 1
REPLACE ALL RATIO WITH RFEND/ACTUAL
? 'DOING FINAL SORT BY RATIO'
```

TABLE 5-continued

```
SORT ON RATIO/D,BGFREQ/D, DESCRIPTOR TO FINAL
USE FINAL
********************************************************************************
set talk off
DO CASE
CASE PTF=0
SET DEVICE TO PRINT
SET PRINT ON
CASE PTF=1
SET ALTERNATE TO "INCT 20011:Substraction 1"
SET ALTERNATE ON
ENDCASE
STORE VAL(SYS(2)) TO FINTIME
IF FINTIME<STARTIME
STORE FINTIME+86400 TO FINTIME
ENDIF
STORE FINTIME - STARTIME TO COMPSEC
STORE COMPSEC/60 TO COMPMIN
********************
SET MARGIN TO 10
@1,13 SAY "Library Subtraction Analysis" STYLE 65536 FONT "Geneva",274 COLOR 0,0,0,-1,-1,-1
?
?
?
?
? date( )
?? '          '
?? TIME( )
? 'Clone numbers   '
?? STR(INITIATE,5,0)
?? ' through '
?? STR(TERMINATE,6,0)
? 'Libraries:   '
IF UON=0 .AND. MON=0 .AND. TCN=0.AND.HON=0.AND.AON=0.AND.SON=0.AND.PON=0.AND.CON=0.AND.YON=0
?? 'All'
ENDIF
IF UON=1
?? 'U937,'
ENDIF
IF MON=1
?? 'HMC,'
ENDIF
IF TCN=1
?? 'THP-1'
ENDIF
IF HCN=1
?? 'HUVEC'
ENDIF
IF ACN=1
?? 'Adenoid'
ENDIF
IF SON=1
?? 'Spleen'
ENDIF
IF PON =1
?? 'Control THP'
ENDIF
IF CON =1
?? 'Control HUVEC'
ENDIF
IF YON=1
?? 'T + B lymphoblast'
ENDIF
IF ION=1
?? 'Corneal stroma'
ENDIF
IF LON=1
?? 'Liver'
ENDIF
IF FCON=1
?? 'Fibroblast'
ENDIF
? 'Subtracting: '
IF USUB=0 .AND. MSUB=0 .AND. TSUB=0.AND.HSUB=0.AND.ASUB=0.AND.SSUB=0.AND.PSUB=0.AND.CSUB=0.A
?? 'All'
ENDIF
IF USUB=1
?? 'U937,'
ENDIF
```

TABLE 5-continued

```
IF MSUB=1
?? 'HMC,'
ENDIF
IF TSUB=1
?? 'THP-1'
ENDIF
IF HSUB=1
?? 'HUVEC'
ENDIF
IF ASUB=1
?? 'Adenoid'
ENDIF
IF SSUB=1
?? 'Spleen'
ENDIF
IF PSUB=1
?? 'Control THP'
ENDIF
IF CSUB=1
?? 'Control HUVEC'
ENDIF
IF YSUB=1
?? 'T + B lymphoblast'
ENDIF
IF ISUB=1
?? 'Corneal stroma'
ENDIF
IF LSUB=1
?? 'Liver'
ENDIF
IF FSUB=1
?? 'Fibroblast'
ENDIF
? 'Designations: '
IF Ematch=0 .AND. Hmatch=0.AND.Omatch=0 .AND.Imatch=0
?? 'All'
SCREEN 1 TYPE 0 HEADING "Screen 1" AT 40,2 SIZE 286,492 PIXELS FONT "Helvetica",265 COLOR 0
? 'Other binding proteins:'
SCREEN 1 TYPE 0 HEADING "Screen 1" AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='I'
?
SCREEN 1 TYPE 0 HEADING "Screen 1" AT 40,2 SIZE 286,492 PIXELS FONT "Helvetica",268 COLOR 0
? '                           ONCOGENES'
?
SCREEN 1 TYPE 0 HEADING "Screen 1" AT 40,2 SIZE 286,492 PIXELS FONT "Helvetica",265 COLOR 0
? 'General oncogenes:'
SCREEN 1 TYPE 0 HEADING "Screen 1" AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='O'
SCREEN 1 TYPE 0 HEADING "Screen 1" AT 40,2 SIZE 286,492 PIXELS FONT "Helvetica",265 COLOR 0
? 'GTP-binding proteins:'
SCREEN 1 TYPE 0 HEADING "Screen 1" AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='G'
SCREEN 1 TYPE 0 HEADING "Screen 1" AT 40,2 SIZE 286,492 PIXELS FONT "Helvetica",265 COLOR 0
? 'Viral elements:'
SCREEN 1 TYPE 0 HEADING "Screen 1" AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='V'
SCREEN 1 TYPE 0 HEADING "Screen 1" AT 40,2 SIZE 286,492 PIXELS FONT "Helvetica",265 COLOR 0
? 'Kinases and Phosphatases:'
SCREEN 1 TYPE 0 HEADING "Screen 1" AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='Y'
SCREEN 1 TYPE 0 HEADING "Screen 1" AT 40,2 SIZE 286,492 PIXELS FONT "Helvetica",265 COLOR 0
? 'Tumor-related antigens:'
SCREEN 1 TYPE 0 HEADING "Screen 1" AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='A'
?
SCREEN 1 TYPE 0 HEADING "Screen 1" AT 40,2 SIZE 286,492 PIXELS FONT "Helvetica",268 COLOR 0
? '            PROTEIN SYNTHETIC MACHINERY PROTEINS'
? '
SCREEN 1 TYPE 0 HEADING "Screen 1" AT 40,2 SIZE 286,492 PIXELS FONT "Helvetica",265 COLOR 0
? 'Transcription and Nucleic Acid-binding proteins:'
SCREEN 1 TYPE 0 HEADING "Screen 1" AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='D'
SCREEN 1 TYPE 0 HEADING "Screen 1" AT 40,2 SIZE 286,492 PIXELS FONT "Helvetica",265 COLOR 0
? 'Translation:'
SCREEN 1 TYPE 0 HEADING "Screen 1" AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='T'
SCREEN 1 TYPE 0 HEADING "Screen 1" AT 40,2 SIZE 286,492 PIXELS FONT "Helvetica",265 COLOR 0
? 'Ribosomal proteins:'
SCREEN 1 TYPE 0 HEADING "Screen 1" AT 40,2 SIZE 286,492 PIXELS FONT "Geneva",7 COLOR 0,0,0,
```

TABLE 5-continued

```
list OFF fields number,D,F,Z,R,ENTRY,S,DESCRIPTOR,BGFREQ,RFEND,RATIO,I FOR R='R'
SCREEN 1 TYPE 0 HEADING "Screen 1" AT 40,2 SIZE 286,492 PIXELS FONT "Helvetica",265 COLOR 0
? 'Protein processing:'
SCREEN 1 TYPE 0 HEADING "Screen 1" AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='L'
?
SCREEN 1 TYPE 0 HEADING "Screen 1" AT 40,2 SIZE 286,492 PIXELS FONT "Helvetica",268 COLOR 0
?
? '                          ENZYMES'
?
SCREEN 1 TYPE 0 HEADING "Screen 1" AT 40,2 SIZE 286,492 PIXELS FONT "Helvetica",265 COLOR 0
? 'Ferroproteins:'
SCREEN 1 TYPE 0 HEADING "Screen 1" AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='P'
SCREEN 1 TYPE 0 HEADING "Screen 1" AT 40,2 SIZE 286,492 PIXELS FONT "Helvetica",265 COLOR 0
? 'Oxidative phosphorylation:'
SCREEN 1 TYPE 0 HEADING "Screen 1" AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='Z'
SCREEN 1 TYPE 0 HEADING "Screen 1" AT 40,2 SIZE 286,492 PIXELS FONT "Helvetica",265 COLOR 0
? 'Sugar metabolism:'
SCREEN 1 TYPE 0 HEADING "Screen 1" AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='Q'
SCREEN 1 TYPE 0 HEADING "Screen 1" AT 40,2 SIZE 286,492 PIXELS FONT "Helvetica",265 COLOR 0
? 'Amino acid metabolism:'
SCREEN 1 TYPE 0 HEADING "Screen 1" AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='M'
SCREEN 1 TYPE 0 HEADING "Screen 1" AT 40,2 SIZE 286,492 PIXELS FONT "Helvetica",265 COLOR 0
? 'Nucleic acid metabolism:'
SCREEN 1 TYPE 0 HEADING "Screen 1" AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='N'
SCREEN 1 TYPE 0 HEADING "Screen 1" AT 40,2 SIZE 286,492 PIXELS FONT "Helvetica",265 COLOR 0
? 'Lipid metabolism:'
SCREEN 1 TYPE 0 HEADING "Screen 1" AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='W'
SCREEN 1 TYPE 0 HEADING "Screen 1" AT 40,2 SIZE 286,492 PIXELS FONT "Helvetica",265 COLOR 0
? 'Other enzymes:'
SCREEN 1 TYPE 0 HEADING "Screen 1" AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='E'
?
SCREEN 1 TYPE 0 HEADING "Screen 1" AT 40,2 SIZE 286,492 PIXELS FONT "Helvetica",268 COLOR 0
?
? '                      MISCELLANEOUS CATEGORIES'
?
SCREEN 1 TYPE 0 HEADING "Screen 1" AT 40,2 SIZE 286,492 PIXELS FONT "Helvetica",265 COLOR 0
? 'Stress response:'
SCREEN 1 TYPE 0 HEADING "Screen 1" AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='H'
SCREEN 1 TYPE 0 HEADING "Screen 1" AT 40,2 SIZE 286,492 PIXELS FONT "Helvetica",265 COLOR 0
? 'Structural:'
SCREEN 1 TYPE 0 HEADING "Screen 1" AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='K'
SCREEN 1 TYPE 0 HEADING "Screen 1" AT 40,2 SIZE 286,492 PIXELS FONT "Helvetica",265 COLOR 0
? 'Other clones:'
SCREEN 1 TYPE 0 HEADING "Screen 1" AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='X'
SCREEN 1 TYPE 0 HEADING "Screen 1" AT 40,2 SIZE 286,492 PIXELS FONT "Helvetica",265 COLOR 0
? 'Clones of unknown function:'
SCREEN 1 TYPE 0 HEADING "Screen 1" AT 40,2 SIZE 286,492 PIXELS FONT "Geneva",7 COLOR 0,0,0,
list OFF fields number,D,F,Z,R,ENTRY,S,DESCRIPTOR,BGFREQ,RFEND,RATIO,I FOR R='U'
ENDCAST
DO "Test print.prg"
SET PRINT OFF
SET DEVICE TO SCREEN
CLOSE DATABASES
ERASE TEMPLIB.DBF
ERASE TEMPNUM.DBF
ERASE TEMPDESIG.DBF
SET MARGIN TO 0
CLEAR
LOOP
ENDDO
```

What is claimed is:

1. A method of quantifying relative abundance of mRNA in a biological sample, said method comprising the steps of:

(a) isolating an mRNA population from the biological sample;

(b) identifying gene transcripts by a sequence-specific method, which method comprises (i) making cDNA copies of the mRNA; and (ii) isolating a population of the cDNA copies and producing therefrom a first cDNA library, wherein a selected set of random primers was used in the generation of the first cDNA library;

(c) determining a number of gene transcripts in the mRNA population that encode the same gene product;

(d) processing in a programmed computer the number of gene transcripts that encode the same gene product to calculate a relative abundance of the transcripts within the population of gene transcripts, wherein said relative abundance is calculated by tabulating the number of gene transcripts that encode the same gene product to generate an abundance number and dividing the abundance number by the total number of gene transcripts in the mRNA population to obtain a calculated relative abundance number for each identified gene transcript; and (e) processing the calculated relative abundance of each gene transcript to generate a gene transcript image of the biological sample;

wherein the gene transcript image provides a calculated relative abundance that is quantified for each gene transcript.

2. The method of claim 1, further comprising:

(f) repeating steps (a) through (e) on a sample from a normal human tissue and on a sample from a diseased human tissue to produce a first set of reference gene transcript images from the normal human tissue and a second set of reference gene transcript images from the diseased human tissue;

(g) storing the first and second sets of reference gene transcript images in the programmed computer; and (h) comparing the gene transcript image produced in step (e) of claim 1 with the first and second sets of reference gene transcript images to identify at least one of the reference gene transcript images which closely approximates that of the gene transcript image of the biological sample.

3. The method of claim 2, wherein the biological sample is a biopsy, sputum, blood or urine sample.

4. The method of claim 1, wherein the isolated mRNA population comprises at least 5,000 mRNA molecules.

5. The method of claim 1, wherein the isolated mRNA population comprises at least 100,000 mRNA molecules.

6. A method of producing a gene transcript image analysis, said method comprising the steps of:

(a) obtaining a mixture of mRNA;

(b) making cDNA copies of the mRNA and isolating a representative population of the cDNA copies, wherein a selected set of random primers is used in the generation of the representative population;

(c) inserting the representative population of cDNA copies into cells thereby producing clones;

(d) isolating a population of clones, wherein the cDNA in the clones in the population is representative of mRNA sequences expressed in a sample;

(e) identifying each clone in the population by a sequence-specific method;

(f) determining the number of times each cDNA is represented within the population of clones;

(g) processing in a programmed computer the number of times each cDNA is represented to calculate a relative abundance of expression of each mRNA; and (h) processing the relative abundance of expression of each mRNA to produce a gene transcript image for the population of clones, wherein said relative abundance is calculated by tabulating the number of mRNA transcripts that encode the same gene product to generate a set of abundance numbers and dividing each abundance number by a total number of MRNA transcripts in the mRNA population to obtain a calculated relative abundance number for each identified gene transcript;

wherein the gene transcript image provides a calculated relative abundance that is quantified for each gene transcript.

7. The method of claim 6, also including the step of diagnosing disease by:

repeating steps (a) through (h) on a normal sample from a normal human tissue and on a diseases sample from a diseased human tissue to produce a normal reference gene transcript image analysis from the normal human tissue and a diseased reference gene-transcript image analysis from the diseased human tissue;

storing said normal reference gene transcript image analysis and diseased reference gene transcript image analysis in a programmed computer;

obtaining a patient sample from a human patient, and producing a gene transcript image analysis by preforming steps (a) through (h) from the patient sample; and processing the transcript image analysis of the patient sample in the programmed computer to identify at least one of reference transcript image analysis which closely approximates the patient sample.

8. The method of claim 6, wherein at least 5,000 cDNA clones are processed to calculate a relative abundance of expression of each gene.

9. The method of claim 6, wherein at least 100,000 cDNA clones are processed to calculate a relative abundance of expression of each gene.

10. A computer system for quantifying the relative abundance of identified sequences in a library of nucleic acid or amino acid biological sequences, said system comprising:

means for receiving and storing a set of said biological sequences, where each of the biological sequences is indicative of a different one of the biological sequences of a library of biological sequences prepared from a biological sample;

processing means for calculating an identified sequence value for each biological sequence in the set of biological sequences, where each said identified sequence value is indicative of a degree of match between a biological sequence of the library and at least one biological sequence of a reference library of biological sequences;

means for processing each said identified sequence value to calculate final data values indicative of a number of matches between the corresponding biological sequence and at least one biological sequence of the reference library;

processing means for calculating a relative abundance of identified sequence values corresponding to the set of biological sequences, wherein said relative abundance is calculated by tabulating the number of identified sequence values corresponding to a selected set of identified sequences to generate a set of abundance numbers and dividing each abundance number in the set by a total number of biological sequences in the set of biological sequences to obtain a calculated relative abundance number for each identified sequence value;

processing means for generating a gene transcript image of the biological sample by calculating the relative abundance of each identified sequence value; and means for displaying an abundance sort representing the biological sequences present in the library.

11. The system of claim 10, wherein the biological sequences are cDNA, RNA or amino acid sequences.

12. The computer system of claim 10, wherein the library of biological sequences received and stored by the system comprises at least 5000 biological sequences.

13. The computer system of claim 10, wherein the library of biological sequences received and stored by the system comprises at least 100,000 biological sequences.

14. A computer system for performing analysis to determine the abundance of nucleic acid or amino acid biological sequences in a first library of biological sequences relative to a second library of biological sequences, said system comprising:

means for receiving an storing a first set of biological sequences, where each of the biological sequences is indicative of a different one of the biological sequences of a first library of biological sequences;

means for receiving and storing a second set of biological sequences, where each of the biological sequences is indicative of a different one of the biological sequences of a second library of biological sequences;

processing means for calculating a first set of identified sequence values corresponding to the first set of biological sequences and a second set of identified sequence values corresponding to the second set of biological sequences, wherein each identified sequence value is indicative of a degree of match between a biological sequence of the corresponding first or second sets of biological sequences and at least one biological sequence of a reference library of biological sequences;

means for processing each identified sequence value of said first and second sets of identified sequence values to calculate a first set of final data values and a second set of final data values, wherein each final data value is indicative of a number of matches between biological sequences of the corresponding first or second sets of biological sequences and at least one biological sequence of the reference library;

processing means for calculating a first set of relative abundance numbers, wherein said first set of relative abundance is calculate by tabulating the number of identified sequences of a selected set of identified sequences corresponding to identified sequence values within the first set of identified sequence values to generate a first set of abundance numbers, and dividing each abundance number of the first set of abundance numbers by a total number of biological sequences in the first set of biological sequences to obtain a first set of calculated relative abundance numbers for each identified sequence value of the first set of identified sequence values;

processing means for calculating a second set of relative abundance numbers, wherein said second set of relative abundance is calculated by tabulating the number of identified sequences of a selected set of identified sequences corresponding to identified sequence values within the second set of identified sequence values to generate a second set of abundance numbers, and dividing each abundance number of the second set of abundance numbers by a total number of biological sequences in the second set of biological sequences to obtain a second set of calculated relative abundance numbers for each identified sequence value of the second set of identified sequence values;

processing means for identifying pairs of corresponding relative abundance numbers in the first and second sets of relative abundance numbers;

processing means for generating a ratio value for each identified pair of corresponding relative abundance numbers, wherein the ratio value is calculated by dividing the first relative abundance number of the identified pair by the second relative abundance number of the identified pair; and means for sorting and displaying a list of ratio values;

wherein the list of ratio values represents the abundance of biological sequences in the first set of biological sequences relative to the second set of biological sequences.

15. The system of claim 14, wherein the biological sequences are cDNA, RNA or amino acid sequences.

16. The computer system of claim 14, wherein each of the first and second libraries of biological sequences comprises at least 5,000 biological sequences.

17. The computer system of claim 14, wherein each of the first and second libraries of biological sequences comprises at least 100,000 biological sequences.

* * * * *